US012716080B2

(12) United States Patent
Baskin et al.

(10) Patent No.: US 12,716,080 B2
(45) Date of Patent: Aug. 25, 2026

(54) ENGINEERED PHOSPHOLIPASE D MUTANTS, METHODS OF MAKING ENGINEERED PHOSPHOLIPASE D MUTANTS, AND USES THEREOF

(71) Applicant: CORNELL UNIVERSITY, Ithaca, NY (US)

(72) Inventors: Jeremy Baskin, Ithaca, NY (US); Reika Tei, Ithaca, NY (US)

(73) Assignee: Cornell University, Ithaca, NY (US)

( * ) Notice: Subject to any disclaimer, the term of this patent is extended or adjusted under 35 U.S.C. 154(b) by 244 days.

(21) Appl. No.: 18/716,659

(22) PCT Filed: Dec. 6, 2022

(86) PCT No.: PCT/US2022/080999

§ 371 (c)(1),
(2) Date: Jun. 5, 2024

(87) PCT Pub. No.: WO2023/107929

PCT Pub. Date: Jun. 15, 2023

(65) Prior Publication Data

US 2025/0034604 A1 Jan. 30, 2025

Related U.S. Application Data

(60) Provisional application No. 63/286,447, filed on Dec. 6, 2021.

(51) Int. Cl.

| | |
|---|---|
| ***C12N 15/85*** | (2006.01) |
| ***C12N 1/21*** | (2006.01) |
| ***C12N 9/16*** | (2006.01) |
| ***C12N 15/09*** | (2006.01) |
| ***C12P 7/6409*** | (2022.01) |
| ***C12P 7/6481*** | (2022.01) |
| ***C12Q 1/34*** | (2006.01) |
| ***G01N 33/50*** | (2006.01) |

(52) U.S. Cl.

CPC .............. *C12P 7/6481* (2013.01); *C12N 9/16* (2013.01); *C12P 7/6409* (2013.01); *C12Y 301/04004* (2013.01)

(58) Field of Classification Search

CPC ........ C12N 9/16; C12N 15/09; C12N 15/102; C12N 15/85; C12N 1/21; G01N 33/50; G01N 33/5067; C12Q 1/34

See application file for complete search history.

(56) References Cited

FOREIGN PATENT DOCUMENTS

JP 97011 * 4/2004

OTHER PUBLICATIONS

Allegretti C. et al., "Polar Head Modified Phospholipids by Phospholipase D-Catalyzed Transformations of Natural Phosphatidylcholine for Targeted Applications: An Overview", Catalysts 10:997 (2020).
Angelini A. et al., "Protein Engineering and Selection Using Yeast Surface Display", Methods in Molecular Biology 1319:3-36 (2015).
Athenstaedt K. et al., "Phosphatidic Acid, a Key Intermediate in Lipid Metabolism", Eur. J. Biochem. 266(1):1-16 (Nov. 1999).
Brown H.A. et al., "Biochemical Analysis of Phospholipase D", Methods in Enzymology 434:49-87 (2007).
Joiner A.M.N. et al., "Structural Basis for the Initiation of COPII Vesicle Biogenesis", Structure 29()8):859-872 (Aug. 5, 2021).
Könning D. et al., "Beyond Antibody Engineering: Directed Evolution of Alternative Binding Scaffolds and Enzymes Using Yeast Surface Display", Microb. Cell Factories 17:32 (2018).
Mohanty J G et al., "A Highly Sensitive Fluorescent Micro-Assay of H2O2 Release from Activated Human Leukocytes Using a Dihydroxyphenoxazine Derivative", Journal of Immunological Methods 202(2):133-141 (Mar. 1997).
Rosano G.L. et al., "Recombinant Protein Expression in *Escherichia coli*: Advances and Challenges", Frontiers in Microbiology 5(172) (Apr. 2014).
Tanguy E. et al., "Phosphatidic Acid: From Pleiotropic Functions to Neuronal Pathology", Frontiers in Cellular Neuroscience 13(2):1-8 (Jan. 2019).
Tei R. et al., "Activity-Based Directed Evolution of a Membrane Editor in Mammalian Cells", bioRxiv preprint doi: https://doi.org/10.1101/2022.09.26.509516 (Sep. 26, 2022).
Tei R. et al., "Induced Proximity Tools for Precise Manipulation of Lipid Signaling", Current Opinion in Chemical Biology 65:93-100 (Dec. 2021).
Tei R. et al., "Spatiotemporal Control of Phosphatidic Acid Signaling With Optogenetic, Engineered Phospolipase Ds", Journal of Cell Biology 219(3):e201907013 (2020).
Wang Y. et al., "Directed Evolution: Methodologies and Applications", Chemical Reviews 121(20):12384-12444 (Oct. 2021).
Yang H Y et al., "Phosphohydrolase and Transphosphatidylation Reactions of Two Streptomyces Phospholipase D Enzmes: Covalent Versus Noncovalent Catalysis", Protein Science 12:2087-2098 (2003).
Zhang H. et al., "Combining Cell Surface Display and DNA Shuffling Technology for Directed Evolution of Streptomyces Phospholipase D and Synthesis of Phosphatidylserine", Journal of Agricultural and Food Chemistry 67 (7):13119-13126 (Nov. 2019).
UniProtKB Accession No. P8417 (2 pages) (Jun. 2, 2021).
UniProtKB Accession No. A0A7W7LBP9 (2 pages) (Sep. 29, 2021).
International Search Report and Written Opinion dated May 4, 2023 received in International Application No. PCT/US2022/080999.

* cited by examiner

*Primary Examiner* — Maryam Monshipouri

(74) *Attorney, Agent, or Firm* — Scully, Scott, Murphy & Presser, P.C.

(57) ABSTRACT

Engineered phospholipase D mutants are described herein. Also described herein are methods of making engineered phospholipase D mutants. Additionally, methods of using engineered phospholipase D mutants are described.

26 Claims, 19 Drawing Sheets
(17 of 19 Drawing Sheet(s) Filed in Color)

Specification includes a Sequence Listing.

D

| Entry | $R_3$ | PAlc yield (%) | PA yield (%) |
|---|---|---|---|
| 1 |  | — | 84% |
| 2 |  | 98% | 2% |
| 3 |  | 95% | 2% |
| 4 |  | 52% | 30% |
| 5 |  | 78% | 15% |
| 6 |  | 65% | 12% |
| 7 |  | 99% | <1% |
| 8 |  | 98% | <1% |
| 9 |  | 99% | <1% |
| 10 |  | 98% | <1% |

B

SEQUENCE LISTING

```
Sequence total quantity: 155
SEQ ID NO: 1            moltype = AA  length = 506
FEATURE                 Location/Qualifiers
source                  1..506
                        mol_type = protein
                        organism = Streptomyces sp.
SEQUENCE: 1
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMPTMHKD TNPKASPATG NVPVIAVGGL GVGIKDVDPK STFRPDLPTA SDTKCVVGLH  300
DNTNADRDYD TVNPEESALR ALVASAKGHI EISQQDLNAT CPPLPRYDIR LYDALAAKMA  360
AGVKVRIVVS DPANRGAVGS GGYSQIKSLS EISDTLRNRL ANITGGQQAA KTAMCSNLQL  420
ATFRSSPNGK WADGHPYAQH HKLVSVDSST FYIGSKNLYP SWLQDFGYIV ESPEAAKQLD  480
AKLLDPQWKY SQETATVDYA RGICNA                                       506

SEQ ID NO: 2            moltype = AA  length = 506
FEATURE                 Location/Qualifiers
REGION                  1..506
                        note = mutant
source                  1..506
                        mol_type = protein
                        organism = synthetic construct
SEQUENCE: 2
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMATMHKD TNPKASPATG NVPIIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGSQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                       506

SEQ ID NO: 3            moltype = AA  length = 506
FEATURE                 Location/Qualifiers
REGION                  1..506
                        note = mutant
source                  1..506
                        mol_type = protein
                        organism = synthetic construct
SEQUENCE: 3
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVM PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMATMHKD TNPKASPATG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGSQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                       506

SEQ ID NO: 4            moltype = AA  length = 506
FEATURE                 Location/Qualifiers
REGION                  1..506
                        note = mutant
source                  1..506
                        mol_type = protein
                        organism = synthetic construct
SEQUENCE: 4
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMATMHKD TNPKASPATG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSSA FYIGSKNLYP SWLQDFGYIV ESPEAAKQLD  480
AKLLDPQWKY SQETATVDYA RGICNA                                       506

SEQ ID NO: 5            moltype = AA  length = 506
FEATURE                 Location/Qualifiers
REGION                  1..506
                        note = mutant
source                  1..506
                        mol_type = protein
                        organism = synthetic construct
```

```
SEQUENCE: 5
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG 120
AAPVYHMNVI PSKYRDELTA KLGKAAENIT LNVASMTTSK TAFSWNHSKI LVVDGQSALT 180
GGINSWKDDY LDTTHPVSDV DLALTGPAAG SAGRYLDTLW TWTCQNKSNI ASVWFAASGN 240
AGCMPTMHKD TNPKASPTTG NVPVIAVGGL GVGIKDVDPK STFRPDLPTA SDTKCVVGLH 300
DNTNADRDYD TVNPEESALR ALVASARSHI EISQQDLNAT CPPLPRYDIR LYDALAAKMA 360
AGVKVRIVVS DPANRGAVGS VGYSQIKSLS EISDTLRNRL ANITGSQQAA KTAMCSNLQL 420
ATFRSSPNDK WADGHPYAQH HKLVSVDSST FYIGSKNLYP SWLQDFGYIV ESPEAAKQLE 480
AKLLDPQWKY SQETATVDYA RGICNA                                     506

SEQ ID NO: 6           moltype = AA  length = 506
FEATURE                Location/Qualifiers
REGION                 1..506
                       note = mutant
source                 1..506
                       mol_type = protein
                       organism = synthetic construct
SEQUENCE: 6
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG 120
AAPVYHMNVM PSKYRDELTA KLGKAAENIT LNVASMTTSK TAFSWNHSKI LVVDGQSALT 180
GGINSWKDDY LDTTHPVSDV DLALTGPAAG SAGRYLDTLW TWTCQNKSNI ASVWFAASGN 240
AGCMATMHKD TNPKASPTTG NVPVIAVGGL GVGIKDVDPK STFRPDLPTA SDTKCVVGLH 300
DNTNADRDYD TVNPEESALR ALVASARSHI EISQQDLNAT CPPLPRYDIR LYDALAAKMA 360
AGVKVRIVVS DPANRGAVGS VGYSQIKSLS EISDTLRNRL ANITGSQQAA KTAMCSNLQL 420
ATFRSSPNDK WADGHPYAQH HKLVSVDSST FYIGSKNLYP SWLQDFGYIV ESPEAAKQLD 480
AKLLDPQWKY SQETATVDYA RGICNA                                     506

SEQ ID NO: 7           moltype = AA  length = 506
FEATURE                Location/Qualifiers
REGION                 1..506
                       note = mutant
source                 1..506
                       mol_type = protein
                       organism = synthetic construct
SEQUENCE: 7
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG 120
AAPVYHMNVI PSKYRDELTA KLGKAAENIT LNVASMTTSK TAFSWNHSKI LVVDGQSALT 180
GGINSWKDDY LDTTHPVSDV GLALTGPAAG SAGRYLDTLW TWTCQNKSNI ASVWFAASGN 240
AGCMPTMHKD TNPKASPTTG NVPVIAVGGL GVGIKDVDPK STFRPDLPTA SDTKCVVGLH 300
DNTNADRDYD TVNPEESALR ALVASAKSHI EISQQDLNAT CPPLPRYDIR LYDALAAKMA 360
AGVKVRIVVS DPANRGAVGS VGYSQIKSLS EISDTLRNRL ANITGSQQAA KTAMCSNLQL 420
ATFRSSPNDK WADGHPYAQH HKLVSVDSST FYIGSKNLYP SWLQDFGYIV ESPEAAKQLD 480
AKLLDPQWKY SQETATVDYA RGICNA                                     506

SEQ ID NO: 8           moltype = AA  length = 506
FEATURE                Location/Qualifiers
REGION                 1..506
                       note = mutant
source                 1..506
                       mol_type = protein
                       organism = synthetic construct
SEQUENCE: 8
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG 120
AAPVYHMNVI PSKYRDELTA KLGKAAENIT LNVASMTTSK TAFSWNHSKI LVVDGQSALT 180
GGINSWKDDY LDTTHPVSDV GLALTGPAAG SAGRYLDTLW TWTCQNKSNI ASVWFAASGN 240
AGCMPTMHKD TNPKASPTTG NVPVIAVGGL GVGIKDVDPK STFRPDLPTA SDTKCVVGLH 300
DNTNADRDYD TVNPEESALR ALVASARSHI EISQQDLNAT CPPLPRYDIR LYDALAAKMA 360
AGVKVRIVVS DPANRGAVGS VGYSQIKSLS EISDTLRNRL ANITGSQQAA KTAMCSNLQL 420
ATFRSSPNDK WADGHPYAQH HKLVSVDSST FYIGSKNLYP SWLQDFGYIV ESPEAAKQLD 480
AKLLDPQWKY SQETATVDYA RGICNA                                     506

SEQ ID NO: 9           moltype = AA  length = 506
FEATURE                Location/Qualifiers
REGION                 1..506
                       note = mutant
source                 1..506
                       mol_type = protein
                       organism = synthetic construct
SEQUENCE: 9
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG 120
AAPVYHMNVI PSKYRDELTA KLGKAAENIT LNVASMTTSK TAFSWNHSKI LVVDGQSALT 180
GGINSWKDDY LDTTHPVSDV GLALTGPAAG SAGRYLDTLW TWTCQNKSNI ASVWFAASGN 240
AGCMATMHKD TNPKASPATG NVPVIAVGGL GVGIKDVDPK STFRPDLPTA SDTKCVVGLH 300
DNTNADRDYD TVNPEESALR ALVASAKSHI EISQQDLNAT CPPLPRYDIR LYDALAAKMA 360
```

-continued

```
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLG  480
AKLLDPQWKY SQETATVDYA RGICNA                                       506

SEQ ID NO: 10          moltype = AA  length = 506
FEATURE                Location/Qualifiers
REGION                 1..506
                       note = mutant
source                 1..506
                       mol_type = protein
                       organism = synthetic construct
SEQUENCE: 10
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV GLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASARSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSSA FYIGSKNLYP SWLQDFGYIV ESPEAAKQLD  480
AKLLDPQWKY SQETATVDYA RGICNA                                       506

SEQ ID NO: 11          moltype = AA  length = 506
FEATURE                Location/Qualifiers
REGION                 1..506
                       note = mutant
source                 1..506
                       mol_type = protein
                       organism = synthetic construct
SEQUENCE: 11
ADSATPHLDA VEQTLRQVSP GLEGDVWERT SGNKLDGSAA DPSDWLLQTP GCWGDDRCVD  60
RVGTKRLLAK ITENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV NLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLE  480
AKLLDPQWKY SQETATVDYA RGICNA                                       506

SEQ ID NO: 12          moltype = AA  length = 506
FEATURE                Location/Qualifiers
REGION                 1..506
                       note = mutant
source                 1..506
                       mol_type = protein
                       organism = synthetic construct
SEQUENCE: 12
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPIYHMNVI PSKYRDELTA KLGKAAENIT LNVASMTTSK TAFSWNHSKI LVVDGQSALT  180
GGINSWKDDY LDTTHPVFDV DLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGSQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                       506

SEQ ID NO: 13          moltype = AA  length = 506
FEATURE                Location/Qualifiers
REGION                 1..506
                       note = mutant
source                 1..506
                       mol_type = protein
                       organism = synthetic construct
SEQUENCE: 13
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVM PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMPTMHKD TNPKASPATG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSSA FYIGSKNLYP SWLQDFGYIV ESPEAAKQLD  480
AKLLDPQWKY SQETATVDYA RGICNA                                       506

SEQ ID NO: 14          moltype = AA  length = 506
FEATURE                Location/Qualifiers
REGION                 1..506
```

```
                          note = mutant
source                    1..506
                          mol_type = protein
                          organism = synthetic construct
SEQUENCE: 14
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVM PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMATMHKD TNPKASPATG NVPIIAVGGL GVGIKDVDPK STFRPDLPTA SDTKCVVGLH  300
DNTNADRDYD TVNPEESALR ALVASAKGHI EISQQDLNAT CPPLPRYDIR LYDALAAKMA  360
AGVKVRIVVS DPANRGAVGS VGYSQIKSLS EISDTLRNRL ANITGGQQAA KNAMCSNLQL  420
ATFRSSPNDK WADGHPYAQH HKLVSVDSSA FYIGSKNLYP SWLQDFGYIV ESPEAAKQLE  480
AKLLDPQWKY SQETATVDYA RGICNA                                      506

SEQ ID NO: 15             moltype = AA  length = 506
FEATURE                   Location/Qualifiers
REGION                    1..506
                          note = mutant
source                    1..506
                          mol_type = protein
                          organism = synthetic construct
SEQUENCE: 15
ADSATPHLDA VEQTLRQVSP GLEGDVWERT SGNKLDGSAA DPSDWLLQTP GCWGDDKCAD  60
RVGTKRLLAK ITENIGNATR TVDISTLAPF PNGAFQDAIV AGLKESAAKG NKLKVRILVG  120
AAPVYHMNVM PSKYRDELTA KLGKAAENIT LNVASMTTSK TAFSWNHSKI LVVDGQSALT  180
GGINSWKDDY LDTTHPVFDV DLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASARSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSSA FYIGSKNLYP SWLQDFGYIV ESPEAAKQLD  480
AKLLDPQWKY SQETATVDYA RGICNA                                      506

SEQ ID NO: 16             moltype = AA  length = 506
FEATURE                   Location/Qualifiers
REGION                    1..506
                          note = mutant
source                    1..506
                          mol_type = protein
                          organism = synthetic construct
SEQUENCE: 16
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TAFSWNHSKI LVVDGQSALT  180
GGINGWKDDY LDTTHPVSDV GLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLE  480
AKLLDPQWKY SQETATVDYA RGICNA                                      506

SEQ ID NO: 17             moltype = AA  length = 506
FEATURE                   Location/Qualifiers
REGION                    1..506
                          note = mutant
source                    1..506
                          mol_type = protein
                          organism = synthetic construct
SEQUENCE: 17
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASARSHI EISQQDLNAT CPPLPRYDIR LYDALAAKMA  360
AGVKVRIVVS DPANRGAVGS VGYSQIKSLS EISDTLRNRL ANITGSQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                      506

SEQ ID NO: 18             moltype = AA  length = 506
FEATURE                   Location/Qualifiers
REGION                    1..506
                          note = mutant
source                    1..506
                          mol_type = protein
                          organism = synthetic construct
SEQUENCE: 18
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAARG NKLKVRILVG  120
```

-continued

```
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMATMHKD TNPKASPATG NVPIIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNGK WADGHPYAQH HKLVSVDSST FYIGSKNLYP SWLQDFGYIV ESPEAAKQLD  480
AKLLDPQWKY SQETATVDYA RGICNA                                      506

SEQ ID NO: 19           moltype = AA  length = 506
FEATURE                 Location/Qualifiers
REGION                  1..506
                        note = mutant
source                  1..506
                        mol_type = protein
                        organism = synthetic construct
SEQUENCE: 19
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVM PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSSA FYIGSKNLYP SWLQDFGYIV ESPEAAKQLD  480
AKLLDPQWKY SQETATVDYA RGICNA                                      506

SEQ ID NO: 20           moltype = AA  length = 506
FEATURE                 Location/Qualifiers
REGION                  1..506
                        note = mutant
source                  1..506
                        mol_type = protein
                        organism = synthetic construct
SEQUENCE: 20
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI KISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                      506

SEQ ID NO: 21           moltype = AA  length = 506
FEATURE                 Location/Qualifiers
REGION                  1..506
                        note = mutant
source                  1..506
                        mol_type = protein
                        organism = synthetic construct
SEQUENCE: 21
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVM PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMATMHKD TNPKASPATG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPDAAKQLD  480
AKLLDPQWKY SQETATVDYA RGICNA                                      506

SEQ ID NO: 22           moltype = AA  length = 506
FEATURE                 Location/Qualifiers
REGION                  1..506
                        note = mutant
source                  1..506
                        mol_type = protein
                        organism = synthetic construct
SEQUENCE: 22
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TALSWNHSKI LVVDGQSALT  180
GGINSWKDDY LDTTHPVSDV DLALTGPAAG SAGRYLDTLW TWTCQNKSNI ASVWFAASGN  240
AGCMPTMYKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSSA FYIGSKNLYP SWLQDFGYIV ESPEAAKQLD  480
AKLLDPQWKY SQETATVDYA RGICNA                                      506
```

```
SEQ ID NO: 23          moltype = AA  length = 506
FEATURE                Location/Qualifiers
REGION                 1..506
                       note = mutant
source                 1..506
                       mol_type = protein
                       organism = synthetic construct
SEQUENCE: 23
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TALSWNHSKI LVVDGQSALT  180
GGINSWKDDY LDTTHPVSDV DLALTGPAAG SAGRYLDTLW TWTCQNKSNI ASVWFAASGN  240
AGCMPTMHRD TNPKASPATG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSSA FYIGSKNLYP SWLQDFGYIV ESPEAAKQLD  480
AKLLDPQWKY SQETATVDYA RGICNA                                       506

SEQ ID NO: 24          moltype = AA  length = 506
FEATURE                Location/Qualifiers
REGION                 1..506
                       note = mutant
source                 1..506
                       mol_type = protein
                       organism = synthetic construct
SEQUENCE: 24
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV GLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASARSHI EISQQDLYAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNGK WADGHPYAQH HKLVSVDSST FYIGSKNLYP SWLQDFGYIV ESPEAAKQLE  480
AKLLDPQWKY SQETATVDYA RGICNA                                       506

SEQ ID NO: 25          moltype = AA  length = 506
FEATURE                Location/Qualifiers
REGION                 1..506
                       note = mutant
source                 1..506
                       mol_type = protein
                       organism = synthetic construct
SEQUENCE: 25
ADSATPHLDA VEQTLRQVSP GLEGDVWERT SGNRLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TALSWNHSKI LVVDGQSALT  180
GGINSWKDDY LDTTHPVSDV GLALTGPAAG SAGRYLDTLW TWTCQNKSNI ASVWFAASGN  240
AGCMPTMHRD TNPKASPATG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLG  480
AKLLDPQWKY SQETATVDYA RGICNA                                       506

SEQ ID NO: 26          moltype = AA  length = 506
FEATURE                Location/Qualifiers
REGION                 1..506
                       note = mutant
source                 1..506
                       mol_type = protein
                       organism = synthetic construct
SEQUENCE: 26
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV GLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                       506

SEQ ID NO: 27          moltype = AA  length = 506
FEATURE                Location/Qualifiers
REGION                 1..506
                       note = mutant
source                 1..506
                       mol_type = protein
```

-continued

```
                        organism = synthetic construct
SEQUENCE: 27
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETAIVDYA RGICNA                                      506

SEQ ID NO: 28           moltype = AA  length = 506
FEATURE                 Location/Qualifiers
REGION                  1..506
                        note = mutant
source                  1..506
                        mol_type = protein
                        organism = synthetic construct
SEQUENCE: 28
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVM PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMATMHKD TNPKASPATG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                      506

SEQ ID NO: 29           moltype = AA  length = 506
FEATURE                 Location/Qualifiers
REGION                  1..506
                        note = mutant
source                  1..506
                        mol_type = protein
                        organism = synthetic construct
SEQUENCE: 29
ADSATPHLDA VEQTLRQVSP GLEGDVWERT SGNKLDGSAA DPSDWLLQTP GCWGDDKCAD  60
RVGTKRLLAK ITENIGNATR TVDISTLAPF PNGAFQDAIV AGLKESAAKG NKLKVRILVG  120
AAPVYHMNVM PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMATMHKD TNPKASPATG NVPVIAVGGL GVGIKDVDPK STFRPDLPTA SDTKCVVGLH  300
DNTNADRDYD TVNPEESALR ALVASAKGHI EISQQDLNAT CPPLPRYDIR LYDALAAKMA  360
AGVKVRIVVS DPANRGAVGS VGYSQIKSLS EISDTLRNRL ANITGSQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                      506

SEQ ID NO: 30           moltype = AA  length = 506
FEATURE                 Location/Qualifiers
REGION                  1..506
                        note = mutant
source                  1..506
                        mol_type = protein
                        organism = synthetic construct
SEQUENCE: 30
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGSQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                      506

SEQ ID NO: 31           moltype = AA  length = 506
FEATURE                 Location/Qualifiers
REGION                  1..506
                        note = mutant
source                  1..506
                        mol_type = protein
                        organism = synthetic construct
SEQUENCE: 31
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
ATPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMATMHKD TNPKASPATG NVPIIAVGGL GVGIKDVDPK STFRPDLPTA SDTKCVVGLH  300
```

-continued

```
DNTNADRDYD TVNPEESALR ALVASAKGHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSSA FYIGSKNLYP SWLQDFGYIV ESPEAAKQLD  480
AKLLDPQWKY SQETATVDYA RGICNA                                      506

SEQ ID NO: 32          moltype = AA  length = 506
FEATURE                Location/Qualifiers
REGION                 1..506
                       note = mutant
source                 1..506
                       mol_type = protein
                       organism = synthetic construct
SEQUENCE: 32
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVM PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMATMHKD TNPKASPATG NVSVIAVGGL GVGIRDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLG  480
AKLLDPQWKY SQETATVDYA RGICNA                                      506

SEQ ID NO: 33          moltype = AA  length = 506
FEATURE                Location/Qualifiers
REGION                 1..506
                       note = mutant
source                 1..506
                       mol_type = protein
                       organism = synthetic construct
SEQUENCE: 33
ADSATPHLDA VEQTLRQVSP GLEGDVWERT SGNKLDGSAA DPSDWLLQTP GCWGDDKCAD  60
RVGTKRLLAK ITENIGNATR TVDISTLAPF PNGAFQDAIV AGLKESAAKG NKLKVRILVG  120
AAPVYHMNVM PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMATMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                      506

SEQ ID NO: 34          moltype = AA  length = 506
FEATURE                Location/Qualifiers
REGION                 1..506
                       note = mutant
source                 1..506
                       mol_type = protein
                       organism = synthetic construct
SEQUENCE: 34
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMATMHKD TNPKASPATG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                      506

SEQ ID NO: 35          moltype = AA  length = 506
FEATURE                Location/Qualifiers
REGION                 1..506
                       note = mutant
source                 1..506
                       mol_type = protein
                       organism = synthetic construct
SEQUENCE: 35
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMATMHKD TNPKASPATG NVPIIAVGGL GVGIKDVDPK STFRPDLPTA SDTKCVVGLH  300
DNTNADRDYD TVNPEESALR ALVASAKGHI EISQQDLNAT CPPLSRYDIR LYDALAAKMA  360
AGVKVRIVVS DPANRGAVGS VGYSQIKSLS EISDTLRNRL ANITGSQQAA KTAMCSNLQL  420
ATFRSSPNDK WADGHPYAQH HKLVSVDSSA FYIGSKNLYP SWLQDFGYIV ESPEAAKQLD  480
AKLLDPQWKY SQETATVDYA RGICNA                                      506

SEQ ID NO: 36          moltype = AA  length = 506
FEATURE                Location/Qualifiers
```

-continued

```
REGION               1..506
                     note = mutant
source               1..506
                     mol_type = protein
                     organism = synthetic construct
SEQUENCE: 36
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV NLAMTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDILRNRL ANITGGQQAA KTAMCSNLQL  420
ATFRSSPNDK WADGHPYAQH HKLVSVDSST FYIGSKNLYP SWLQDFGYIV ESPEAAKQLG  480
AKLLDPQWKY SQETATVDYA RGICNA                                      506

SEQ ID NO: 37        moltype = AA  length = 506
FEATURE              Location/Qualifiers
REGION               1..506
                     note = mutant
source               1..506
                     mol_type = protein
                     organism = synthetic construct
SEQUENCE: 37
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSSA FYIGSKNLYP SWLQDFGYIV ESPEAAKQLD  480
AKLLDPQWKY SQETATVDYA RGICNA                                      506

SEQ ID NO: 38        moltype = AA  length = 506
FEATURE              Location/Qualifiers
REGION               1..506
                     note = mutant
source               1..506
                     mol_type = protein
                     organism = synthetic construct
SEQUENCE: 38
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV GLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASARSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                      506

SEQ ID NO: 39        moltype = AA  length = 506
FEATURE              Location/Qualifiers
REGION               1..506
                     note = mutant
source               1..506
                     mol_type = protein
                     organism = synthetic construct
SEQUENCE: 39
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV GLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                      506

SEQ ID NO: 40        moltype = AA  length = 506
FEATURE              Location/Qualifiers
REGION               1..506
                     note = mutant
source               1..506
                     mol_type = protein
                     organism = synthetic construct
SEQUENCE: 40
ADSATPHLDA VEQTLRQVSP GLEGDVWERT SGNKLDGSAA DPSDWLLQTP GCWGDDKCAD  60
```

-continued

```
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINGWKDDY LDTTHPVSDV GLALTGPAAG SAGRYLDTLW TWTCQNKSNI ASVWFAASGN  240
AGCMPTMHKD TNPKASPATG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                       506

SEQ ID NO: 41          moltype = AA  length = 506
FEATURE                Location/Qualifiers
REGION                 1..506
                       note = mutant
source                 1..506
                       mol_type = protein
                       organism = synthetic construct
SEQUENCE: 41
ADSATPHLDA VEQTLRQVSP GLEGDVWERT SGNKLDGSAA DPSDWLLQTP GCWGDDRCVD  60
RVGTKRLLAK ITENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV NLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                       506

SEQ ID NO: 42          moltype = AA  length = 506
FEATURE                Location/Qualifiers
REGION                 1..506
                       note = mutant
source                 1..506
                       mol_type = protein
                       organism = synthetic construct
SEQUENCE: 42
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV GLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASARSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                       506

SEQ ID NO: 43          moltype = AA  length = 506
FEATURE                Location/Qualifiers
REGION                 1..506
                       note = mutant
source                 1..506
                       mol_type = protein
                       organism = synthetic construct
SEQUENCE: 43
ADTATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV GLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASARSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLG  480
AKLLDPQWKY SQETATVDYA RGICNA                                       506

SEQ ID NO: 44          moltype = AA  length = 506
FEATURE                Location/Qualifiers
REGION                 1..506
                       note = mutant
source                 1..506
                       mol_type = protein
                       organism = synthetic construct
SEQUENCE: 44
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLE  480
```

-continued

```
AKLLDPQWKY SQETATVDYA RGICNA                                   506

SEQ ID NO: 45          moltype = AA  length = 506
FEATURE                Location/Qualifiers
REGION                 1..506
                       note = mutant
source                 1..506
                       mol_type = protein
                       organism = synthetic construct
SEQUENCE: 45
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV NLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                   506

SEQ ID NO: 46          moltype = AA  length = 506
FEATURE                Location/Qualifiers
REGION                 1..506
                       note = mutant
source                 1..506
                       mol_type = protein
                       organism = synthetic construct
SEQUENCE: 46
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV GLALTGPAAG FAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASARSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLG  480
AKLLDPQWKY SQETATVDYA RGICNA                                   506

SEQ ID NO: 47          moltype = AA  length = 506
FEATURE                Location/Qualifiers
REGION                 1..506
                       note = mutant
source                 1..506
                       mol_type = protein
                       organism = synthetic construct
SEQUENCE: 47
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV GLALTGPAAG SAGRYLDTLW TWTCQNKSNI ASVWFAASGN  240
AVCMPTMHKD TNPKASPTTG NVPVIAVGGL GVGIKDVDPK STFRPDLPTA SDTKCVVGLH  300
DNTNADRDYD TVNPEESALR ALVASARSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                   506

SEQ ID NO: 48          moltype = AA  length = 506
FEATURE                Location/Qualifiers
REGION                 1..506
                       note = mutant
source                 1..506
                       mol_type = protein
                       organism = synthetic construct
SEQUENCE: 48
ADSATPHLDA VEQTLRQVSP GLEGDVWERT SGNKLDGSAA DTSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV GLALTGPAAG SAGRYLDTLW TWTCQNKSNI ASVWFAASGN  240
AGCMPTMHKD TNPRHHLTTG NVPVIAVGGL GVGIKDVDPK STFRPDLPTA SDTKCVVGLH  300
DNTNADRDYD TVNPEESALR ALVASARSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                   506

SEQ ID NO: 49          moltype = AA  length = 506
FEATURE                Location/Qualifiers
REGION                 1..506
                       note = mutant
source                 1..506
```

```
                      mol_type = protein
                      organism = synthetic construct
SEQUENCE: 49
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TALSWNHSKI LVVDGQSALT  180
GGINSWKDDY LDTTHPVSDV DLALTGPAAG SAGRYLDTLW TWTCQNKSNI ASVWFAASGN  240
AGCMPTMHRD TNPKASPATG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLG  480
AKLLDPQWKY SQETATVDYA RGICNA                                       506

SEQ ID NO: 50         moltype = AA  length = 506
FEATURE               Location/Qualifiers
REGION                1..506
                      note = mutant
source                1..506
                      mol_type = protein
                      organism = synthetic construct
SEQUENCE: 50
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                       506

SEQ ID NO: 51         moltype = AA  length = 506
FEATURE               Location/Qualifiers
REGION                1..506
                      note = mutant
source                1..506
                      mol_type = protein
                      organism = synthetic construct
SEQUENCE: 51
ADSATPHLDA VEHTLRQVSP GLEGDVWERT SGNKLDGSAA DSSDWLLQTP GCWGDDKCAD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV GLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASARSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                       506

SEQ ID NO: 52         moltype = AA  length = 506
FEATURE               Location/Qualifiers
REGION                1..506
                      note = mutant
source                1..506
                      mol_type = protein
                      organism = synthetic construct
SEQUENCE: 52
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                       506

SEQ ID NO: 53         moltype = AA  length = 506
FEATURE               Location/Qualifiers
REGION                1..506
                      note = mutant
source                1..506
                      mol_type = protein
                      organism = synthetic construct
SEQUENCE: 53
ADSATPHLDA VEQTLRQVSP GLEGDVWERT SGNKLDGSAA DLSDWLLQTP GCWGDDRCAD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TALSWNHSKI LVVDGQSALT  180
GGINSWKDDY LDTTHPVSDV DLALTGPAAG SAGRYLDTLW TWTCQNKSNI ASVWFAASGN  240
```

-continued

```
AGCMPTMHRD TNPKASPATG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLG  480
AKLLDPQWKY SQETATVDYA RGIYNA                                       506

SEQ ID NO: 54          moltype = AA  length = 506
FEATURE                Location/Qualifiers
REGION                 1..506
                       note = mutant
source                 1..506
                       mol_type = protein
                       organism = synthetic construct
SEQUENCE: 54
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSRYRDELTA KLGKAAENIT LNVASMTTSK TAFSWNHSKI LVVDGQSALT  180
GGINSWKDDY LDTTHPVSDV GLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKGHI KISQQDLYAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNGK WADGHPYAQH HKLVSVDSST FYIGSKNLYP SWLQDFGYIV ESPEAAKQLD  480
AKLLDPQWKY SQETATVDYA RGICNA                                       506

SEQ ID NO: 55          moltype = AA  length = 506
FEATURE                Location/Qualifiers
REGION                 1..506
                       note = mutant
source                 1..506
                       mol_type = protein
                       organism = synthetic construct
SEQUENCE: 55
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVM PSKYRDELTA KLGKAAENIT LNVASMTTSK TAFSWNHSKI LVVDGQSALT  180
GGINSWKDDY LDTTHPVFDV DLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKGHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSSA FYIGSKNLYP SWLQDFGYIV ESPEAAKQLD  480
AKLLDPQWKY SQETATVDYA RGICNA                                       506

SEQ ID NO: 56          moltype = AA  length = 506
FEATURE                Location/Qualifiers
REGION                 1..506
                       note = mutant
source                 1..506
                       mol_type = protein
                       organism = synthetic construct
SEQUENCE: 56
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLG  480
AKLLDPQWKY SQETATVDYA RGICNA                                       506

SEQ ID NO: 57          moltype = AA  length = 506
FEATURE                Location/Qualifiers
REGION                 1..506
                       note = mutant
source                 1..506
                       mol_type = protein
                       organism = synthetic construct
SEQUENCE: 57
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAAKG NKLKVRILVG  120
AAPVYHMNVM PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMATMHKD TNPKASPATG NVPIIAVGGL GVGIKDVDPK STFRPDLPTA SDTKCVVGLH  300
DNTNADRDYD TVNPEESALR ALVASAKGHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAKH HKLVSVDSSA FYIGSKNLYP SWLQDFGYIV ESPEAAKQLD  480
AKLLDPQWKY SQETATVDYA RGICNA                                       506

SEQ ID NO: 58          moltype = AA  length = 506
```

-continued

```
FEATURE               Location/Qualifiers
REGION                1..506
                      note = mutant
source                1..506
                      mol_type = protein
                      organism = synthetic construct
SEQUENCE: 58
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV GLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKGHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                      506

SEQ ID NO: 59         moltype = AA  length = 506
FEATURE               Location/Qualifiers
REGION                1..506
                      note = mutant
source                1..506
                      mol_type = protein
                      organism = synthetic construct
SEQUENCE: 59
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWLAASGN  240
AGCMATMHKD TNPKASPATG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                      506

SEQ ID NO: 60         moltype = AA  length = 506
FEATURE               Location/Qualifiers
REGION                1..506
                      note = mutant
source                1..506
                      mol_type = protein
                      organism = synthetic construct
SEQUENCE: 60
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TALSWNHSKI LVVDGQSALT  180
GGINSWKDDY LDTTHPVSDV DLALTGPAAG SAGRYLDTLW TWTCQNKSNI ASVWFAASGN  240
AGCMPTMHRD TNPKASPATG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SRETVTVDYA RGICNA                                      506

SEQ ID NO: 61         moltype = AA  length = 506
FEATURE               Location/Qualifiers
REGION                1..506
                      note = mutant
source                1..506
                      mol_type = protein
                      organism = synthetic construct
SEQUENCE: 61
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGSQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                      506

SEQ ID NO: 62         moltype = AA  length = 506
FEATURE               Location/Qualifiers
REGION                1..506
                      note = mutant
source                1..506
                      mol_type = protein
                      organism = synthetic construct
SEQUENCE: 62
```

-continued

```
ADSATPHLDA VEQTLRQVSP GLEGDVWERT SGNKLDGSAA DPSDWLLQTP GCWGDDKCAD  60
RVGTKRLLAK ITENIGNATR TVDISTLAPF PNGAFQDAIV AGLKESAAKG NKLKVRILVG 120
AAPVYHMNVM PSKYRDELTA KLGKAAENIT LNVASMTTSK TAFSWNHSKI LVVDGQSALT 180
GGINSWKDDY LDTTHPVSDV DLALTGPAAG SAGRYLDTLW TWTCQNKSNI ASVWFAASGN 240
AGCMATMHKD TNPKASPATG NVPVIAVGGL GVGIKDVDPK STFRPDLPTA SDTKCVVGLH 300
DNTNADRDYD TVNPEESALR ALVASAKGHI EISQQDLNAT CPPLPRYDIR LYDALAAKMA 360
AGVKVRIVVS DPANRGAVGS VGYSQIKSLS EISDTLRNRL ANITGSQQAA KTAMCSNLQL 420
ATFRSSPNDK WADGHPYAQH HKLVSVDSST FYIGSKNLYP SWLQDFGYIV ESPEAAKQLD 480
AKLLDPQWKY SQETATVDYA RGICNA                                     506

SEQ ID NO: 63          moltype = AA  length = 506
FEATURE                Location/Qualifiers
REGION                 1..506
                       note = mutant
source                 1..506
                       mol_type = protein
                       organism = synthetic construct
SEQUENCE: 63
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG 120
AAPVYHMNVM PSKYRDELTA KLGKAAENIT LNVASMTTSK TAFSWNHSKI LVVDGQSALT 180
GGINSWKDDY LDTTHPVSDV DLALTGPAAG SAGRYLDTLW TWTCQNKSNI ASVWFAASGN 240
AGCMATMHKD TNPKASPATG NVPVIAVGGL GVGIKDVDPK STFRPDLPTA SDTKCVVGLH 300
DNTNADRDYD TVNPEESALR ALVASAKSHI EISQQDLNAT CPPLPRYDIR LYDALAAKMA 360
AGVKVRIVVS DPANRGAVGS VGYSQIKSLS EISDTLRNRL ANITGGQQAA KTAMCSNLQL 420
ATFRSSPNDK WADGHPYAQH HKLVSVDSST FYIGSKNLYP SWLQDFGYIV ESPEAAKQLD 480
AKLLDPQWKY SQETATVDYA RGICNA                                     506

SEQ ID NO: 64          moltype = AA  length = 506
FEATURE                Location/Qualifiers
REGION                 1..506
                       note = mutant
source                 1..506
                       mol_type = protein
                       organism = synthetic construct
SEQUENCE: 64
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG 120
AAPVYHMNVM PSKYRDELTA KLGKAAENIT LNVASMTTSK TAFSWNHSKI LVVDGQSALT 180
GGINSWKDDY LDTTHPVSDV DLALTGPAAG SAGRYLDTLW TWTCQNKSNI ASVWFAASGN 240
AGCMATMHKD TNPKASPATG NVPVIAVGGL GVGIKDVDPK STFRPDLPTA SDTKCVVGLH 300
DNTNADRDYD TVNPEESALR ALVASAKSHI EISQQDLNAT CPPLPRYDIR LYDALAAKMA 360
AGVKVRIVVS DPANRGAVGS VGYSQIKSLS EISDTLRNRL ANITGGQQAA KTAMCSNLQL 420
ATFRSSPNDK WADGHPYAQH HKLVSVDSST FYIGSKNLYP SWLQDFGYIV ESPEAAKQLD 480
AKLLDPQWKY SQETATVDYA RGICNA                                     506

SEQ ID NO: 65          moltype = AA  length = 506
FEATURE                Location/Qualifiers
REGION                 1..506
                       note = mutant
source                 1..506
                       mol_type = protein
                       organism = synthetic construct
SEQUENCE: 65
ADSATPHLDA VEQTLRQVSP GLEGDVWERT SGNKLDGSAA DPSDWLLQTP GCWGDDKCAD  60
RVGTKRLLAK ITENIGNATR TVDISTLAPF PNGAFQDAIV AGLKESAAKG NKLKVRILVG 120
AAPVYHMNVM PSKYRDELTA KLGKAAENIT LNVASMTTSK TAFSWNHSKI LVVDGQSALT 180
GGINSWKDDY LDTTHPVSDV DLALTGPAAG SAGRYLDTLW TWTCQNKSNI ASVWFAASGN 240
AGCMATMHKD TNPKASPATG NVPVIAVGGL GVGIKDVDPK STFRPDLPTA SDTKCVVGLH 300
DNTNADRDYD TVNPEESALR ALVASAKGHI EISQQDLNAT CPPLPRYDIR LYDALAAKMA 360
AGVKVRIVVS DPANRGAVGS VGYSQIKSLS EISDTLRNRL ANITGSQQAA KTAMCSNLQL 420
ATFRSSPNDK WADGHPYAQH HKLVSVDSST FYIGSKNLYP SWLQDFGYIV ESPEAAKQLD 480
AKLLDPQWKY SQETATVDYA RGICNA                                     506

SEQ ID NO: 66          moltype = AA  length = 506
FEATURE                Location/Qualifiers
REGION                 1..506
                       note = mutant
source                 1..506
                       mol_type = protein
                       organism = synthetic construct
SEQUENCE: 66
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG 120
AAPVYHMNVI PSKYRDELTA KLGKAAENIT LNVASMTTSK TAFSWNHSKI LVVDGQSALT 180
GGINSWKDDY LDTTHPVSDV DLALTGPAAG SAGRYLDTLW TWTCQNKSNI ASVWFAASGN 240
AGCMPTMHKD TNPKASPTTG NVPVIAVGGL GVGIKDVDPK STFRPDLPTA SDTKCVVGLH 300
DNTNADRDYD TVNPEESALR ALVASAKSHI EISQQDLNAT CPPLPRYDIR LYDALAAKMA 360
AGVKVRIVVS DPANRGAVGS VGYSQIKSLS EISDTLRNRL ANITGSQQAA KTAMCSNLQL 420
```

-continued

```
ATFRSSPNDK WADGHPYAQH HKLVSVDSST FYIGSKNLYP SWLQDFGYIV ESPEAAKQLD  480
AKLLDPQWKY SQETATVDYA RGICNA                                       506

SEQ ID NO: 67          moltype = AA  length = 506
FEATURE                Location/Qualifiers
REGION                 1..506
                       note = mutant
source                 1..506
                       mol_type = protein
                       organism = synthetic construct
SEQUENCE: 67
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMATMHKD TNPKASPATG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                       506

SEQ ID NO: 68          moltype = AA  length = 506
FEATURE                Location/Qualifiers
REGION                 1..506
                       note = mutant
source                 1..506
                       mol_type = protein
                       organism = synthetic construct
SEQUENCE: 68
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV GLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                       506

SEQ ID NO: 69          moltype = AA  length = 506
FEATURE                Location/Qualifiers
REGION                 1..506
                       note = mutant
source                 1..506
                       mol_type = protein
                       organism = synthetic construct
SEQUENCE: 69
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV GLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASARSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLG  480
AKLLDPQWKY SQETATVDYA RGICNA                                       506

SEQ ID NO: 70          moltype = AA  length = 506
FEATURE                Location/Qualifiers
REGION                 1..506
                       note = mutant
source                 1..506
                       mol_type = protein
                       organism = synthetic construct
SEQUENCE: 70
ADSATPHLDA VEQTLRQVSP GLEGDVWERT SGNKLDGSAA DPSDWLLQTP GCWGDDRCVD  60
RVGTKRLLAK MTENIGNATR TVDISTLAPF PNGAFQDAIV AGLKESAAKG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                       506

SEQ ID NO: 71          moltype = AA  length = 506
FEATURE                Location/Qualifiers
REGION                 1..506
                       note = mutant
```

-continued

```
source                  1..506
                        mol_type = protein
                        organism = synthetic construct
SEQUENCE: 71
ADSATPHLDA VEQTLRQVSP GLEGDVWERT SGNKLDGSAA DPSDWLLQTP GCWGDDKCAD  60
RVGTKRLLAK MTENIGNATR TVDISTLAPF PNGAFQDAIV AGLKESAARG NKLKVRILVG  120
AAPVYHMNVI PSKYRDELTA KLGKAAENIT LNVASMTTSK TAFSWNHSKI LVVDGQSALT  180
GGINSWKDDY LDTTHPVSDV DLALTGPAAG SAGRYLDTLW TWTCQNKSNI ASVWFAASGN  240
AGCMPTMHKD TNPKASPTTG NVPVIAVGGL GVGIKDVDPK STFRPDLPTA SDTKCVVGLH  300
DNTNADRDYD TVNPEESALR ALVASAKSHI EISQQDLNAT CPPLPRYDIR LYDALAAKMA  360
AGVKVRIVVS DPANRGAVGS VGYSQIKSLS EISDTLRNRL ANITGGQQAA KTAMCSNLQL  420
ATFRSSPNDK WADGHPYAQH HKLVSVDSST FYIGSKNLYP SWLQDFGYIV ESPEAAKQLD  480
AKLLDPQWKY SQETATVDYA RGICNA                                      506

SEQ ID NO: 72           moltype = DNA  length = 28
FEATURE                 Location/Qualifiers
misc_feature            1..28
                        note = primer
source                  1..28
                        mol_type = other DNA
                        organism = synthetic construct
SEQUENCE: 72
cttattgcct ctagctgcgg actccttc                                    28

SEQ ID NO: 73           moltype = DNA  length = 32
FEATURE                 Location/Qualifiers
misc_feature            1..32
                        note = primer
source                  1..32
                        mol_type = other DNA
                        organism = synthetic construct
SEQUENCE: 73
ccgcagctag aggcaataag ttgaaagtta gg                               32

SEQ ID NO: 74           moltype = DNA  length = 32
FEATURE                 Location/Qualifiers
misc_feature            1..32
                        note = primer
source                  1..32
                        mol_type = other DNA
                        organism = synthetic construct
SEQUENCE: 74
catgaatgta atgccttcca agtataggga cg                               32

SEQ ID NO: 75           moltype = DNA  length = 33
FEATURE                 Location/Qualifiers
misc_feature            1..33
                        note = primer
source                  1..33
                        mol_type = other DNA
                        organism = synthetic construct
SEQUENCE: 75
acttggaagg cattacattc atgtggtaga cgg                              33

SEQ ID NO: 76           moltype = DNA  length = 22
FEATURE                 Location/Qualifiers
misc_feature            1..22
                        note = primer
source                  1..22
                        mol_type = other DNA
                        organism = synthetic construct
SEQUENCE: 76
gattttgctg gcgttccagg ag                                          22

SEQ ID NO: 77           moltype = DNA  length = 23
FEATURE                 Location/Qualifiers
misc_feature            1..23
                        note = primer
source                  1..23
                        mol_type = other DNA
                        organism = synthetic construct
SEQUENCE: 77
ctggaacgcc agcaaaatct tgg                                         23

SEQ ID NO: 78           moltype = DNA  length = 23
FEATURE                 Location/Qualifiers
misc_feature            1..23
                        note = primer
source                  1..23
```

-continued

```
                        mol_type = other DNA
                        organism = synthetic construct
SEQUENCE: 78
ccaagatggc gctatggttc cag                                              23

SEQ ID NO: 79           moltype = DNA  length = 25
FEATURE                 Location/Qualifiers
misc_feature            1..25
                        note = primer
source                  1..25
                        mol_type = other DNA
                        organism = synthetic construct
SEQUENCE: 79
ccatagcgcc atcttggttg tagac                                            25

SEQ ID NO: 80           moltype = DNA  length = 27
FEATURE                 Location/Qualifiers
misc_feature            1..27
                        note = primer
source                  1..27
                        mol_type = other DNA
                        organism = synthetic construct
SEQUENCE: 80
cttccagctg gctattccac cagtaag                                          27

SEQ ID NO: 81           moltype = DNA  length = 24
FEATURE                 Location/Qualifiers
misc_feature            1..24
                        note = primer
source                  1..24
                        mol_type = other DNA
                        organism = synthetic construct
SEQUENCE: 81
gtggaatagc cagctggaag gatg                                             24

SEQ ID NO: 82           moltype = DNA  length = 27
FEATURE                 Location/Qualifiers
misc_feature            1..27
                        note = primer
source                  1..27
                        mol_type = other DNA
                        organism = synthetic construct
SEQUENCE: 82
cttccagctc tgtattccac cagtaag                                          27

SEQ ID NO: 83           moltype = DNA  length = 24
FEATURE                 Location/Qualifiers
misc_feature            1..24
                        note = primer
source                  1..24
                        mol_type = other DNA
                        organism = synthetic construct
SEQUENCE: 83
gtggaataca gagctggaag gatg                                             24

SEQ ID NO: 84           moltype = DNA  length = 29
FEATURE                 Location/Qualifiers
misc_feature            1..29
                        note = primer
source                  1..29
                        mol_type = other DNA
                        organism = synthetic construct
SEQUENCE: 84
aagtaatcgg ccttccagct atttattcc                                        29

SEQ ID NO: 85           moltype = DNA  length = 25
FEATURE                 Location/Qualifiers
misc_feature            1..25
                        note = primer
source                  1..25
                        mol_type = other DNA
                        organism = synthetic construct
SEQUENCE: 85
gctggaaggc cgattacttg gatac                                            25

SEQ ID NO: 86           moltype = DNA  length = 23
FEATURE                 Location/Qualifiers
misc_feature            1..23
                        note = primer
```

```
source                  1..23
                        mol_type = other DNA
                        organism = synthetic construct
SEQUENCE: 86
atccaagtag gcatccttcc agc                                           23

SEQ ID NO: 87           moltype = DNA  length = 27
FEATURE                 Location/Qualifiers
misc_feature            1..27
                        note = primer
source                  1..27
                        mol_type = other DNA
                        organism = synthetic construct
SEQUENCE: 87
ggaaggatgc ctacttggat actactc                                       27

SEQ ID NO: 88           moltype = DNA  length = 24
FEATURE                 Location/Qualifiers
misc_feature            1..24
                        note = primer
source                  1..24
                        mol_type = other DNA
                        organism = synthetic construct
SEQUENCE: 88
gatcaacggc agacactgga tgag                                          24

SEQ ID NO: 89           moltype = DNA  length = 24
FEATURE                 Location/Qualifiers
misc_feature            1..24
                        note = primer
source                  1..24
                        mol_type = other DNA
                        organism = synthetic construct
SEQUENCE: 89
cagtgtctgc cgttgatctt gcac                                          24

SEQ ID NO: 90           moltype = DNA  length = 29
FEATURE                 Location/Qualifiers
misc_feature            1..29
                        note = primer
source                  1..29
                        mol_type = other DNA
                        organism = synthetic construct
SEQUENCE: 90
tctgatgttg gtcttgcact gaccggacc                                     29

SEQ ID NO: 91           moltype = DNA  length = 32
FEATURE                 Location/Qualifiers
misc_feature            1..32
                        note = primer
source                  1..32
                        mol_type = other DNA
                        organism = synthetic construct
SEQUENCE: 91
cagtgcaaga ccaacatcag acactggatg ag                                 32

SEQ ID NO: 92           moltype = DNA  length = 25
FEATURE                 Location/Qualifiers
misc_feature            1..25
                        note = primer
source                  1..25
                        mol_type = other DNA
                        organism = synthetic construct
SEQUENCE: 92
cttgttttgg gaggtccatg tccac                                         25

SEQ ID NO: 93           moltype = DNA  length = 26
FEATURE                 Location/Qualifiers
misc_feature            1..26
                        note = primer
source                  1..26
                        mol_type = other DNA
                        organism = synthetic construct
SEQUENCE: 93
catggacctc ccaaaacaag agtaac                                        26

SEQ ID NO: 94           moltype = DNA  length = 26
FEATURE                 Location/Qualifiers
misc_feature            1..26
```

```
                        note = primer
source                  1..26
                        mol_type = other DNA
                        organism = synthetic construct
SEQUENCE: 94
gcatagtggc catgcaccct gcgttg                                        26

SEQ ID NO: 95           moltype = DNA  length = 33
FEATURE                 Location/Qualifiers
misc_feature            1..33
                        note = primer
source                  1..33
                        mol_type = other DNA
                        organism = synthetic construct
SEQUENCE: 95
ggtgcatggc cactatgcat aaagatacaa acc                                33

SEQ ID NO: 96           moltype = DNA  length = 25
FEATURE                 Location/Qualifiers
misc_feature            1..25
                        note = primer
source                  1..25
                        mol_type = other DNA
                        organism = synthetic construct
SEQUENCE: 96
cccggtggta ggtgatgcct tgggg                                         25

SEQ ID NO: 97           moltype = DNA  length = 25
FEATURE                 Location/Qualifiers
misc_feature            1..25
                        note = primer
source                  1..25
                        mol_type = other DNA
                        organism = synthetic construct
SEQUENCE: 97
catcacctac caccgggaat gtccc                                         25

SEQ ID NO: 98           moltype = DNA  length = 29
FEATURE                 Location/Qualifiers
misc_feature            1..29
                        note = primer
source                  1..29
                        mol_type = other DNA
                        organism = synthetic construct
SEQUENCE: 98
gaatgtccca ataatagccg ttggagggt                                     29

SEQ ID NO: 99           moltype = DNA  length = 27
FEATURE                 Location/Qualifiers
misc_feature            1..27
                        note = primer
source                  1..27
                        mol_type = other DNA
                        organism = synthetic construct
SEQUENCE: 99
acggctatta ttgggacatt cccggtg                                       27

SEQ ID NO: 100          moltype = DNA  length = 31
FEATURE                 Location/Qualifiers
misc_feature            1..31
                        note = primer
source                  1..31
                        mol_type = other DNA
                        organism = synthetic construct
SEQUENCE: 100
caatgtgact ccttgctgaa gcaacaagag c                                  31

SEQ ID NO: 101          moltype = DNA  length = 35
FEATURE                 Location/Qualifiers
misc_feature            1..35
                        note = primer
source                  1..35
                        mol_type = other DNA
                        organism = synthetic construct
SEQUENCE: 101
cttcagcaag gagtcacatt gaaatatctc agcag                              35

SEQ ID NO: 102          moltype = DNA  length = 37
FEATURE                 Location/Qualifiers
```

-continued

```
misc_feature           1..37
                       note = primer
source                 1..37
                       mol_type = other DNA
                       organism = synthetic construct
SEQUENCE: 102
cctgctgaga tattttaatg tgactttttg ctgaagc                             37

SEQ ID NO: 103         moltype = DNA  length = 30
FEATURE                Location/Qualifiers
misc_feature           1..30
                       note = primer
source                 1..30
                       mol_type = other DNA
                       organism = synthetic construct
SEQUENCE: 103
caatgtgact ttttgctgaa gcaacaagag                                     30

SEQ ID NO: 104         moltype = DNA  length = 35
FEATURE                Location/Qualifiers
misc_feature           1..35
                       note = primer
source                 1..35
                       mol_type = other DNA
                       organism = synthetic construct
SEQUENCE: 104
cttcagcaaa aagtcacatt gaaatatctc agcag                               35

SEQ ID NO: 105         moltype = DNA  length = 37
FEATURE                Location/Qualifiers
misc_feature           1..37
                       note = primer
source                 1..37
                       mol_type = other DNA
                       organism = synthetic construct
SEQUENCE: 105
cctgctgaga tattttaatg tgaccttttg ctgaagc                             37

SEQ ID NO: 106         moltype = DNA  length = 32
FEATURE                Location/Qualifiers
misc_feature           1..32
                       note = primer
source                 1..32
                       mol_type = other DNA
                       organism = synthetic construct
SEQUENCE: 106
gtcacattaa aatatctcag caggatttga ac                                  32

SEQ ID NO: 107         moltype = DNA  length = 29
FEATURE                Location/Qualifiers
misc_feature           1..29
                       note = primer
source                 1..29
                       mol_type = other DNA
                       organism = synthetic construct
SEQUENCE: 107
cgttcaaatc gttctgagat atttcaatg                                      29

SEQ ID NO: 108         moltype = DNA  length = 29
FEATURE                Location/Qualifiers
misc_feature           1..29
                       note = primer
source                 1..29
                       mol_type = other DNA
                       organism = synthetic construct
SEQUENCE: 108
gaaatatctc agaacgattt gaacgctac                                      29

SEQ ID NO: 109         moltype = DNA  length = 20
FEATURE                Location/Qualifiers
misc_feature           1..20
                       note = primer
source                 1..20
                       mol_type = other DNA
                       organism = synthetic construct
SEQUENCE: 109
agggtggaga tgtagcgttc                                                20

SEQ ID NO: 110         moltype = DNA  length = 21
```

```
FEATURE                Location/Qualifiers
misc_feature           1..21
                       note = primer
source                 1..21
                       mol_type = other DNA
                       organism = synthetic construct
SEQUENCE: 110
cgctacatct ccacccttgc c                                              21

SEQ ID NO: 111         moltype = DNA  length = 17
FEATURE                Location/Qualifiers
misc_feature           1..17
                       note = primer
source                 1..17
                       mol_type = other DNA
                       organism = synthetic construct
SEQUENCE: 111
cccccagcgc ccactgc                                                   17

SEQ ID NO: 112         moltype = DNA  length = 18
FEATURE                Location/Qualifiers
misc_feature           1..18
                       note = primer
source                 1..18
                       mol_type = other DNA
                       organism = synthetic construct
SEQUENCE: 112
acccacagcg cccactgc                                                  18

SEQ ID NO: 113         moltype = DNA  length = 20
FEATURE                Location/Qualifiers
misc_feature           1..20
                       note = primer
source                 1..20
                       mol_type = other DNA
                       organism = synthetic construct
SEQUENCE: 113
gtgggcgctg tgggttacag                                                20

SEQ ID NO: 114         moltype = DNA  length = 19
FEATURE                Location/Qualifiers
misc_feature           1..19
                       note = primer
source                 1..19
                       mol_type = other DNA
                       organism = synthetic construct
SEQUENCE: 114
gtgggcgctg ggggttaca                                                 19

SEQ ID NO: 115         moltype = DNA  length = 23
FEATURE                Location/Qualifiers
misc_feature           1..23
                       note = primer
source                 1..23
                       mol_type = other DNA
                       organism = synthetic construct
SEQUENCE: 115
gtaaccccca ctgcccactg cgc                                            23

SEQ ID NO: 116         moltype = DNA  length = 30
FEATURE                Location/Qualifiers
misc_feature           1..30
                       note = primer
source                 1..30
                       mol_type = other DNA
                       organism = synthetic construct
SEQUENCE: 116
gggcagtggg ggttacagcc aaataaaatc                                     30

SEQ ID NO: 117         moltype = DNA  length = 23
FEATURE                Location/Qualifiers
misc_feature           1..23
                       note = primer
source                 1..23
                       mol_type = other DNA
                       organism = synthetic construct
SEQUENCE: 117
tatttgggcg taacccacac tgc                                            23
```

-continued

```
SEQ ID NO: 118         moltype = DNA  length = 28
FEATURE                Location/Qualifiers
misc_feature           1..28
                       note = primer
source                 1..28
                       mol_type = other DNA
                       organism = synthetic construct
SEQUENCE: 118
gtgggttacg cccaaataaa atcactta                                       28

SEQ ID NO: 119         moltype = DNA  length = 20
FEATURE                Location/Qualifiers
misc_feature           1..20
                       note = primer
source                 1..20
                       mol_type = other DNA
                       organism = synthetic construct
SEQUENCE: 119
ttggctggca cccacactgc                                                20

SEQ ID NO: 120         moltype = DNA  length = 25
FEATURE                Location/Qualifiers
misc_feature           1..25
                       note = primer
source                 1..25
                       mol_type = other DNA
                       organism = synthetic construct
SEQUENCE: 120
gtgggtgcca gccaaataaa atcac                                          25

SEQ ID NO: 121         moltype = DNA  length = 19
FEATURE                Location/Qualifiers
misc_feature           1..19
                       note = primer
source                 1..19
                       mol_type = other DNA
                       organism = synthetic construct
SEQUENCE: 121
tggctggcac ccccactgc                                                 19

SEQ ID NO: 122         moltype = DNA  length = 23
FEATURE                Location/Qualifiers
misc_feature           1..23
                       note = primer
source                 1..23
                       mol_type = other DNA
                       organism = synthetic construct
SEQUENCE: 122
gggggtgcca gccaaataaa atc                                            23

SEQ ID NO: 123         moltype = DNA  length = 21
FEATURE                Location/Qualifiers
misc_feature           1..21
                       note = primer
source                 1..21
                       mol_type = other DNA
                       organism = synthetic construct
SEQUENCE: 123
tttgggcgta acccccactg c                                              21

SEQ ID NO: 124         moltype = DNA  length = 25
FEATURE                Location/Qualifiers
misc_feature           1..25
                       note = primer
source                 1..25
                       mol_type = other DNA
                       organism = synthetic construct
SEQUENCE: 124
gggggttacg cccaaataaa atcac                                          25

SEQ ID NO: 125         moltype = DNA  length = 29
FEATURE                Location/Qualifiers
misc_feature           1..29
                       note = primer
source                 1..29
                       mol_type = other DNA
                       organism = synthetic construct
SEQUENCE: 125
cccatttgtc gttgggggag gatctaaag                                      29
```

```
SEQ ID NO: 126          moltype = DNA  length = 26
FEATURE                 Location/Qualifiers
misc_feature            1..26
                        note = primer
source                  1..26
                        mol_type = other DNA
                        organism = synthetic construct
SEQUENCE: 126
ccccaacgac aaatgggcag acgggc                                        26

SEQ ID NO: 127          moltype = DNA  length = 26
FEATURE                 Location/Qualifiers
misc_feature            1..26
                        note = primer
source                  1..26
                        mol_type = other DNA
                        organism = synthetic construct
SEQUENCE: 127
gcaaattgct agacattgca gttttg                                        26

SEQ ID NO: 128          moltype = DNA  length = 24
FEATURE                 Location/Qualifiers
misc_feature            1..24
                        note = primer
source                  1..24
                        mol_type = other DNA
                        organism = synthetic construct
SEQUENCE: 128
ctgcaatgtc tagcaatttg cagc                                          24

SEQ ID NO: 129          moltype = DNA  length = 29
FEATURE                 Location/Qualifiers
misc_feature            1..29
                        note = primer
source                  1..29
                        mol_type = other DNA
                        organism = synthetic construct
SEQUENCE: 129
cccatttgtc gttgggggag gatctaaag                                     29

SEQ ID NO: 130          moltype = DNA  length = 26
FEATURE                 Location/Qualifiers
misc_feature            1..26
                        note = primer
source                  1..26
                        mol_type = other DNA
                        organism = synthetic construct
SEQUENCE: 130
ccccaacgac aaatgggcag acgggc                                        26

SEQ ID NO: 131          moltype = DNA  length = 27
FEATURE                 Location/Qualifiers
misc_feature            1..27
                        note = primer
source                  1..27
                        mol_type = other DNA
                        organism = synthetic construct
SEQUENCE: 131
caacttatgg gcttgggcat aaggatg                                       27

SEQ ID NO: 132          moltype = DNA  length = 28
FEATURE                 Location/Qualifiers
misc_feature            1..28
                        note = primer
source                  1..28
                        mol_type = other DNA
                        organism = synthetic construct
SEQUENCE: 132
cttatgccca agcccataag ttggtttc                                      28

SEQ ID NO: 133          moltype = DNA  length = 27
FEATURE                 Location/Qualifiers
misc_feature            1..27
                        note = primer
source                  1..27
                        mol_type = other DNA
                        organism = synthetic construct
SEQUENCE: 133
```

```
caacttatgc cattgggcat aaggatg                                    27

SEQ ID NO: 134          moltype = DNA  length = 28
FEATURE                 Location/Qualifiers
misc_feature            1..28
                        note = primer
source                  1..28
                        mol_type = other DNA
                        organism = synthetic construct
SEQUENCE: 134
cttatgccca atggcataag ttggtttc                                   28

SEQ ID NO: 135          moltype = DNA  length = 27
FEATURE                 Location/Qualifiers
misc_feature            1..27
                        note = primer
source                  1..27
                        mol_type = other DNA
                        organism = synthetic construct
SEQUENCE: 135
caacttatgg tattgggcat aaggatg                                    27

SEQ ID NO: 136          moltype = DNA  length = 28
FEATURE                 Location/Qualifiers
misc_feature            1..28
                        note = primer
source                  1..28
                        mol_type = other DNA
                        organism = synthetic construct
SEQUENCE: 136
cttatgccca ataccataag ttggtttc                                   28

SEQ ID NO: 137          moltype = DNA  length = 22
FEATURE                 Location/Qualifiers
misc_feature            1..22
                        note = primer
source                  1..22
                        mol_type = other DNA
                        organism = synthetic construct
SEQUENCE: 137
gaaaccaagg catggtgttg gg                                         22

SEQ ID NO: 138          moltype = DNA  length = 23
FEATURE                 Location/Qualifiers
misc_feature            1..23
                        note = primer
source                  1..23
                        mol_type = other DNA
                        organism = synthetic construct
SEQUENCE: 138
aacaccatgc cttggtttcc gtc                                        23

SEQ ID NO: 139          moltype = DNA  length = 31
FEATURE                 Location/Qualifiers
misc_feature            1..31
                        note = primer
source                  1..31
                        mol_type = other DNA
                        organism = synthetic construct
SEQUENCE: 139
cgatataaaa tgcggatgag tcgacggaaa c                               31

SEQ ID NO: 140          moltype = DNA  length = 39
FEATURE                 Location/Qualifiers
misc_feature            1..39
                        note = primer
source                  1..39
                        mol_type = other DNA
                        organism = synthetic construct
SEQUENCE: 140
gactcatccg cattttatat cggttcaaaa aatttgtac                       39

SEQ ID NO: 141          moltype = DNA  length = 24
FEATURE                 Location/Qualifiers
misc_feature            1..24
                        note = primer
source                  1..24
                        mol_type = other DNA
                        organism = synthetic construct
```

```
SEQUENCE: 141
gatgggtaca aggcttttga accg                                           24

SEQ ID NO: 142          moltype = DNA  length = 25
FEATURE                 Location/Qualifiers
misc_feature            1..25
                        note = primer
source                  1..25
                        mol_type = other DNA
                        organism = synthetic construct
SEQUENCE: 142
gttcaaaagc cttgtaccca tcctg                                          25

SEQ ID NO: 143          moltype = DNA  length = 26
FEATURE                 Location/Qualifiers
misc_feature            1..26
                        note = primer
source                  1..26
                        mol_type = other DNA
                        organism = synthetic construct
SEQUENCE: 143
ccaggatggg aacaaatttt ttgaac                                         26

SEQ ID NO: 144          moltype = DNA  length = 26
FEATURE                 Location/Qualifiers
misc_feature            1..26
                        note = primer
source                  1..26
                        mol_type = other DNA
                        organism = synthetic construct
SEQUENCE: 144
caaaaaattt gttcccatcc tggctg                                         26

SEQ ID NO: 145          moltype = DNA  length = 27
FEATURE                 Location/Qualifiers
misc_feature            1..27
                        note = primer
source                  1..27
                        mol_type = other DNA
                        organism = synthetic construct
SEQUENCE: 145
caatttggcc tccagttgct tggcagc                                        27

SEQ ID NO: 146          moltype = DNA  length = 29
FEATURE                 Location/Qualifiers
misc_feature            1..29
                        note = primer
source                  1..29
                        mol_type = other DNA
                        organism = synthetic construct
SEQUENCE: 146
gcaactggag gccaaattgc ttgaccctc                                      29

SEQ ID NO: 147          moltype = DNA  length = 30
FEATURE                 Location/Qualifiers
misc_feature            1..30
                        note = primer
source                  1..30
                        mol_type = other DNA
                        organism = synthetic construct
SEQUENCE: 147
agcaactggg tgccaaattg cttgaccctc                                     30

SEQ ID NO: 148          moltype = DNA  length = 27
FEATURE                 Location/Qualifiers
misc_feature            1..27
                        note = primer
source                  1..27
                        mol_type = other DNA
                        organism = synthetic construct
SEQUENCE: 148
caatttggca cccagttgct tggcagc                                        27

SEQ ID NO: 149          moltype = DNA  length = 31
FEATURE                 Location/Qualifiers
misc_feature            1..31
                        note = primer
source                  1..31
                        mol_type = other DNA
```

-continued

```
                       organism = synthetic construct
SEQUENCE: 149
gtaatccact attgcagtct cctgtgagta c                                31

SEQ ID NO: 150         moltype = DNA  length = 32
FEATURE                Location/Qualifiers
misc_feature           1..32
                       note = primer
source                 1..32
                       mol_type = other DNA
                       organism = synthetic construct
SEQUENCE: 150
gagactgcaa tagtggatta cgcaagagga at                               32

SEQ ID NO: 151         moltype = DNA  length = 18
FEATURE                Location/Qualifiers
misc_feature           1..18
                       note = primer
source                 1..18
                       mol_type = other DNA
                       organism = synthetic construct
SEQUENCE: 151
cgccccaaga tcctgggg                                               18

SEQ ID NO: 152         moltype = DNA  length = 19
FEATURE                Location/Qualifiers
misc_feature           1..19
                       note = primer
source                 1..19
                       mol_type = other DNA
                       organism = synthetic construct
SEQUENCE: 152
ccaggatctt ggggcgatg                                              19

SEQ ID NO: 153         moltype = DNA  length = 35
FEATURE                Location/Qualifiers
misc_feature           1..35
                       note = primer
source                 1..35
                       mol_type = other DNA
                       organism = synthetic construct
SEQUENCE: 153
gatgatagat gcgttgacag agttgggaca aaaag                            35

SEQ ID NO: 154         moltype = DNA  length = 35
FEATURE                Location/Qualifiers
misc_feature           1..35
                       note = primer
source                 1..35
                       mol_type = other DNA
                       organism = synthetic construct
SEQUENCE: 154
tctgtcaacg catctatcat cgccccaaca tcctg                            35

SEQ ID NO: 155         moltype = DNA  length = 32
FEATURE                Location/Qualifiers
misc_feature           1..32
                       note = primer
source                 1..32
                       mol_type = other DNA
                       organism = synthetic construct
SEQUENCE: 155
gtcagaattc agcgttggag attcctcttg cg                               32
```

ENGINEERED PHOSPHOLIPASE D MUTANTS, METHODS OF MAKING ENGINEERED PHOSPHOLIPASE D MUTANTS, AND USES THEREOF

CROSS REFERENCE TO RELATED APPLICATIONS

This application claims the benefit of U.S. Provisional Patent Application No. 63/286,447, filed Dec. 6, 2021, the contents of which is incorporated herein by reference in its entirety.

STATEMENT REGARDING FEDERALLY SPONSORED RESEARCH OR DEVELOPMENT

The contents of this disclosure were made with government support under Grant No. CHE-1749919, awarded by the National Science Foundation. The government has certain rights in the invention.

INCORPORATION BY REFERENCE OF SEQUENCE LISTING

The Sequence Listing in an XML file, named 40314_9941-03-US_SequenceListing.xml of 224 KB, created on Jun. 4, 2024, and submitted to the United States Patent and Trademark Office via Patent Center, is incorporated herein by reference.

BACKGROUND

Cellular membranes have myriad functions, ranging from being selectively permeable barriers to platforms for initiating signaling pathways. Though membranes contain hydrophobic proteins and glycoconjugates, by far their most abundant constituents are lipids. Understanding how each individual lipid constituent contributes to specific properties and functions of membranes remains a major challenge in membrane biology, one that requires tools for altering the lipid content of endogenous membranes with high molecular and spatiotemporal precision. Akin to how single amino acid substitutions via site-directed mutagenesis or amber suppression have transformed our ability to perform structure-function relationships within the proteome controllable lipid-modifying enzymes can serve as "membrane editors" to enable the selective manipulation of individual lipid species within membranes.

This strategy has seen the most success with the phosphoinositides, a family of phosphorylated derivatives of phosphatidylinositol, where chemical- or light-induced proximity has been harnessed to create a suite of tools for rapid phosphorylation/dephosphorylation of the inositol head group in situ. Though critically important for many signaling pathways, phosphoinositides are rare lipids, and similar tools for membrane editing beyond this tiny sector of the lipidome are scant. Phosphatidylcholine (PC) is the most abundant lipid within cellular membranes, and it could serve as a substrate for a general membrane editor capable of replacing the choline head group with natural and unnatural head groups to create a wide array of desired phospholipids on demand.

Phospholipase D (PLD) catalyzes hydrolysis of PC to form a signaling lipid, phosphatidic acid (PA), and it can also catalyze transphosphatidylation with exogenous alcohols to swap out head groups to form a variety of natural and unnatural phospholipids. Though mammalian cells have endogenous PLD enzymes, they are dispensable for viability and exhibit low levels of basal activity. A microbial PLD has been previously identified that possesses hydrolysis and transphosphatidylation activities in mammalian cells and is amenable to light-mediated control of its localization and activity. However, the activity of this PLD in mammalian cells is modest, owing to its acidic pH maximum and multiple disulfide bonds, limiting its utility to circumstances where very low levels of PA formed by hydrolysis are sufficient to induce a signaling outcome.

Directed enzyme evolution is typically performed as an iteration of two basic steps that mimic natural selection: random or targeted mutagenesis of a gene to generate a library of variants and identification of rare variants that exhibit a desired function through selection or screening. Where feasible, selection is preferred to screening, to increase throughput. In vivo selections are typically performed using *E. coli* or *S. cerevisiae* as host cells, even when the evolved enzyme is ultimately intended for use in mammalian cells. However, this approach can be problematic for lipid-modifying enzymes, as their substrates are components of membranes, whose compositions and properties differ substantially between bacteria, fungi, and higher eukaryotes.

BRIEF SUMMARY OF THE DISCLOSURE

The present disclosure is directed to (i) engineered phospholipase D (PLD) enzymes with substantially higher catalytic activity, greater stability, and broader substrate scope than wild type PLD, and (ii) a process by which such enzymes can be generated. The engineered PLD enzymes disclosed herein are useful for the in vitro and in vivo (e.g., in mammalian cells) chemoenzymatic synthesis of a large collection of natural and non-natural phospholipids via transphosphatidylation reactions between phosphatidylcholine and either primary or secondary alcohol substrates.

In a first aspect, the present disclosure is directed to a mutant Phospholipase D (PLD) enzyme comprising an amino acid sequence that varies from the amino acid sequence of a wild type PLD enzyme as set forth in SEQ ID NO: 1 in at least 6 to 10 substitutions; wherein one of the substitutions is G381V; wherein the additional substitutions are selected from the group consisting of S3T, Q13H, K34R, P42L, P42S, P42T, K57R, A59V, M71I, I130M, K133R, F163L, S185G, S198F, D201G, D201N, F235L, G242V, P245A, H248Y, K249R, A258T, P263S, V264I, K275R, K327R, G328S, E331K, N338Y, P345S, T395I, G406S, T412N, G429D, Q439K, T450A, D480G, D480E, Q492R, A495V, T496I, and C504Y; and wherein the mutant PLD enzyme exhibits a transphosphatidylation activity at least 2-fold higher as compared to the wild type PLD enzyme. One embodiment of the disclosure is directed to a mutant PLD enzyme wherein the mutant PLD enzyme exhibits a transphosphatidylation activity at least 10-fold higher as compared to the wild type PLD enzyme. In one embodiment, the mutant PLD enzyme comprises an additional substitution of A258T. In one embodiment, the mutant PLD enzyme comprises an additional substitution of G429D. In one embodiment, the mutant PLD enzyme comprises an additional substitution of T450A. One embodiment of the disclosure is directed to a mutant PLD enzyme comprising the substitutions of G381V, K57R, A59V, K109R, P245A, V264I, G328S, G406S, and G429D. One embodiment of the disclosure is directed to a mutant PLD enzyme comprising the substitutions of G381V, I130M, P245A, G328S, G406S, and G429D. In one embodiment, the mutant PLD enzyme exhibits a transphosphatidylation activity at least 10-fold higher as compared to the wild type PLD enzyme, wherein the transphosphatidylation activity is measured in cells. In one embodiment, the mutant PLD enzyme exhibits a transphosphatidylation activity of about 30-fold to 125-fold higher as compared to the wild type PLD enzyme. In one embodiment, the mutant PLD enzyme exhibits a transphosphatidylation activity of about 50-fold to 110-fold higher as compared to the wild type PLD enzyme. In one embodiment, the mutant PLD enzyme exhibits a transphosphatidylation activity of about 100-fold higher as compared to the wild type PLD enzyme. In some embodiments, the mutant PLD enzyme exhibits an activity of hydrolysis of phosphatidylcholine to phosphatidic acid that is at least 10-fold higher as compared to the wild type PLD enzyme when the hydrolysis activity is measured in vitro. In some embodiments, the mutant PLD enzyme exhibits an activity of hydrolysis of phosphatidylcholine to phosphatidic acid that is about 10-fold to 50-fold higher as compared to the wild type PLD enzyme as measured in vitro.

In some embodiments, the mutant PLD enzyme exhibits an activity of hydrolysis of phosphatidylcholine to phosphatidic acid that is about 30-fold higher as compared to the wild type PLD enzyme as measured in vitro. In some embodiments, the mutant PLD enzyme exhibits an activity of hydrolysis of phosphatidylcholine to phosphatidic acid that is at least 10-fold higher as compared to the wild type PLD enzyme when the hydrolysis activity is measured in cells. In some embodiments, the mutant PLD enzyme exhibits an activity of hydrolysis of phosphatidylcholine to phosphatidic acid that is about 10-fold to 50-fold higher as compared to the wild type PLD enzyme as measured in cells. In some embodiments, the mutant PLD enzyme exhibits an activity of hydrolysis of phosphatidylcholine to phosphatidic acid that is about 30-fold higher as compared to the wild type PLD enzyme as measured in cells.

One aspect of the disclosure is directed to an isolated nucleic acid encoding a mutant PLD enzyme comprising an amino acid sequence that varies from the amino acid sequence of a wild type PLD enzyme as set forth in SEQ ID NO: 1 in at least 6 to 10 substitutions; wherein one of the substitutions is G381V; wherein the additional substitutions are selected from the group consisting of S3T, Q13H, K34R, P42L, P42S, P42T, K57R, A59V, M71I, I130M, K133R, F163L, S185G, S198F, D201G, D201N, F235L, G242V, P245A, H248Y, K249R, A258T, P263S, V264I, K275R, K327R, G328S, E331K, N338Y, P345S, T395I, G406S, T412N, G429D, Q439K, T450A, D480G, D480E, Q492R, A495V, T496I, and C504Y; and wherein the mutant PLD enzyme exhibits a transphosphatidylation activity at least 2-fold higher as compared to the wild type PLD enzyme.

One aspect of the disclosure is directed to an expression vector comprising an isolated nucleic acid encoding a mutant PLD enzyme comprising an amino acid sequence that varies from the amino acid sequence of a wild type PLD enzyme as set forth in SEQ ID NO: 1 in at least 6 to 10 substitutions; wherein one of the substitutions is G381V; wherein the additional substitutions are selected from the group consisting of S3T, Q13H, K34R, P42L, P42S, P42T, K57R, A59V, M71I, I130M, K133R, F163L, S185G, S198F, D201G, D201N, F235L, G242V, P245A, H248Y, K249R, A258T, P263S, V264I, K275R, K327R, G328S, E331K, N338Y, P345S, T395I, G406S, T412N, G429D, Q439K, T450A, D480G, D480E, Q492R, A495V, T496I, and C504Y; and wherein the mutant PLD enzyme exhibits a transphosphatidylation activity at least 2-fold higher as compared to the wild type PLD enzyme.

One aspect of the disclosure is directed to a host cell comprising an expression vector comprising an isolated nucleic acid encoding a mutant PLD enzyme comprising an amino acid sequence that varies from the amino acid sequence of a wild type PLD enzyme as set forth in SEQ ID NO: 1 in at least 6 to 10 substitutions; wherein one of the substitutions is G381V; wherein the additional substitutions are selected from the group consisting of S3T, Q13H, K34R, P42L, P42S, P42T, K57R, A59V, M71I, I130M, K133R, F163L, S185G, S198F, D201G, D201N, F235L, G242V, P245A, H248Y, K249R, A258T, P263S, V264I, K275R, K327R, G328S, E331K, N338Y, P345S, T395I, G406S, T412N, G429D, Q439K, T450A, D480G, D480E, Q492R, A495V, T496I, and C504Y; and wherein the mutant PLD enzyme exhibits a transphosphatidylation activity at least 2-fold higher as compared to the wild type PLD enzyme. In one embodiment, the host cell is an HEK293T cell.

Another aspect of the disclosure is directed to a method of using a mutant PLD enzyme as a catalyst for synthesis of phospholipids. In some embodiments, the method uses a mutant PLD enzyme disclosed herein as a catalyst for synthesis of phospholipids in vitro, where the method comprises synthesizing phospholipids from phosphatidylcholine and an alcohol substrate using a mutant PLD enzyme, where the phospholipid head of the phosphatidylcholine is replaced to form a natural or unnatural phosphatidyl alcohol. In one embodiment, the unnatural phosphatidyl alcohol comprises a reactive polar head and is synthesized with high selectivity and high yield. In one embodiment, the reactive polar head comprises an azide, an alkyne, or trans-cyclooctene alcohols. In one embodiment, the phosphatidyl alcohol synthesized comprises dioleoyl phosphatidyl alcohol (DOPAlc), dioleoyl phosphatidic acid (DOPA), dipalmitoyl phosphatidyl alcohol (DPPA). In some embodiments, the method uses a mutant PLD enzyme disclosed herein as a catalyst for synthesis of phospholipids in a mammalian cell, where the method comprises providing a mammalian cell with one or more alcohol substrates, wherein the mammalian cell expresses the mutant PLD enzyme and displays phosphatidylcholine on the cell membrane; and permitting the mutant PLD enzyme to replace the phospholipid head of the phosphatidylcholine with an alcohol substrate to form a natural or unnatural phosphatidyl alcohol, thereby making phospholipids.

One aspect of the disclosure is directed to a method of using a mutant PLD enzyme to modulate phosphatidic acid (PA)-dependent Hippo growth restriction pathway, the method comprising increasing the PA made at the plasma membrane using a mutant PLD enzyme disclosed herein, wherein the PA attenuates Hippo growth restriction pathway by triggering translocation of Yes-associated protein (YAP) from the cytosol to the nucleus in serum-starved cells.

One aspect of the disclosure is directed to a method of using a mutant PLD enzyme to modulate PA-dependent AMP-activated protein kinase (AMPK) signaling, the method comprising synthesizing PA made at cellular membranes using a mutant PLD disclosed herein, wherein the PA induces liver kinase B1 (LKB1) translocation to PA-rich membranes, leading to an increase of AMPK phosphorylation.

One aspect of the disclosure is directed to a method of using a mutant PLD enzyme to modulate PA-dependent mammalian target of rapamycin (mTOR) signaling, the method comprising treating cells expressing plasma membrane-targeted optoPLD with an AMPK inhibitor followed by using a mutant PLD enzyme disclosed herein; wherein the mutant PLD enzyme increases phosphorylation of the mTOR effector S6 kinase.

Another aspect of the disclosure is directed to a method of identifying a nucleic acid encoding a mutant PLD that exhibits a transphosphatidylation activity at least 10-fold higher in mammalian cells as compared to a wild type PLD enzyme which comprises the amino acid sequence of SEQ ID NO: 1, the method comprising:

a) generating a mutant PLD library which comprises nucleic acids encoding mutant PLD enzymes;

b) introducing the library to cells of a mammalian cell line and expressing the mutant PLD enzymes from the library in the cells;

c) labeling the cells expressing mutant PLD enzymes based on the transphosphatidylation activities of the mutant PLD enzymes; and d) identifying and recovering cells expressing a mutant PLD enzyme that exhibits a transphosphatidylation activity at least 10-fold higher in mammalian cells as compared to the wild type PLD enzyme.

One embodiment of the disclosure is directed to a method of identifying a nucleic acid encoding a mutant PLD that exhibits a transphosphatidylation activity at least 10-fold higher in mammalian cells as compared to a wild type PLD enzyme which comprises the amino acid sequence of SEQ ID NO: 1, wherein step c) comprises labeling the cells expressing the mutant PLD enzymes through activity-based fluorescent labeling. In one embodiment, the activity-based fluorescent labeling is a bioorthogonal labeling method. In one embodiment, the bioorthogonal labeling method is Imaging PLD Activity with Clickable Alcohols via Transphosphatidylation (IMPACT). In one embodiment, step d) is performed by fluorescence activated cell sorting (FACS). One embodiment further comprises extracting DNA from the recovered cells to recover nucleic acids encoding the mutant PLD enzymes. One embodiment further comprises introducing the recovered nucleic acids to cells of a mammalian cell line and expressing the mutant PLD enzymes from the recovered nucleic acids in the cells; labeling the cells expressing mutant PLD enzymes based on the transphosphatidylation activities of the mutant PLD enzymes; and identifying and recovering cells expressing a mutant PLD enzyme that exhibits a transphosphatidylation activity in mammalian cells at least 10-fold higher as compared to the wild type PLD enzyme.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
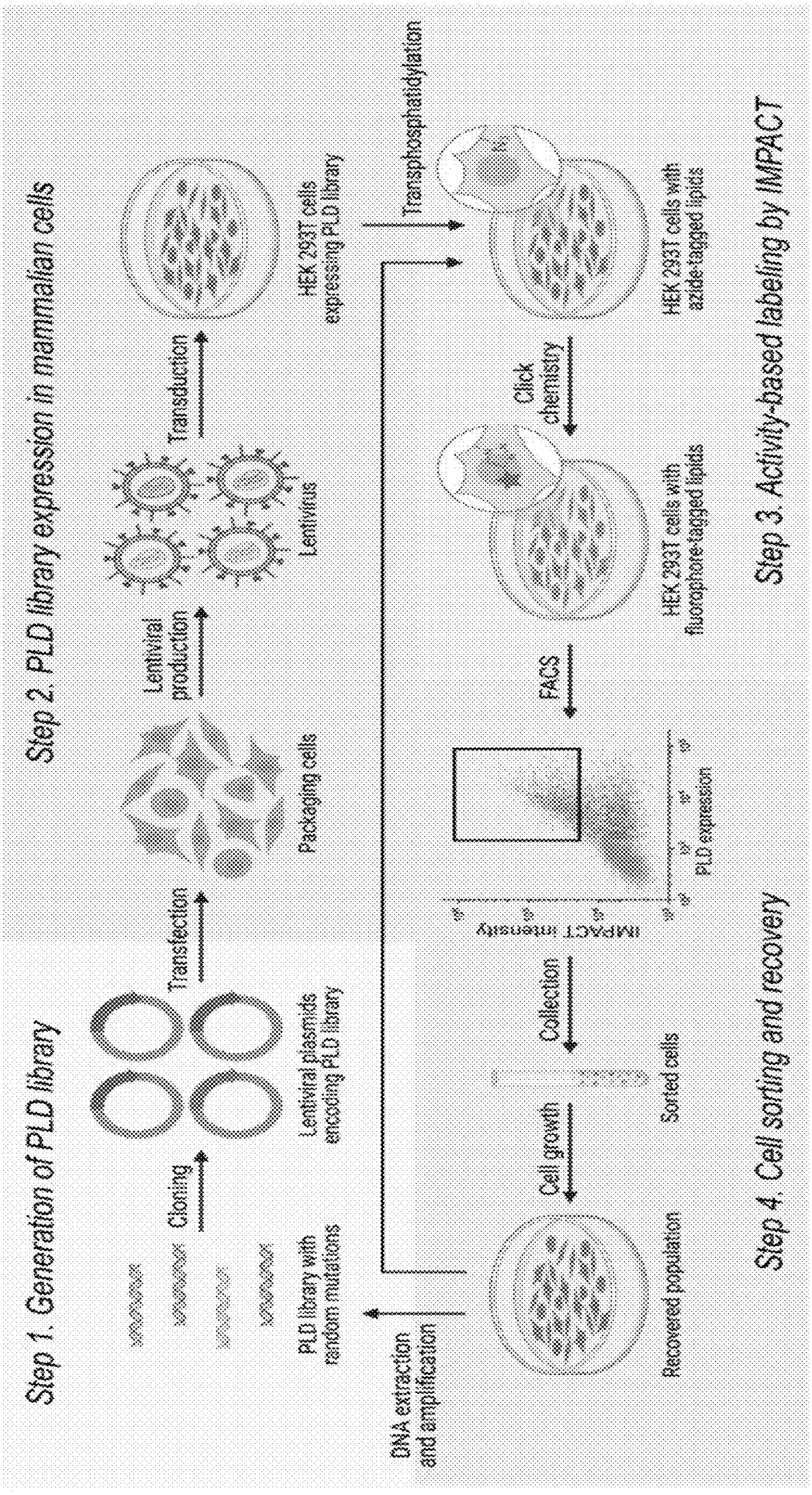
FIG. 1. Design of an activity-dependent directed enzyme evolution strategy to create a phospholipase D (PLD)-based membrane editor in mammalian cells. Step 1: PLDs with random mutations are generated by error-prone PCR and inserted into a lentiviral optoPLD plasmid. Step 2: Packaging cells are transfected with the lentiviral plasmids to produce lentivirus encoding the optoPLD library, which is then transduced into HEK 293T cells. Step 3: Cells expressing the optoPLD library are labeled with IMPACT to fluorescently tag cellular membranes based on the catalytic activity of PLD. Step 4: Cells with high IMPACT labeling intensity are isolated by FACS, expanded, and then either the labeling is repeated to better enrich IMPACT-high cells or DNA is extracted and amplified for further rounds of evolution or clonal isolation and sequencing.

Black horizontal lines indicate mean and vertical error lines indicate standard deviation (n=30-40). PLDdead; a catalytically dead PLD bearing the H167A mutation, PLDWT; wild-type PLD, superPLDx10; superPLD mutant clone 1-4, superPLDx30; superPLD mutant clone 1-12. Scale bar: 10 μm.

FIG. 5A-E. Characterization of superPLD activity in cells. A-B), Quantification of substrate conversion by superPLD in cells. HEK 293T cells expressing plasma membrane-targeted optoPLD (superPLDx30) were treated with 0.5-2% ethanol (Et) for 30 min with intermittent blue light illumination. As a control, cells expressing PLDdead were treated with 2% ethanol accordingly. The relative levels of the most abundant PLD substrate (16:0/18:1 PC; POPC) and its transphosphatidylation product (16:0/18:1 PEt; POPEt) were quantified by LC-MS. Relative PC levels compared to PC levels in control samples (PLDdead-expressing cells) (A) and relative PEt levels compared to PC levels (B) are plotted. Horizontal lines indicate average, and vertical error bars indicate standard deviation (n=4-6). C-D) Confocal microscopy images of HEK 293T cells co-expressing a PA probe (GFP-PASS) and optoPLD targeted to the plasma membrane (C) or lysosomes (D) before (0 min), immediately after (1 min), and 30 min after incubation with 488 nm light. E) Confocal microscopy images of cells co-expressing the PA probe and the indicated optoPLD construct (WT or superPLDx30) targeted to lysosomes, stained with LysoView 633. Scale bar: 10 μm.

FIG. 6A-H. Purification and in vitro characterization of superPLD and PLDWT. A) SDS-PAGE showing His-NusA-superPLD (shown here is clone 2-48) (113 kDa) in cell lysate, His-NusA (58 kDa) being retained on the TALON beads, and superPLD (55 kDa) eluting from the beads and exhibiting high purify after size-exclusion chromatography (SEC). 6×His-NusA-superPLD was expressed in *E. coli* Rosetta 2 and purified using TALON resin. HRV 3C protease was used to cleave between NusA and PLD. B) Ponceau stain with PLDWT and superPLD purified from Rosetta 2 vs. Gami-2 (Rosetta-gami 2) strains. C) Size-exclusion chromatogram of PLDWT purified from Rosetta vs. Gami-2. Black arrow indicates the peak corresponding to PLD. When expressed in the Rosetta strain, PLDWT showed significant degradation and lower yield. D-F) Kinetic analysis of PLD activity. Equal amounts of PLD were prepared based on SDS-PAGE (D) and incubated with indicated concentration of DOPC. Activity assays were performed using the Amplex Red Phospholipase D Assay Kit. The rates of reaction are plotted against the substrate concentration (E), and the data were fit to the Michaelis-Menten equation to obtain the kinetic parameters (F). G) Thermal stability of PLDWT and a subset of superPLD mutants spanning a wide range of activities (see FIG. 2D), indicating no clear correlation between thermal stability and PLD activity. Melting temperature (Tm) was determined in a real-time thermocycler using SYPRO Orange dye. Horizontal lines represent the mean and error bars represent the standard deviation (n=3-8 distinct samples). H) Chemical stability of PLDWT and superPLD (2-48) purified from the Gami-2 strain, indicating increased chemical stability for superPLD. Each enzyme was incubated with indicated concentration of urea in PBS for 12 h at 37° C., followed by an activity assay using the Amplex Red Phospholipase D Assay Kit. Relative rates of reaction compared to control samples (enzymes incubated in PBS only) are plotted, and horizontal lines represent the mean (n=2 distinct samples).

Figure 7:
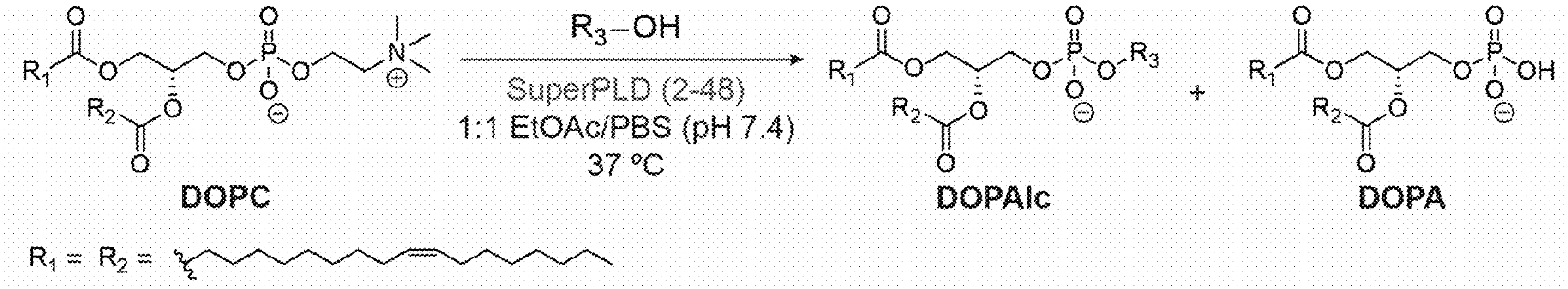
Figure 7:
Figure 7:
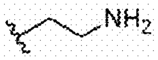
Figure 7:
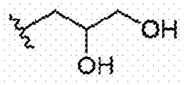
Figure 7:
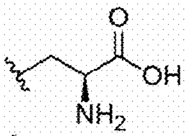
Figure 7:
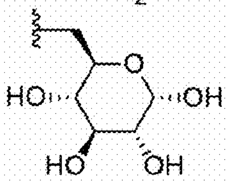
Figure 7:
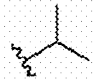
Figure 7:
Figure 7:
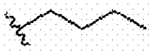
Figure 7:
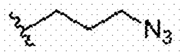
Figure 7:
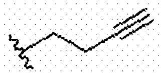

FIG. 7. Synthesis of designer phospholipids by in vitro reaction. The reactions were performed in a biphasic system of ethyl acetate (EtOAc, 0.8 mL) and phosphate-buffered saline (PBS, pH 7.4, 1.0 mL) with 0.8 mg dioleoyl phosphatidylcholine (DOPC), 0.1 μg superPLD (2-48) and 200 μmol (for entries 1-6) or 50 μmol (for entries 7-10) of alcohol. PAlc yield and PA yield indicate the % conversion of DOPC to dioleoyl phosphatidyl alcohol (DOPAlc) and dioleoyl phosphatidic acid (DOPA), respectively.

FIG. 8A-D. Application of superPLD to manipulate PA signaling. A-B) Quantification of nuclear YAP level to evaluate Hippo signaling activity. HEK 293T cells expressing plasma membrane-targeted optoPLD ($PLD^{dead}$, $PLD^{WT}$ or $superPLD^{\times 30}$) were immunostained for YAP (A), and percent signal of YAP colocalized with DAPI (nucleus) signal is plotted for each transfected cell. Horizontal lines indicate average and vertical error bars indicate standard deviation (n=100-120). Scale bars: 10 μm. C) Representative Western blots used to quantify p-AMPK levels (see FIG. 9D). Cells expressing plasma membrane-targeted optoPLD were treated with an CaMKK inhibitor (STO-609) for 6 h to block CaMKK-mediated AMPK activation, followed by a 30 min incubation with 488 nm light. D) Representative Western blots used to quantify p-S6K levels (see FIG. 9E). Cells expressing plasma membrane-targeted optoPLD were treated with an AMPK inhibitor (dorsomorphin) for 1 h, followed by a 30 min incubation with 488 light.

Figures 8A, 8B, 8C, 8D:
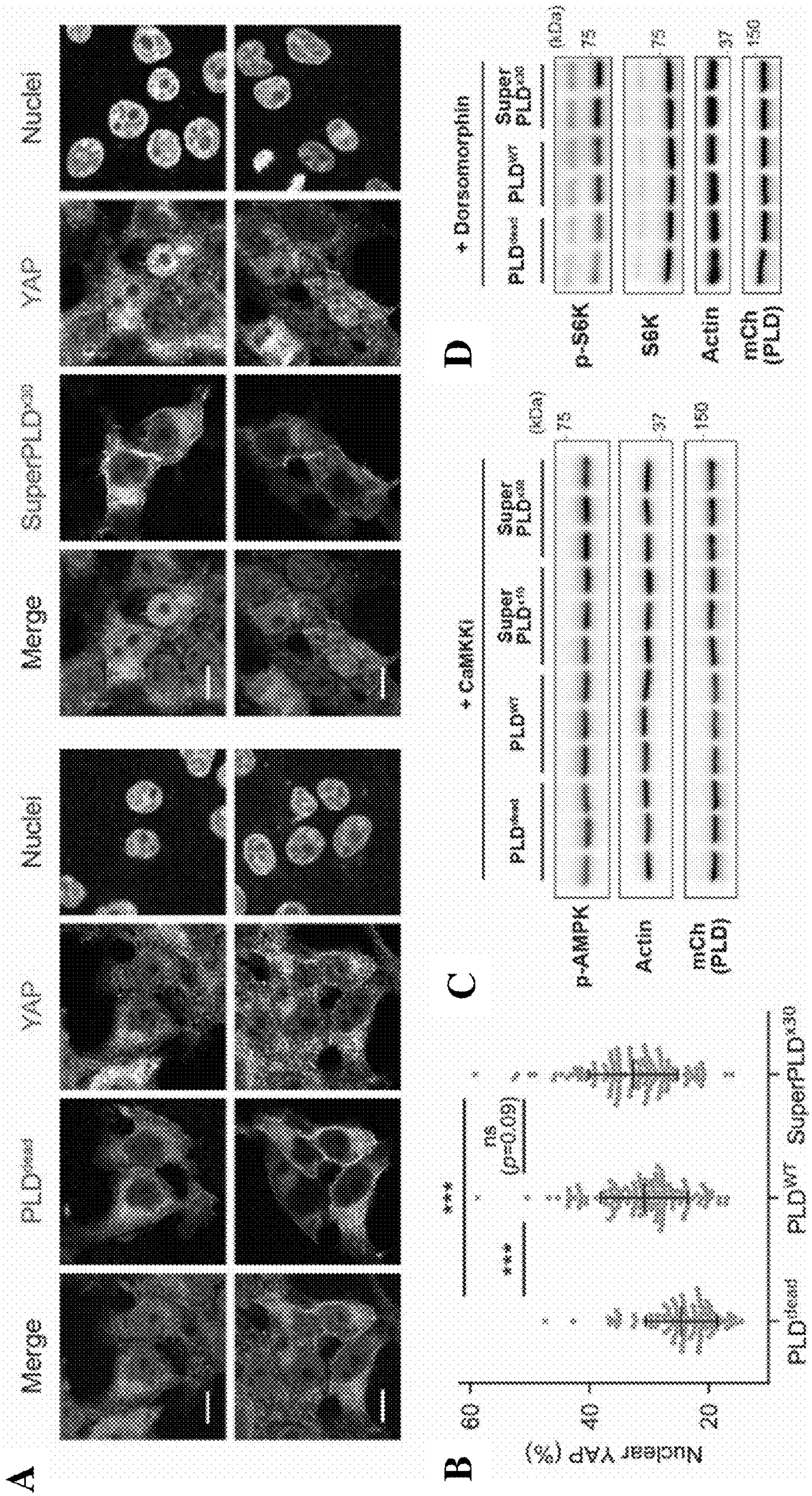

FIG. 9A-E. Application of superPLD to manipulate PA signaling. A) Schematic diagram of effects of PA on AMPK and mTOR signaling. B-C) Recruitment of GFP-LKB1 triggered by acute PA production on lysosomes by superPLD. GFP-LKB1 and optoPLD (mCherry) fluorescence were measured for 30 min, and changes in Pearson correlation coefficient, representing recruitment of GFP-LKB1 to optoPLD-positive membranes, are plotted for each condition (n=5). Scale bar: 10 μm. D) Quantification of phospho-AMPK (p-AMPK) levels in HEK 293T cells with plasma membrane-targeted optoPLDs. Cells were pretreated with a CaMKK inhibitor (STO-609) for 6 h to eliminate CaMKK-mediated AMPK activation, followed by 30 min incubation with intermittent 488 nm light. p-AMPK levels were determined by Western blot (n=6). E) Quantification of phospho-S6 kinase (p-S6K) levels in HEK 293T cells with plasma membrane-targeted optoPLDs. Cells were pretreated with dorsomorphin for 1 h to eliminate effects of p-AMPK on mTOR activity, followed by 30 min incubation with intermittent 488 light. p-S6K levels were determined by Western blot (n=6). FIGS. 8C and D show representative Western blots.

Figure 10A:
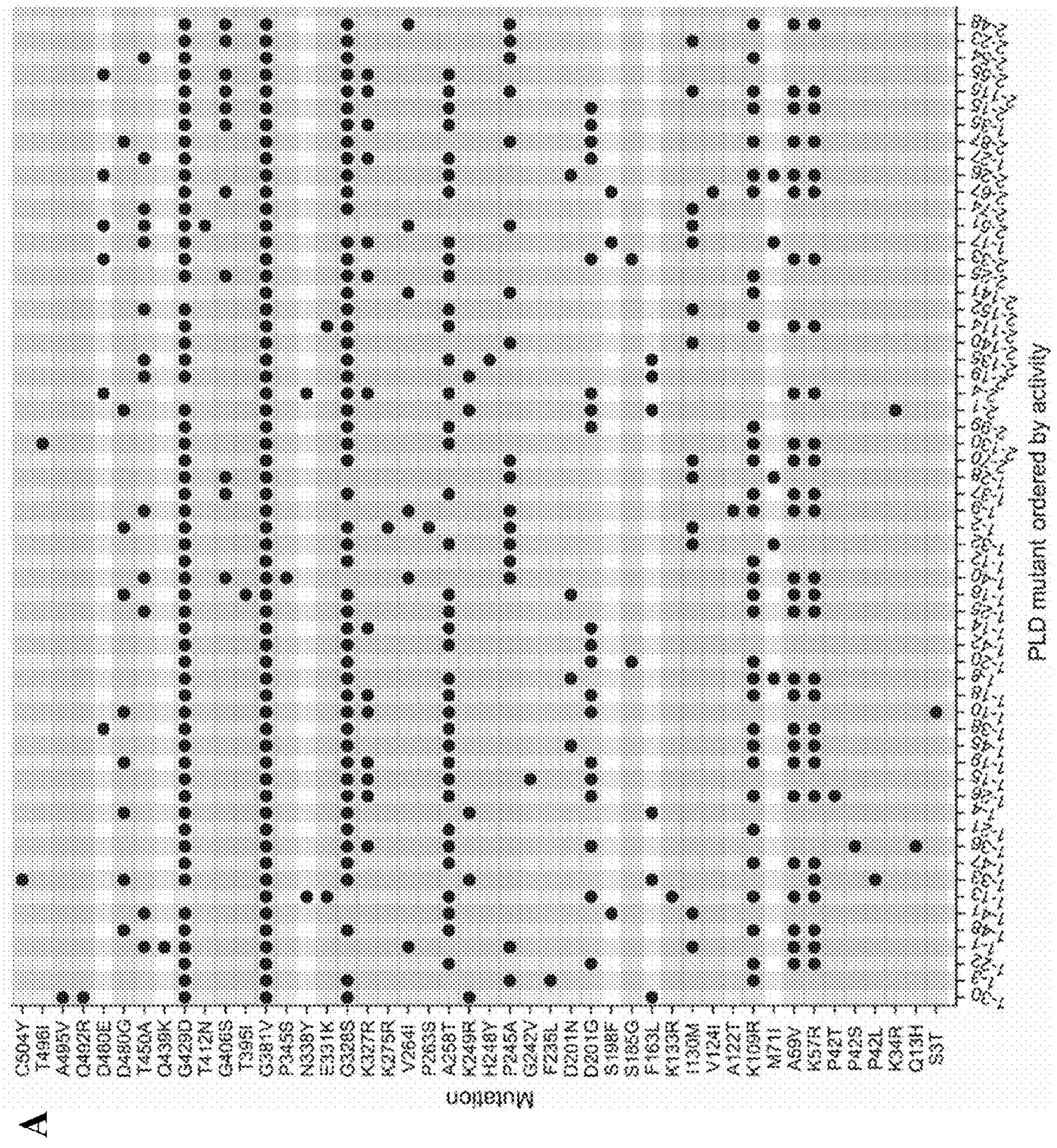
Figure 10B:
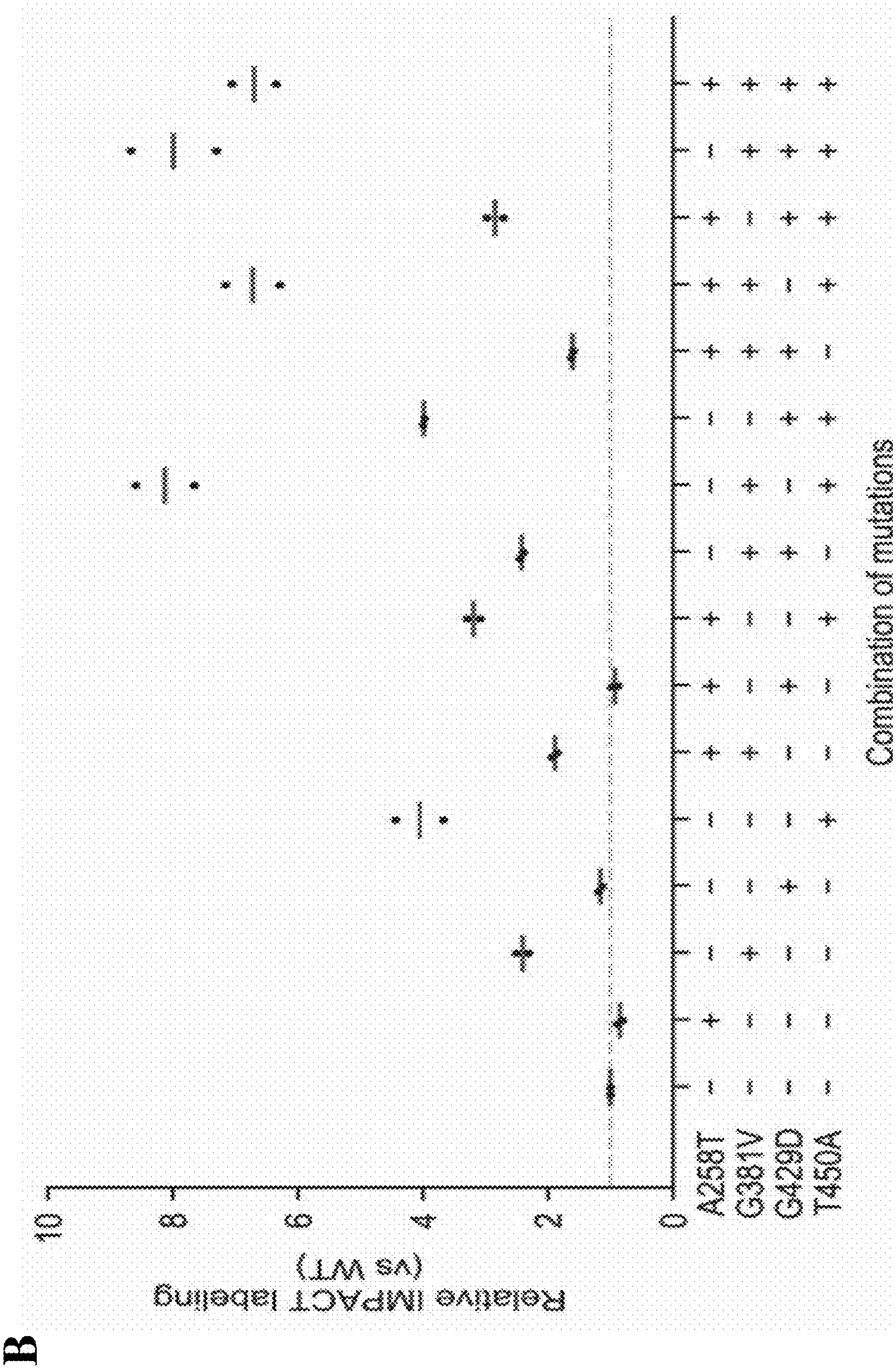

FIG. 10A-B. Mutations identified in various superPLD clones. A) PLD mutant clones are shown in order of PLD activity in cells determined by IMPACT (increasing from left to right), and black dots indicate the presence of a particular point mutation in that PLD mutant. Mutants with identical sets of mutations are not shown in the plot. The mutated residues are colored based on conservation across PLDs from different species, determined by ConSurf1-3; red: high conservation, white: medium, blue: low. SEQ ID NOs for mutant clones along X-axis can be seen in Table 3. B) Activity assay of PLD mutants containing different combinations of four commonly occurring mutations that were generated in the PLDWT background (A258T, G381V, G429D and T450A). Cells expressing plasma membrane-targeted optoPLD with indicated set of mutations were labeled with IMPACT using 1 mM azidopropanol and 1 μM BCN-BODIPY. IMPACT fluorescence intensity normalized to optoPLD expression was determined by flow cytometry, and the relative values for each mutant compared to the PLDWT are plotted as relative IMPACT labeling (n=2 distinct samples). The effect of each mutation occurred mostly in a combinatorial manner (i.e., most mutations exhibited multiplicative effects in either increasing (G381V, T450A) or slightly decreasing (A258T) the activity, though G429D slightly increased activity alone but had negligible effects when combined with other mutations).

FIG. 11A-D. Analysis of the effects of acquired mutations on PLD activity. A) Relative activity of PLDs with frequently occurring mutations that were individually installed into either PLDWT (black) or G381V (magenta) background. Cells were labeled and analyzed by flow cytometry as described in FIG. 10A-B. Horizontal lines indicate average (n=2) of relative mean intensities of IMPACT fluorescence. Dashed gray lines indicate the activity of PLDWT, which is normalized to 1. B-C) Systematic comparison to evaluate the effect of individual mutations in the context of actual superPLD mutants isolated from the screen. The graphs show related mutants grouped separately. Each group contains a "template mutant" consisting of a specific set of mutations (which came from directed evolution experiments), which is shown left-most within each group, as well as other mutants that contain all the mutations in the template mutant plus one additional mutation that is indicated. D) Three different types of effects caused by individual mutations, determined based on point mutation analysis and systematic comparison analysis of mutants.

FIG. 12A-F. Structural comparison of superPLD and PLDWT. A) Crystal structures of superPLD (2-48). Residues mutated in superPLD are shown in yellow. B) Zoomed-in structures around loops 1 and 4. Structures of PLDWT and superPLD are shown in green and magenta, respectively, with loops 1 and 4 in each structure shown in a darker color. C) Zoomed-in structures around His 440. D-E) Surface structures around the catalytic pocket of PLDWT (D) and superPLD (E) highlighting the larger cavity in superPLD. F) Comparison of the effect of mutating cysteine residues on PLDWT (green) vs. superPLD (2-48; magenta) to prevent disulfide bond formation. IMPACT fluorescence intensity normalized to optoPLD expression was determined by flow cytometry. Horizontal lines indicate average (n=2-5) of relative mean intensities of IMPACT fluorescence of cells expressing plasma membrane-targeted optogenetic versions of the indicated mutant PLD compared to the parental PLD (e.g., PLDWT or superPLD (2-48)), as measured by flow cytometry.

FIG. 13A-D. Mapping correlations between structural shifts and mutated sites in superPLDs. A-B) Alignments of PLDWT with either superPLD (2-48) (A) or superPLD (2-23) (B), with the changes in two structures colored by root mean square deviation (RMSD) using the ColorByRMSD script. The distances between aligned Ca atom pairs are stored as B-factors of these residues, which are colored by a color spectrum, with cyan specifying the minimum pairwise RMSD and magenta indicating the maximum. Unaligned residues are colored gray. Sites of mutations in each superPLD are shown in yellow, and mutated residues are shown as yellow sticks except for G381V, which exists on the missing flexible loop that is shown as a yellow dashed line. Loops 1-4 at the entry of the active site are highlighted in red dashed boxes. C) Alignment of PLD from *Streptomyces* sp. PMF and PLD from *Streptomyces antibioticus*, with the differences between the two structures colored by RMSD, demonstrating a high level of structural homology. Loops 1 and 4 are highlighted in red dashed boxes. D) Zoomed-in image of loops 1 and 4. PLD from *Streptomyces* sp. PMF, PLD from *Streptomyces antibioticus*, and superPLD (2-48) are shown in green, cyan, and magenta, respectively. Note that the positions of residues Y186, W190 and Y383 are identical in two wildtype PLDs and found to be largely shifted in superPLD.

FIG. 14A-E. Analysis of the superPLD active site structure of superPLD. A-C) Structures of the active sites of superPLD (2-48) (A), superPLD overlaid with PLDWT (PDB ID: 1V0Y; green) (B), and superPLD overlaid with PLD from *Streptomyces antibioticus* engineered to produce phosphatidylinositol (PDB ID: 7JRV; light blue) (C). Loops 1 and 4 in each structure are shown in dark purple (superPLD 2-48) and dark blue (engineered *S. antibioticus* PLD). A phosphate ligand is modeled in the electron density found in the active site of superPLD. Polder omit map for the region around the modeled phosphate molecule is shown as a mesh, contoured at 0.52σ using a carve distance of 3 Å. D) LC-MS analysis of the lipid extract from purified superPLD, demonstrating the existence of multiple PA species that co-purified with superPLD (2-48). E) Comparison of the effects of site-directed mutation on PLDWT (green) vs. superPLD (2-48; magenta). HEK 293T cells expressing plasma membrane-targeted optoPLD versions of PLDWT or superPLD (2-48) with the indicated point mutation were labeled with 10 mM (for PLDWT) or 100 μM (for superPLD) azidopropanol, followed by click chemistry tagging with 1 μM BCN-BODIPY. IMPACT fluorescence intensity normalized to optoPLD expression was determined by flow cytometry, and the relative values for each mutant compared to the appropriate parental PLD (i.e., PLDWT or superPLD (2-48)) are plotted as relative IMPACT labeling. Plots are replicates (n=2-5 distinct samples) from flow cytometry analysis, and the line indicates the average.

FIG. 15A-G. Disulfide bonds in superPLD and PLDWT structures. A-D) Crystal structures of superPLD (2-48) (A, C, E) and PLDWT (PDB ID: 1V0Y) (B, D) with cysteine residues shown in red. Disulfide bonds in PLDWT are highlighted with red dashed boxes. In superPLD structures, C295 was not resolved, and C341 residue was flipped, indicating that the C295-C341 disulfide bond is reduced. Sites of mutations in superPLD are shown in yellow, with mutated residues shown as yellow sticks (except for G381V, which is in an unresolved flexible loop and is shown as a yellow dashed line). F-G) Identification of a mutation in superPLD that is responsible for enhanced tolerance to disabled disulfide bond formation. Mutations in superPLD (2-48) that occur at three positions near C415 (G328S, G381V, and G406S) were, within the superPLD (2-48) background, reverted to the residue that occurs in PLDWT, and the relative effects of C415S mutation on PLD activity in these constructs (F) were compared to the effect of the C415S mutation in PLDWT (G). IMPACT fluorescence intensity normalized to optoPLD expression was determined by flow cytometry. Horizontal lines indicate average (n=3) of relative mean intensities of IMPACT fluorescence of cells expressing the indicated mutant PLD compared to the parental PLD (e.g., PLDWT or superPLD (2-48)), as measured by flow cytometry.

DETAILED DESCRIPTION

As disclosed herein, substantial technical challenges have been overcome by the present inventors in developing a directed enzyme evolution strategy for Phospholipase D (PLD) in mammalian cells that harnesses a bioorthogonal, activity-based imaging method for fluorescently tagging cellular membranes proportional to PLD activity. A series of PLDs with super activity (superPLDs) have been engineered with greatly enhanced stability in the intracellular environment and catalytic efficiencies up to 100-fold higher than wildtype PLD. Structural and biochemical analysis has revealed that superPLDs possess an expanded active site that allows greater access of water and alcohol substrates and are less reliant upon intramolecular disulfides. Because of their significantly improved intracellular stability and catalytic efficiencies, superPLDs open up applications both in cell biology for membrane editing of the phospholipidome and in biotechnology for the biocatalytic production of commodity and designer phospholipids. Moreover, the demonstration of activity-based directed enzyme evolution in mammalian cells sets the stage for engineering of other chemoenzymatic labeling systems in mammalian cells.

One aspect of the current disclosure is directed to a mutant Phospholipase D (PLD) enzyme comprising an amino acid sequence that varies from the amino acid sequence of a wild type PLD enzyme in at least 6 to 10 substitutions. The wild type PLD enzyme ($PLD^{WT}$) is that of *Streptomyces* sp. PMF and is set forth in SEQ ID NO: 1. The tertiary structure of PLD *Streptomyces* sp. PMF is known and PLD *Streptomyces* sp. PMF is the first known phospholipase D sequence having a tertiary structure. As such, the catalytic mechanism of PLD *Streptomyces* sp. PMF has been further studied. Catalysis proceeds through a two-step (ping-pong mechanism) reaction.

Enzyme engineering is the process of customizing new biocatalysts with improved properties by altering their constituting sequences of amino acids. As used herein, engineered PLDs are PLDs that have been made through the rational design, directed evolution, and semi-rational design methodologies. Rational design strategy is based on the structural analysis and in-depth computational modeling of enzymes by accounting for the physicochemical properties of amino acids and simulating their interactions with the environment. Directed evolution takes after the natural evolution in using mutagenesis for iterative production of mutant libraries, which are then screened for enzyme variants with the desired properties. In terms of this disclosure, site-directed mutagenesis and directed evolution of $PLD^{WT}$ is used in the engineering of PLDs. Since the engineered PLDs described herein are generated through directed evolution, the engineered PLDs can also be referred to as mutant PLDs. As such, the terms "engineered PLDs" and "mutant PLDs" are used interchangeably throughout.

As described herein, the embodiments of mutant PLD enzymes in this disclosure comprise amino acid sequences that vary from the amino acid sequence $PLD^{WT}$ enzyme in at least 6 to 10 substitutions. One of the substitutions to the $PLD^{WT}$ disclosed herein is G381V. As used in this disclosure, the substitutions are described by the amino acid in the wild type, followed by the number representing the position of the amino acid at which the substitution takes place, and ends with the amino acid that replaces the wild type amino acid. For example, G381V means that the glycine at position 381 is replaced by valine. The G381V substitution takes place in every PLD mutant of this disclosure.

Additional amino acid substitutions are selected from the group consisting of S3T, Q13H, K34R, P42L, P42S, P42T, K57R, A59V, M71I, I130M, K133R, F163L, S185G, S198F, D201G, D201N, F235L, G242V, P245A, H248Y, K249R, A258T, P263S, V264I, K275R, K327R, G328S, E331K, N338Y, P345S, T395I, G406S, T412N, G429D, Q439K, T450A, D480G, D480E, Q492R, A495V, T496I, and C504Y.

In some embodiments, one of the additional substitutions is A258T. In some embodiments, one of the additional substitutions is G429D. In some embodiments, one of the additional substitutions is T450A. In some embodiments, the additional substitutions comprise K57R, A59V, K109R, P245A, V264I, G328S, G406S, and G429D. In some embodiments, the additional substitutions comprise I130M, P245A, G328S, G406S, and G429D.

The mutant PLD enzymes of the disclosure exhibit a transphosphatidylation activity at least 2-fold higher than the transphosphatidylation activity of the $PLD^{WT}$ enzyme. In some embodiments of the disclosure, the transphosphatidylation activity is measured in vitro. In such embodiments, the transphosphatidylation activity of the mutant PLD enzymes is at least 2-fold to 5-fold higher than the transphosphatidylation activity of $PLD^{WT}$. In some embodiments, the transphosphatidylation activity of the mutant PLD enzymes is 3-fold higher than that of $PLD^{WT}$ as measured in vitro. In some embodiments, the transphosphatidylation activity of the mutant PLD enzymes is 4-fold higher than that of $PLD^{WT}$ as measured in vitro. In some embodiments, the transphosphatidylation activity of the mutant PLD enzymes is 5-fold higher than that of $PLD^{WT}$ as measured in vitro. Methods for measuring the transphosphatidylation activity of a PLD enzyme in vitro have been described in the art (e.g., H. A. Brown, et al., Methods Enzymol 2007; 434:49-87).

In some embodiments of the disclosure, the mutant PLD enzymes exhibit a transphosphatidylation activity at least 10-fold higher than the transphosphatidylation activity of the $PLD^{WT}$ enzyme when the transphosphatidylation activity is measured in cells. In some embodiments, the transphosphatidylation activity of the mutant PLD enzymes is 15-fold higher than that of $PLD^{WT}$ as measured in cells. In some embodiments, the transphosphatidylation activity of the mutant PLD enzymes is about 30-fold to 125-fold higher than that of $PLD^{WT}$ as measured in cells. In some embodiments, the transphosphatidylation activity of the mutant PLD enzymes is about 50-fold to 110-fold higher than that of $PLD^{WT}$ as measured in cells. In some embodiments, the transphosphatidylation activity of the mutant PLD enzymes is about 60-fold higher than that of $PLD^{WT}$ as measured in cells. In some embodiments, the transphosphatidylation activity of the mutant PLD enzymes is about 70-fold higher than that of $PLD^{WT}$ as measured in cells. In some embodiments, the transphosphatidylation activity of the mutant PLD enzymes is about 80-fold higher than that of $PLD^{WT}$ as measured in cells. In some embodiments, the transphosphatidylation activity of the mutant PLD enzymes is about 90-fold higher than that of $PLD^{WT}$ as measured in cells. In some embodiments, the transphosphatidylation activity of the mutant PLD enzymes is about 100-fold higher than that of $PLD^{WT}$ as measured in cells. In some embodiments, the transphosphatidylation activity of the mutant PLD enzymes is about 110-fold higher than that of $PLD^{WT}$ as measured in cells. In some embodiments, the transphosphatidylation activity of the mutant PLD enzymes is about 120-fold higher than that of $PLD^{WT}$ as measured in cells. Methods for measuring the transphosphatidylation activity of a PLD enzyme in cells have been described in the art (e.g., H. A. Brown, et al., Methods Enzymol 2007; 434:49-87) and also illustrated herein (e.g., Example 1).

In some embodiments of the disclosure, the mutant PLD enzymes exhibit an activity of hydrolysis of phosphatidylcholine to phosphatidic acid that is at least 10-fold higher as compared to the activity of hydrolysis of phosphatidylcholine to phosphatidic acid of $PLD^{WT}$ when the hydrolysis activity is measured in vitro. In some embodiments, the mutant PLD enzyme exhibits an activity of hydrolysis of phosphatidylcholine to phosphatidic acid that is about 10-fold to 50-fold higher as compared to that of $PLD^{WT}$ as measured in vitro. In some embodiments, the mutant PLD enzyme exhibits an activity of hydrolysis of phosphatidylcholine to phosphatidic acid that is about 20-fold higher as compared to that of $PLD^{WT}$ as measured in vitro. In some embodiments, the mutant PLD enzyme exhibits an activity of hydrolysis of phosphatidylcholine to phosphatidic acid that is about 25-fold higher as compared to that of $PLD^{WT}$ as measured in vitro. In some embodiments, the mutant PLD enzyme exhibits an activity of hydrolysis of phosphatidylcholine to phosphatidic acid that is about 30-fold higher as compared to that of $PLD^{WT}$ as measured in vitro. In some embodiments, the mutant PLD enzyme exhibits an activity of hydrolysis of phosphatidylcholine to phosphatidic acid that is about 35-fold higher as compared to that of $PLD^{WT}$ as measured in vitro. In some embodiments, the mutant PLD enzyme exhibits an activity of hydrolysis of phosphatidylcholine to phosphatidic acid that is about 40-fold higher as compared to that of $PLD^{WT}$ as measured in vitro. In some embodiments, the mutant PLD enzyme exhibits an activity of hydrolysis of phosphatidylcholine to phosphatidic acid that is about 45-fold higher as compared to that of $PLD^{WT}$ as measured in vitro. Methods for measuring the hydrolysis activity of a PLD enzyme in vitro are known in the art (e.g., described in part in Mohanty et al., J. Immunol Methods 1997 202(2): 133-41) and kits are commercially available (e.g., the Amplex Phospholipase D kit, available from ThermoFisher). Example 2 herein also shows illustrates these methods.

In some embodiments of the disclosure, the mutant PLD enzymes exhibit an activity of hydrolysis of phosphatidylcholine to phosphatidic acid that is at least 10-fold higher as compared to the activity of hydrolysis of phosphatidylcholine to phosphatidic acid of $PLD^{WT}$ when the hydrolysis activity is measured in cells. In some embodiments, the mutant PLD enzyme exhibits an activity of hydrolysis of phosphatidylcholine to phosphatidic acid that is about 10-fold to 50-fold higher as compared to that of $PLD^{WT}$ as measured in cells. In some embodiments, the mutant PLD enzyme exhibits an activity of hydrolysis of phosphatidylcholine to phosphatidic acid that is about 20-fold higher as compared to that of $PLD^{WT}$ as measured in cells. In some embodiments, the mutant PLD enzyme exhibits an activity of hydrolysis of phosphatidylcholine to phosphatidic acid that is about 25-fold higher as compared to that of $PLD^{WT}$ as measured in cells. In some embodiments, the mutant PLD enzyme exhibits an activity of hydrolysis of phosphatidylcholine to phosphatidic acid that is about 30-fold higher as compared to that of $PLD^{WT}$ as measured in cells. In some embodiments, the mutant PLD enzyme exhibits an activity of hydrolysis of phosphatidylcholine to phosphatidic acid that is about 35-fold higher as compared to that of $PLD^{WT}$ as measured in cells. In some embodiments, the mutant PLD enzyme exhibits an activity of hydrolysis of phosphatidylcholine to phosphatidic acid that is about 40-fold higher as compared to that of $PLD^{WT}$ as measured in cells. In some embodiments, the mutant PLD enzyme exhibits an activity of hydrolysis of phosphatidylcholine to phosphatidic acid that is about 45-fold higher as compared to that of $PLD^{WT}$ as measured in cells. Methods for measuring the hydrolysis activity of a PLD enzyme in cells are illustrated herein (e.g., Example 2).

One aspect of the disclosure is directed to an isolated nucleic acid encoding a mutant PLD enzyme comprising an amino acid sequence that varies from the amino acid sequence of a wild type PLD enzyme as set forth in SEQ ID NO: 1 in at least 6 to 10 substitutions; wherein one of the substitutions is G381V; wherein the additional substitutions are selected from the group consisting of S3T, Q13H, K34R, P42L, P42S, P42T, K57R, A59V, M71I, I130M, K133R, F163L, S185G, S198F, D201G, D201N, F235L, G242V, P245A, H248Y, K249R, A258T, P263S, V264I, K275R, K327R, G328S, E331K, N338Y, P345S, T395I, G406S, T412N, G429D, Q439K, T450A, D480G, D480E, Q492R, A495V, T496I, and C504Y; and wherein the mutant PLD enzyme exhibits a transphosphatidylation activity at least 2-fold higher as compared to the wild type PLD enzyme.

One aspect of the disclosure is directed to an expression vector comprising an isolated nucleic acid encoding a mutant PLD enzyme comprising an amino acid sequence that varies from the amino acid sequence of a wild type PLD enzyme as set forth in SEQ ID NO: 1 in at least 6 to 10 substitutions; wherein one of the substitutions is G381V; wherein the additional substitutions are selected from the group consisting of S3T, Q13H, K34R, P42L, P42S, P42T, K57R, A59V, M71I, I130M, K133R, F163L, S185G, S198F, D201G, D201N, F235L, G242V, P245A, H248Y, K249R, A258T, P263S, V264I, K275R, K327R, G328S, E331K, N338Y, P345S, T395I, G406S, T412N, G429D, Q439K, T450A, D480G, D480E, Q492R, A495V, T496I, and C504Y; and wherein the mutant PLD enzyme exhibits a transphosphatidylation activity at least 2-fold higher as compared to the wild type PLD enzyme. In some embodiments, the nucleic acid encoding a mutant PLD enzyme is operably linked to a promoter functional in a host cell to direct expression of the mutant PLD enzyme. The promoter can be heterologous to the PLD enzyme; in other words, the promoter is from a different gene. The promoter can be constitutive or inducible.

One aspect of the disclosure is directed to a host cell comprising an expression vector comprising an isolated nucleic acid encoding a mutant PLD enzyme comprising an amino acid sequence that varies from the amino acid sequence of a wild type PLD enzyme as set forth in SEQ ID NO: 1 in at least 6 to 10 substitutions; wherein one of the substitutions is G381V; wherein the additional substitutions are selected from the group consisting of S3T, Q13H, K34R, P42L, P42S, P42T, K57R, A59V, M71I, I130M, K133R, F163L, S185G, S198F, D201G, D201N, F235L, G242V, P245A, H248Y, K249R, A258T, P263S, V264I, K275R, K327R, G328S, E331K, N338Y, P345S, T395I, G406S, T412N, G429D, Q439K, T450A, D480G, D480E, Q492R, A495V, T496I, and C504Y; and wherein the mutant PLD enzyme exhibits a transphosphatidylation activity at least 2-fold higher as compared to the wild type PLD enzyme. In some embodiments, host cells include cultured cells. In some embodiments, the host cell is a mammalian cell. In some embodiments, host cells include cultured mammalian cells, such as CHO cells, BHK cells, NSO cells, SP2/0 cells, HEK cells, or hybridoma cells. In some embodiments, the host cell is an HEK293 cell.

Another aspect of the disclosure is directed to a method of using a mutant PLD enzyme as a catalyst for in vitro synthesis of phospholipids, where the method comprises synthesizing phospholipids from phosphatidylcholine and an alcohol substrate using a mutant PLD enzyme, where the phospholipid head of the phosphatidylcholine is replaced to form a natural or unnatural phosphatidyl alcohol. In one embodiment, the unnatural phosphatidyl alcohol comprises a reactive polar head and is synthesized with high selectivity and high yield. In some embodiments, the alcohol is for click-chemistry reactions. In some embodiments, the alcohol is for inverse electron-demand Diels-Alder click chemistry reactions, also known as the "tetrazine ligation." In one embodiment, the reactive polar head comprises an azide, an alkyne, or trans-cyclooctene alcohols.

In some embodiments of the disclosure, the phosphatidylcholine (PC) varies in form of lipid substrate. In some embodiments the lipid substrate is an acyl tail form of PC. In some embodiments, the lipid substrate is a naturally occurring acyl tail form of PC. In some embodiments, the lipid substrate is a naturally occurring lecithin. In some embodiments, the lipid substrate is dioleoyl phosphatidylcholine (DOPC). In some embodiments, the lipid substrate is dipalmitoyl PC (DPPC). In some embodiments, the lipid substrate is 1-palmitoyl-2-oleoyl PC (POPC).

In some embodiments of the disclosure, the PC is hydrolyzed to synthesize a phosphatidyl alcohol (PA). In some embodiments, the synthesized PA comprises dioleoyl phosphatidyl alcohol (DOPAlc). In some embodiments, the synthesized PA comprises dioleoyl phosphatidic acid (DOPA). In some embodiments, the synthesized PA comprises dipalmitoyl phosphatidyl alcohol (DPPA). In some embodiments, the synthesized PA comprises 1-Palmitoyl-2-Oleoyl-sn-Glycero-3-Phosphatidic acid (POPA). In some embodiments, the synthesized PA comprises 1-palmitoyl-2-oleoyl-sn-glycero-3-phosphoethanol (POPAlc).

In some embodiments, the method uses a mutant PLD enzyme disclosed herein as a catalyst for synthesis of phospholipids in a mammalian cell, where the method comprises providing a mammalian cell with one or more alcohol substrates, wherein the mammalian cell expresses the mutant PLD enzyme and displays phosphatidylcholine in cellular membranes; and permitting the mutant PLD enzyme to replace the phospholipid head of the phosphatidylcholine with an alcohol substrate to form a natural or unnatural phosphatidyl alcohol, thereby making phospholipids. In one embodiment, the unnatural phosphatidyl alcohol comprises a reactive polar head and is synthesized with high selectivity and high yield. In some embodiments, the alcohol is for click chemistry reactions. In some embodiments, the alcohol is for inverse electron-demand Diels-Alder click chemistry reactions, also known as the "tetrazine ligation." In one embodiment, the reactive polar head comprises an azide, an alkyne, or trans-cyclooctene alcohols.

As used herein, "cellular membranes" refers to the plasma membrane and intracellular organelle membranes. Examples of membraned intracellular organelles include a variety of membranes associated with the cell nucleus; the mitochondria; the Golgi apparatus; the endoplasmic reticulum; lysosomes; plastids; and vacuoles.

In some embodiments of the disclosure, the phosphatidylcholine (PC) varies in form of lipid substrate. In some embodiments the lipid substrate is an acyl tail form of PC. In some embodiments, the lipid substrate is a naturally occurring acyl tail form of PC. In some embodiments, the lipid substrate is a naturally occurring lecithin. In some embodiments, the lipid substrate is dioleoyl phosphatidylcholine (DOPC). In some embodiments, the lipid substrate is dipalmitoyl PC (DPPC). In some embodiments, the lipid substrate is 1-palmitoyl-2-oleoyl PC (POPC).

In some embodiments of the disclosure, the PC is hydrolyzed to synthesize a phosphatidyl alcohol (PA). In some embodiments, the synthesized PA comprises dioleoyl phosphatidyl alcohol (DOPAlc). In some embodiments, the synthesized PA comprises dioleoyl phosphatidic acid (DOPA). In some embodiments, the synthesized PA comprises dipalmitoyl phosphatidyl alcohol (DPPA). In some embodiments, the synthesized PA comprises 1-Palmitoyl-2-Oleoyl-sn-Glycero-3-Phosphatidic acid (POPA). In some embodiments, the synthesized PA comprises 1-palmitoyl-2-oleoyl-sn-glycero-3-phosphoethanol (POPAlc).

One aspect of the disclosure is directed to a method of using a mutant PLD enzyme to modulate phosphatidic acid (PA)-dependent Hippo growth restriction pathway. In some embodiments, the method comprises increasing the PA made at the plasma membrane using a mutant PLD enzyme as described herein, wherein the PA attenuates Hippo growth restriction pathway by triggering the translocation of Yes-associated protein (YAP) from the cytosol to the nucleus in serum-starved cells.

One aspect of the disclosure is directed to a method of using a mutant PLD enzyme to modulate PA-dependent AMP-activated protein kinase (AMPK) signaling, the method comprising synthesizing PA made at cellular membranes using a mutant PLD enzyme according to any one of claims 1 through 6, wherein the PA induces liver kinase B1 (LKB1) translocation to PA-rich membranes, leading to an increase of AMPK phosphorylation.

One aspect of the disclosure is directed to a method of using a mutant PLD enzyme to modulate PA-dependent mammalian target of rapamycin (mTOR) signaling, the method comprising treating cells expressing plasma membrane-targeted optoPLD with an AMPK inhibitor followed by using a mutant PLD enzyme according to any one of claims 1 through 6; wherein the mutant PLD enzyme increases phosphorylation of the mTOR effector S6 kinase.

Another aspect of the disclosure is directed to a method of identifying a nucleic acid encoding a mutant PLD that exhibits a transphosphatidylation activity at least 10-fold higher in mammalian cells as compared to a wild type PLD enzyme which comprises the amino acid sequence of SEQ ID NO: 1, the method comprising:

a) generating a mutant PLD library which comprises nucleic acids encoding mutant PLD enzymes;
b) introducing the library to cells of a mammalian cell line and expressing the mutant PLD enzymes from the library in the cells;
c) labeling the cells expressing mutant PLD enzymes based on the transphosphatidylation activities of the mutant PLD enzymes; and
d) identifying and recovering cells expressing a mutant PLD enzyme that exhibits a transphosphatidylation activity at least 10-fold higher in mammalian cells as compared to the wild type PLD enzyme.

One embodiment of the disclosure is directed to a method of identifying a nucleic acid encoding a mutant PLD that exhibits a transphosphatidylation activity at least 10-fold higher in mammalian cells as compared to a wild type PLD enzyme which comprises the amino acid sequence of SEQ ID NO: 1, wherein step c) comprises labeling the cells expressing the mutant PLD enzymes through activity-based fluorescent labeling. In one embodiment, the activity-based fluorescent labeling is a bioorthogonal labeling method. In one embodiment, the bioorthogonal labeling method is Imaging PLD Activity with Clickable Alcohols via Transphosphatidylation (IMPACT).

As used herein, IMPACT is an approach that capitalizes on the ability of PLDs to catalyze transphosphatidylation reactions with exogenous alcohols to generate phosphatidyl alcohols, lipids whose location and abundance report on the extent of PLD-mediated PA synthesis. Employing functionalized "clickable" alcohols as PLD substrates enables the subsequent tagging of the resultant phosphatidyl alcohols with fluorophores or other functional probes for detection via highly selective click chemistry reactions. IMPACT can be coupled to downstream analysis by fluorescence microscopy, flow cytometry, HPLC, or mass spectrometry. Two variants of IMPACT are known, one with greater sensitivity, for detecting PLD activity at single-cell and population levels, and one with greater spatiotemporal resolution ("real-time," or RT-IMPACT), for accurately visualizing PLD activity at the subcellular, individual-organelle level.

In some embodiments, step d) is performed by fluorescence activated cell sorting (FACS). One embodiment further comprises extracting DNA from the recovered cells to recover nucleic acids encoding the mutant PLD enzymes. One embodiment further comprises introducing the recovered nucleic acids to cells of a mammalian cell line and expressing the mutant PLD enzymes from the recovered nucleic acids in the cells; labeling the cells expressing mutant PLD enzymes based on the transphosphatidylation activities of the mutant PLD enzymes; and identifying and recovering cells expressing a mutant PLD enzyme that exhibits a transphosphatidylation activity in mammalian cells at least 10-fold higher as compared to the wild type PLD enzyme.

EXAMPLES

The following examples are presented to illustrate the present disclosure. The examples are not intended to be limiting in any manner.

Example 1. Activity-Based Directed Evolution in Mammalian Cells Achieves a Substantial Enhancement of PLD Activity We have previously identified PLD from *Streptomyces* sp. PMF for heterologous expression in mammalian cells and developed a light-controlled, optogenetic version of the PLD from *Streptomyces* sp. PMF (optoPLD). OptoPLD-targeting plasma membrane can be controlled by swapping the plasma membrane-targeted domain, CAAX, with another membrane-targeting domain. Though optoPLD enabled production of PA or certain phosphatidyl alcohol lipids with organelle-level precision, it exhibited very modest activity, compromising its temporal resolution, and accepted a limited set of alcohol substrates. To improve its activity, PLD-expressing yeast cells for directed evolution were first used. However, the FACS-based selection was inefficient due to the yeast cell wall, which prevented efficient entry and rinse-out of labeling reagents into live and even fixed cells. Consequently, this platform did not yield PLD mutants with substantially enhanced activity compared to PLDWT; the best-performing mutant, G429D, was only 1.3-fold better than PLDWT.

The activity-based directed evolution strategy in mammalian cells in this disclosure comprises four fundamental steps (FIG. 1). First, a PLD library with random mutations is generated by error-prone PCR, using either WT or G429D as a template, and then cloned into a lentiviral vector containing the optoPLD system, which enables blue light-dependent PLD activation mediated by CRY2-CIBN dimerization to recruit PLD to a desired membrane. Second, lentivirus containing this optoPLD library is generated and delivered into HEK 293T cells such that each cell expresses a different optoPLD mutant. Third, activity-based fluorescent labeling is performed using a bioorthogonal labeling method termed Imaging PLD Activity with Clickable Alcohols via Transphosphatidylation (IMPACT). This can be seen in FIG. 2A. Fourth, cells are sorted by FACS based on IMPACT fluorescence intensity normalized to optoPLD expression, with IMPACT-high cells collected and propagated.

After 1-2 cycles of IMPACT and FACS sorting, the enriched PLD library is isolated by DNA extraction and PCR amplification. Subsequent rounds of evolution, with or without additional mutagenesis, is performed while increasing stringency by lowering the concentration of the IMPACT labeling reagent azidopropanol (FIG. 3A-S). Overall, we performed three rounds of selection with mutagenesis to increase library diversity and, critically, then five rounds without additional mutagenesis to remove false-positive populations, leading to a dramatic enrichment of highly active PLD mutants (FIG. 2B).

After the final round of selection, 216 individual clones of the enriched library were isolated through two batches. 194 (90%) of those exhibited higher activity than $PLD^{WT}$ using IMPACT labeling to assess activity of these mutant PLDs within an optoPLD system. These mutants exhibited a wide range of activities, with the highest active mutant, clone 2-48, exhibiting about 100× higher activity than $PLD^{WT}$ (FIG. 2C-D and FIG. 3T-V). These mutants were donated as superPLDs due to this substantial improvement in performance in cells.

Example 2. SuperPLDs are Efficient PC Hydrolase and Transphosphatidylase

Figures 2A, 2B, 2C:
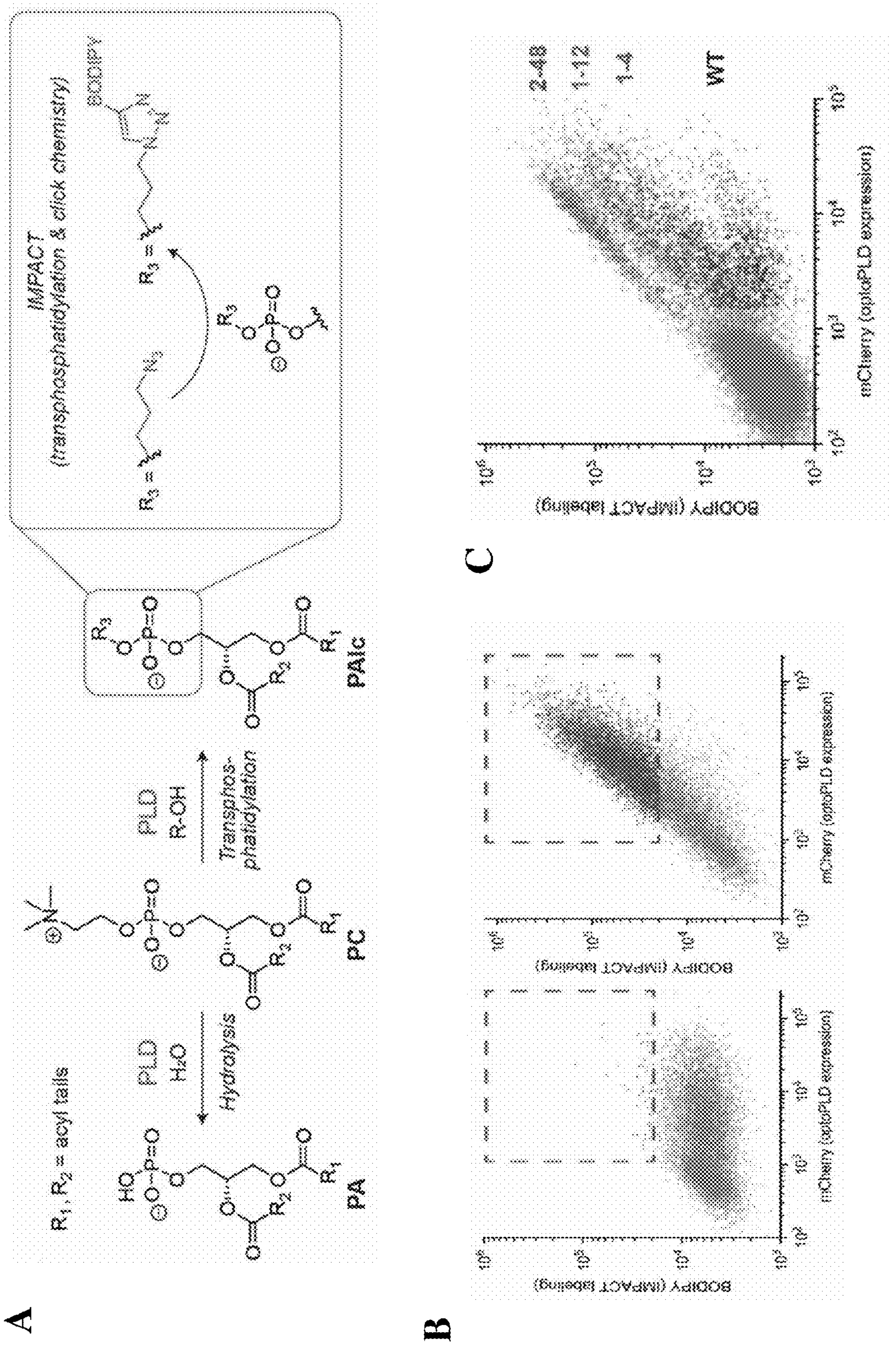
FIG. 2A-D. Directed evolution yields PLD mutants with greatly enhanced activities. A) Reactions catalyzed by PLD, including hydrolysis (left) and transphosphatidylation (right) by using water and alcohols as substrates, respectively. For IMPACT, transphosphatidylation is used to produce azide-tagged phospholipids, which are then reacted with a bicyclononyne-BODIPY probe to fluorescently tag the lipids produced by PLD. B) FACS plots showing signal enrichment before (left) and after (right) five rounds of selection without mutagenesis. Red dots indicate cells that were collected. C) Overlay of FACS plots of cells expressing different optoPLD mutants. Colored dots indicate cells expressing PLDWT (black), 1-4 (blue), 1-12 (green) and 2-48 (magenta). D) Relative PLD activity of representative plasma membrane-targeted optoPLD mutants obtained by directed evolution. IMPACT fluorescence intensity normalized to optoPLD expression was determined by flow cytometry, and the activities are plotted as relative IMPACT labeling of the indicated PLD mutant compared to $PLD^{WT}$. SEQ ID NOs for mutant clones along X-axis can be seen in Table 3.
Figure 2D:
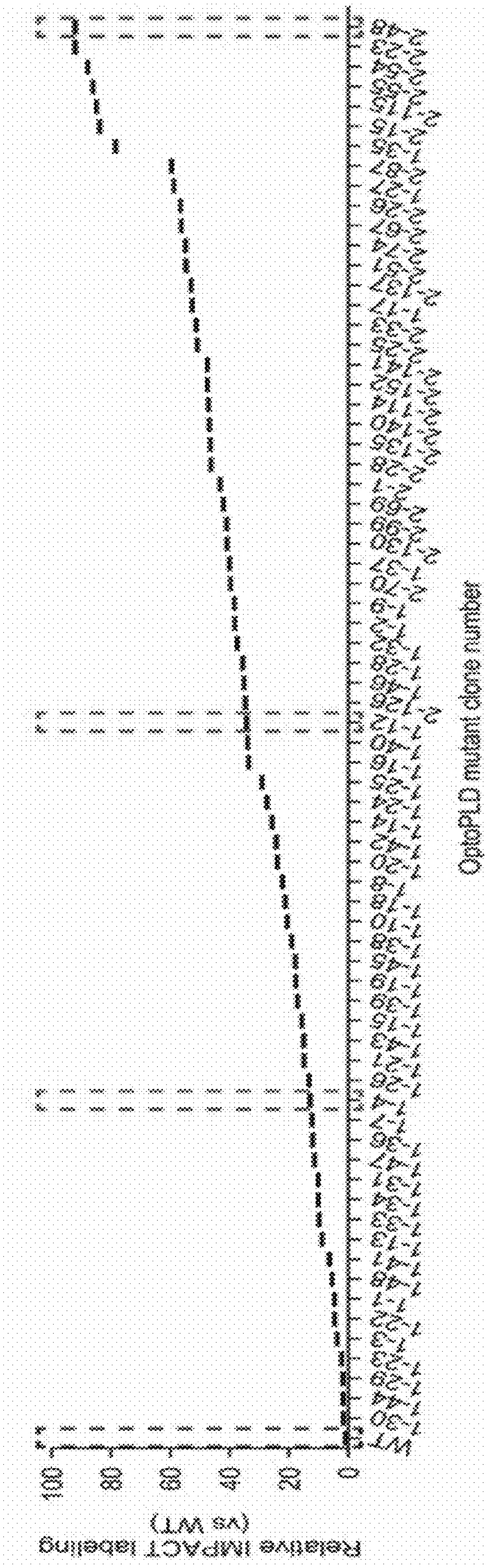
Figures 3A, 3B, 3C, 3D, 3E, 3F, 3G, 3H, 3I, 3J, 3K:
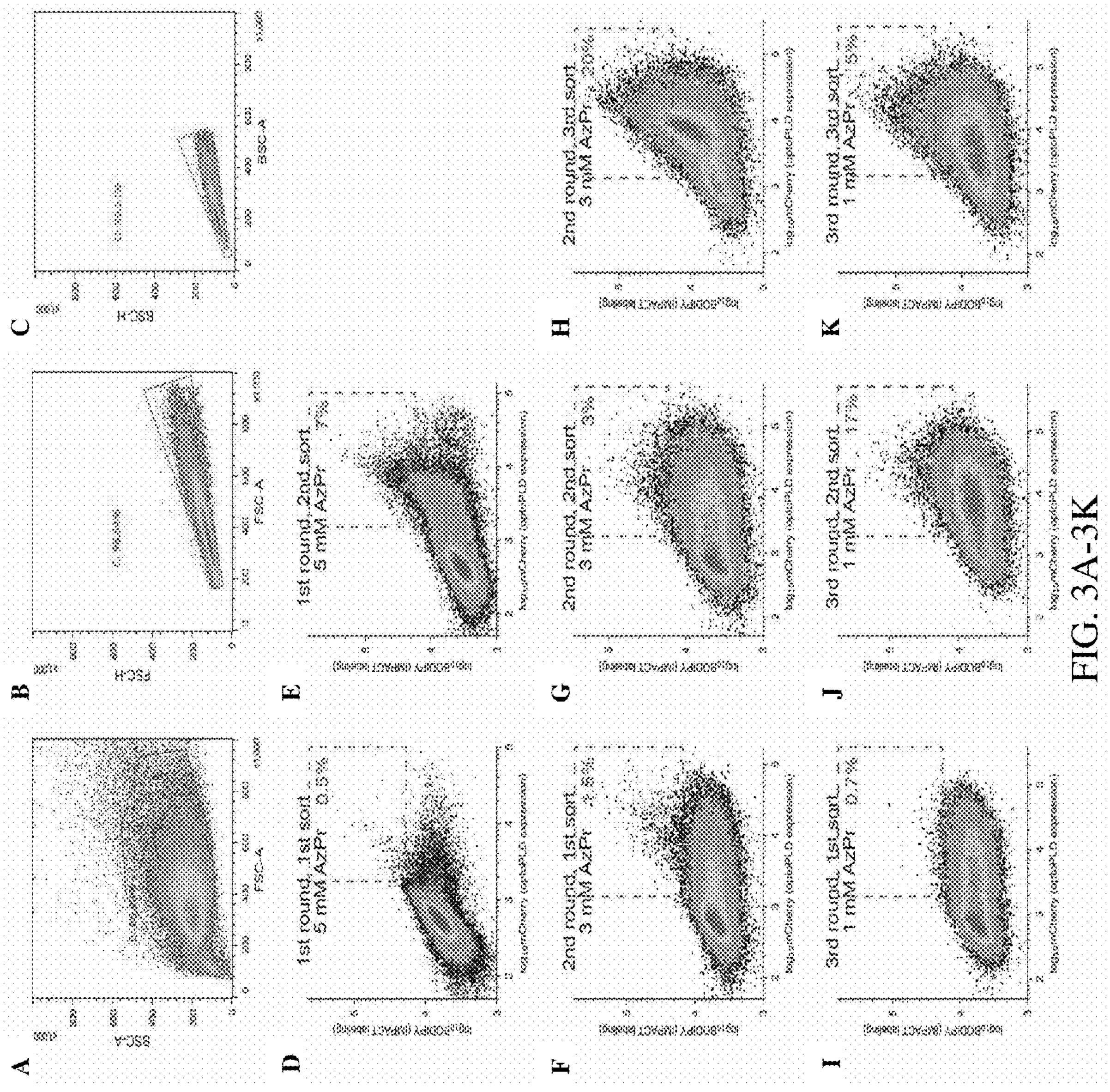
FIG. 3A-X. FACS plot and gating strategy for each sorting of directed evolution and superPLD characterization by IMPACT. A-C) Gating strategy for sorting and analysis of HEK 293T cells expressing optoPLD mutants labeled by IMPACT. Plots of FSC-A vs. BSC-A, population B selected (A), FSC-A vs. FSC-H, population C selected (B), and BSC-A vs. BSC-H, population D selected (C) were used to gate for live, singlet cells. D-K) FACS plot of PLD library from each sorting in three rounds of selection with mutagenesis. L-S) FACS plot of PLD library from each sorting in five rounds of selection without mutagenesis. The round number, sort number within that round, concentration of azidopropanol (AzPr) used for IMPACT labeling, and the percentage of cells collected are indicated in each plot. T) Gating strategy for quantitative comparison of IMPACT labeling. The average BODIPY signal of cells with similar amount of mCherry signal (population shown in red, which is gated for an mCherry fluorescence of $5\times10^3$-$1\times10^4$), was used. U-V) mCherry (U) and IMPACT labeling (V) histograms of cells expressing $PLD^{WT}$ (black), 1-4 (blue), 1-12 (green) and 2-48 (magenta), demonstrating that optoPLD mutants with different activity have similar expression levels. W-X) The effect of light stimuli on optoPLD activity. Cells expressing optoPLD were treated with 0.5 mM azidopropanol with or without intermittent blue light illumination, followed by treatment with 1 μM BCN-BODIPY, and IMPACT fluorescence intensity normalized to optoPLD expression was determined by flow cytometry. Horizontal lines indicate average (n=3) of mean intensities of IMPACT fluorescence. $PLD^{dead}$, a catalytically dead PLD bearing the H167A mutation; $PLD^{WT}$, wild-type PLD; $superPLD^{\times10}$, superPLD mutant clone 1-4; $superPLD^{\times30}$, superPLD mutant clone 1-12; $superPLD^{\times50}$, superPLD mutant clone 1-27; $superPLD^{\times10}$, superPLD mutant clone 2-48.
Figures 3L, 3M, 3N, 3O, 3P, 3Q, 3R, 3S, 3T, 3U, 3V, 3W, 3X:
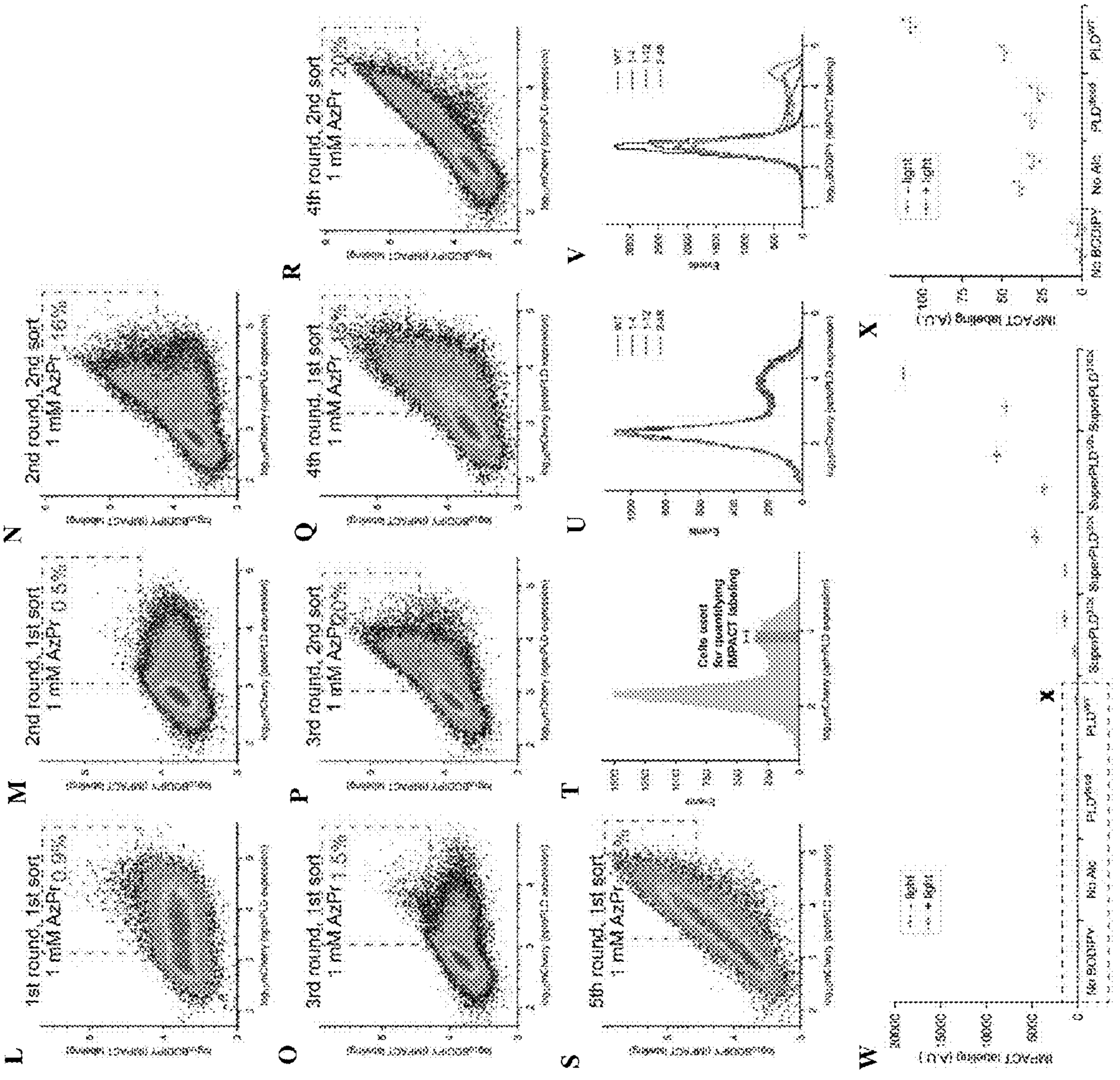
Figures 4A, 4B, 4C, 4D:
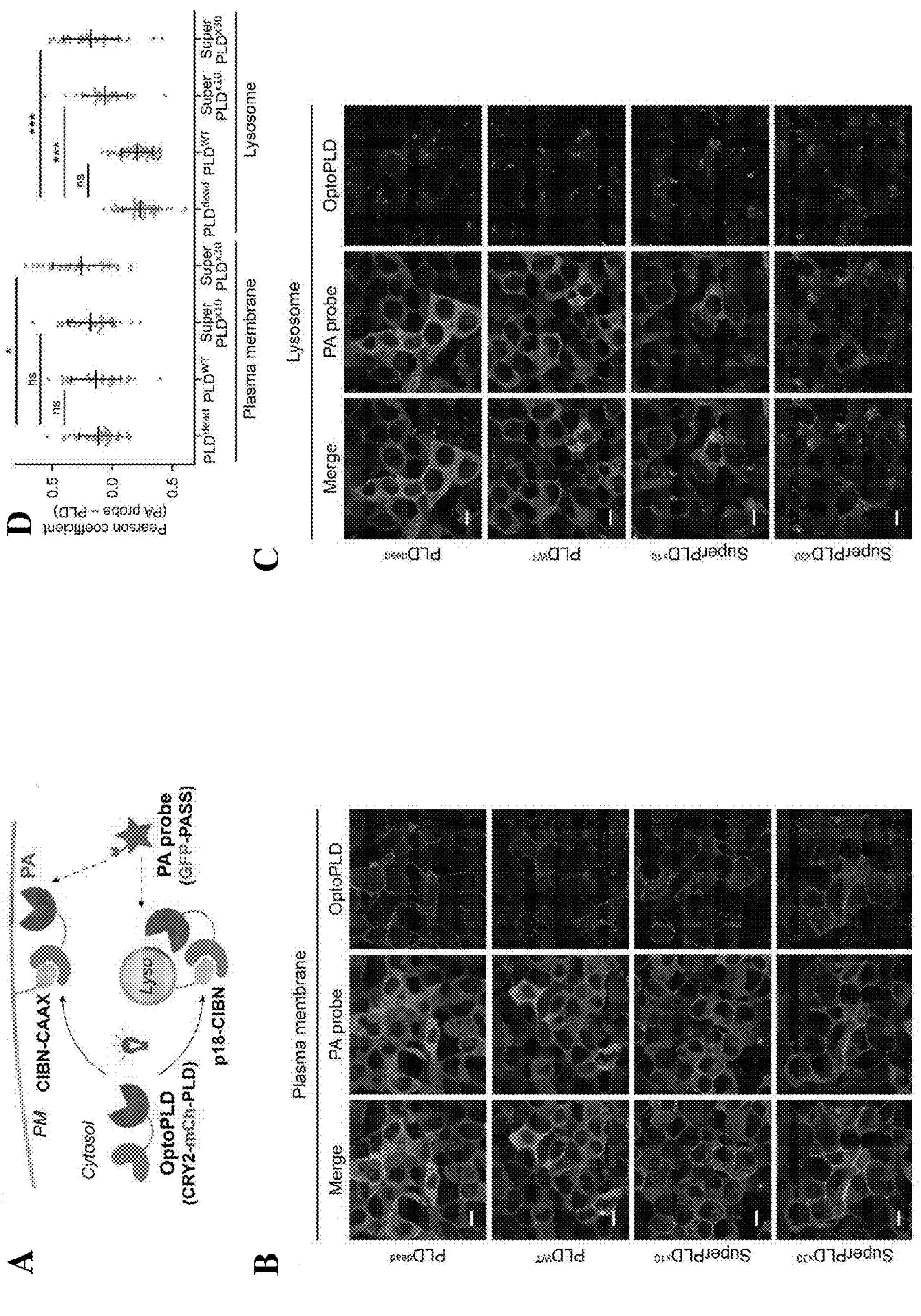
FIG. 4A-D. Evaluation of superPLD activity in cells. A) Schematic depicting the experimental design of targeting optoPLD to the plasma membrane (PM) or lysosomes (lyso) and using the PA probe GFP-PASS to visualize PA produced by optoPLD. B-C) Confocal images of HEK 293T cells co-expressing the PA probe and optoPLD targeted to the plasma membrane (B) or lysosomes (C) after 30 min incubation with 488 nm light. D) Quantification of co-localization between PA probe and optoPLD. The plots show Pearson's correlation coefficient of PA probe and optoPLD.
Figures 5A, 5B, 5C, 5D, 5E:
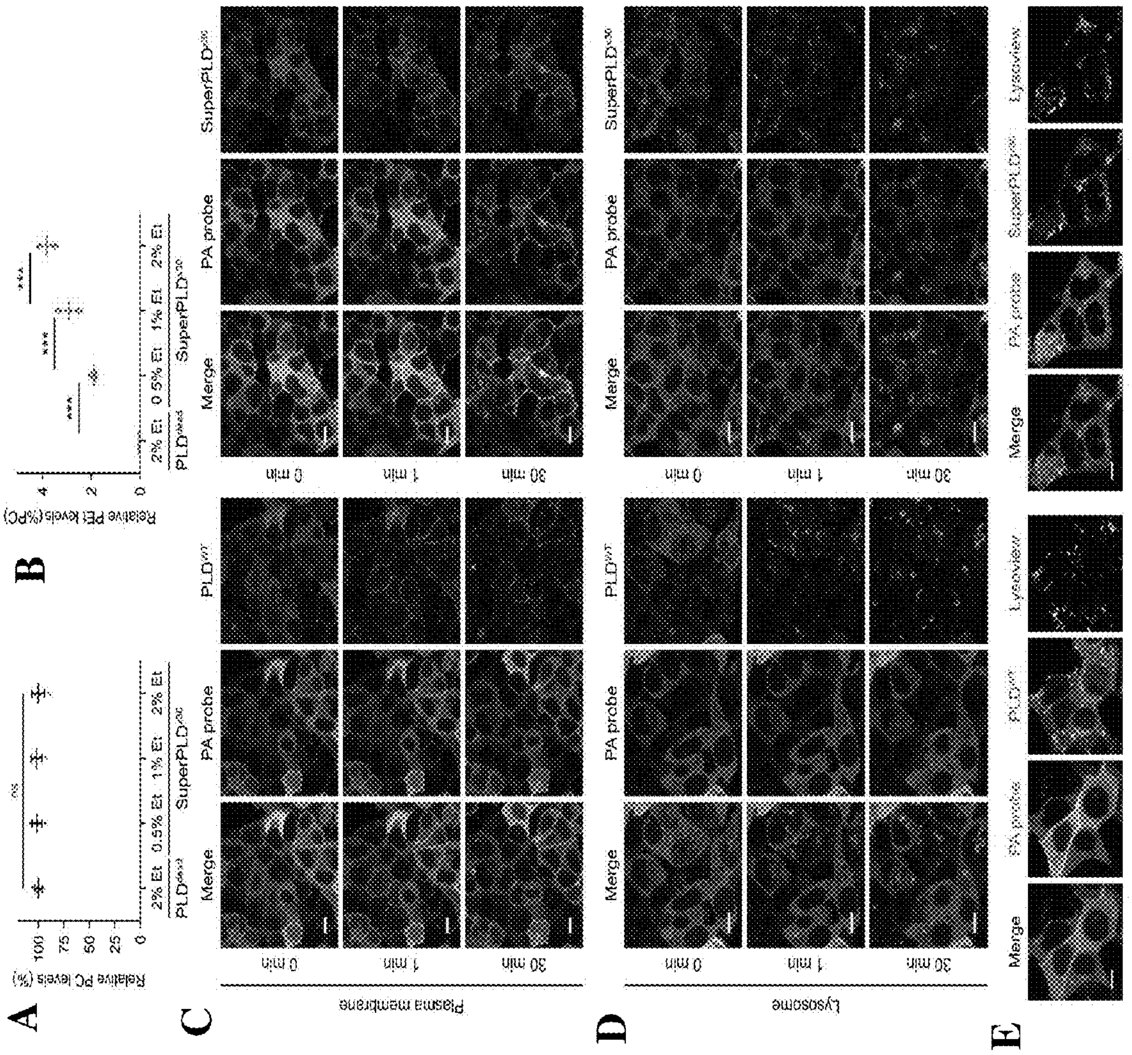

Having obtained PLD mutants with a wide-ranging degree of transphosphatidylation activities to generate fluorescent lipids via IMPACT, the ability of the PLD mutants to catalyze PC hydrolysis to form PA and transphosphatidylation to form other useful phospholipids was assessed (FIG. 2A). Next, a PA-binding probe, GFP-PASS, was used to visualize the subcellular localizations of PA in order test superPLD-mediated PA production in cells. An optoPLD construct containing the highest active superPLD (clone 2-48; SEQ ID NO: 2) exhibited substantial light-independent background activity in cells (FIG. 3W-X), resulting in increased cytotoxicity under certain conditions, e.g., stable expression following lentiviral transduction. Therefore, optoPLDs were generated where the optoPLDs bear moderately active superPLDs (superPLDx10 and superPLDx30, made from clone 1-4 (SEQ ID NO: 49) and clone 1-12 (SEQ ID NO: 34) with approximately 10× and 30× higher activity than $PLD^{WT}$, respectively). These moderately active superPLDs were capable of being recruited to either the plasma membrane or lysosomes upon light activation (FIG. 4A). LC-MS analysis of transphosphatidylation reactions revealed that superPLDx30 activation consumed approximately 2-4% of PC in cells, and total PC levels did not significantly change, likely due to continuous replenishment from biosynthesis (FIG. 5A-B). With plasma membrane-targeted optoPLDs superPLDx10 and superPLDx30 efficiently recruited GFP-PASS to the plasma membrane (FIG. 4B). However, $PLD^{WT}$ did not have the same effect on GFP-PASS to the plasma membrane (FIG. 5C). Similarly, superPLDx10 and superPLDx30 greatly outperformed $PLD^{WT}$ in lysosome-targeted optoPLD constructs (FIG. 4C and FIG. 5D-E).

Figures 6A, 6B, 6C, 6D, 6E, 6F, 6G, 6H:
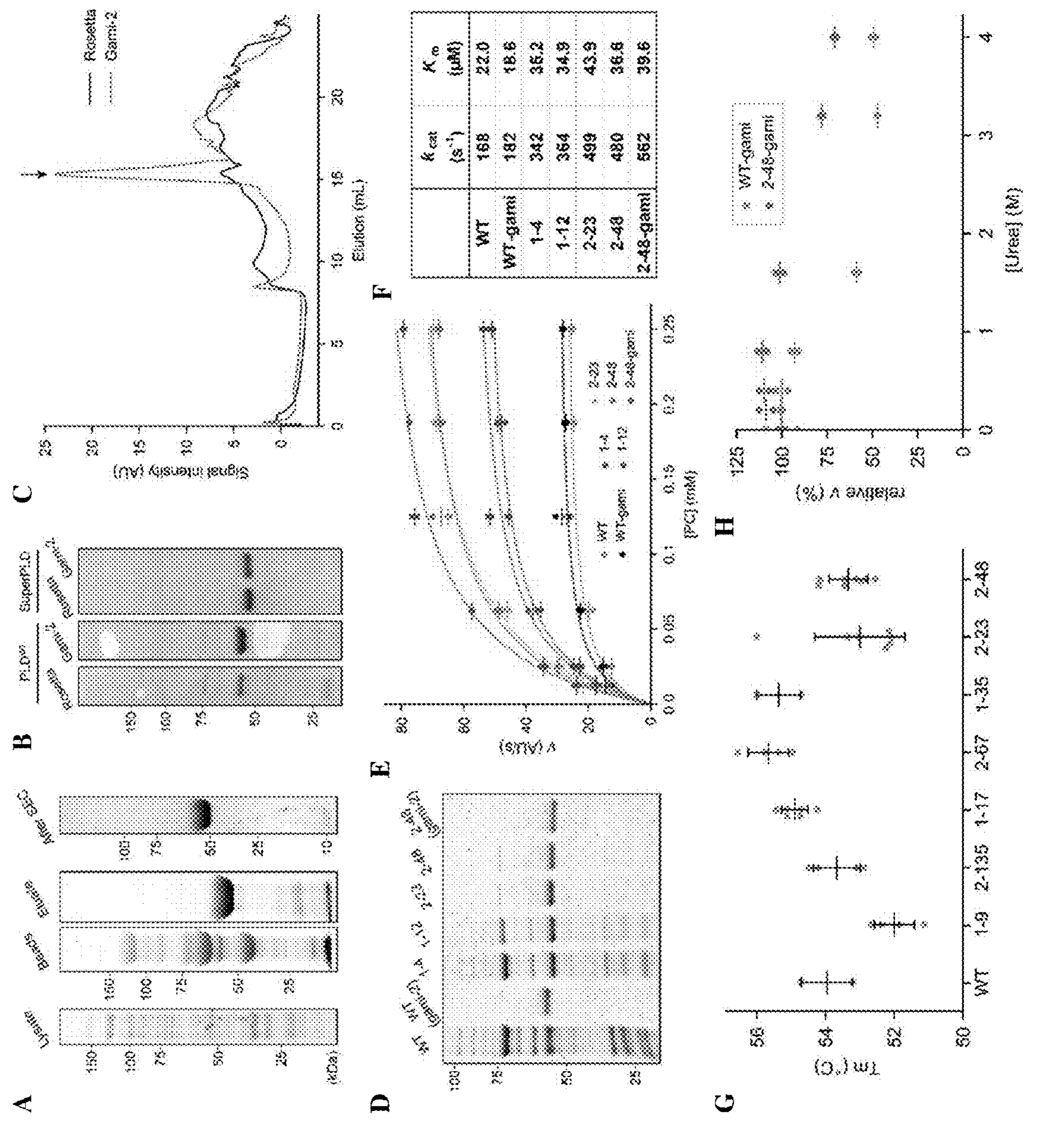

His-tagged superPLDs expressed in the *E. coli* Rosetta 2 strain was purified to evaluate PLD activity in vitro (FIG. 6A). The *E. coli* Rosetta-gami 2 strain is an engineered strain that facilitates disulfide bond formation in the cytosol (Rosano, G. L. & Ceccarelli, E. A., Front. Microbiol. 5, (2014)). Remarkably, $PLD^{WT}$ was unable to be purified in this manner until switching to the *E. coli* Rosetta-gami 2 strain, which is consistent with this PLD being a secreted protein with four disulfide bonds (FIG. 6B-C). The finding that superPLD can be robustly purified from a conventional *E. coli* strain suggests that one potential source of improved superPLD performance is an enhanced stability in intracellular, reductive environments. Supporting this hypothesis, the activity increase of superPLD was more substantial in cells than in vitro, and superPLD exhibited enhanced chemical stability compared to $PLD^{WT}$ (FIG. 2D and FIG. 6D-H).

It is generally thought that transphosphatidylation of PC by PLDs is preferred to hydrolysis Yang, H. & Roberts, M. F. Protein Sci. Publ. Protein Soc. 12, 2087-2098 (2003) and Allegretti, C., et al., Catalysts 10, 997 (2020). Therefore, the ability of superPLD was assessed for use as a catalyst for the in vitro synthesis of a variety of phospholipids from phosphatidylcholine and alcohol substrates. Both PA and phosphatidyl alcohol products were quantified by LC-MS, superPLD could be successfully used for synthesis of various useful natural and unnatural phosphatidyl alcohols derived from both primary and secondary alcohols, with minimal PA by-products formed (FIG. 7). Notably, several unnatural phospholipids with reactive handles such as azide and alkyne could be synthesized with high selectivity and yield. These studies demonstrate the utility of superPLD as a biocatalyst to efficiently produce natural and unnatural phospholipids in in vitro chemoenzymatic reactions.

Example 3. SuperPLDs Modulate PA-Dependent Signaling Pathways

To establish the general ability of superPLDs to generate physiologically active PA pools, optogenetic versions of superPLD were assessed for modulation of three different PA-dependent signaling pathways. First, it was confirmed that PA made at the plasma membrane by superPLDx30 can attenuate Hippo growth restriction pathway by triggering translocation of Yes-associated protein (YAP) from the cytosol to the nucleus in serum-starved cells (FIG. 8A-B), as previously shown for the WT form of optoPLD20.

Figures 9A, 9B, 9C:
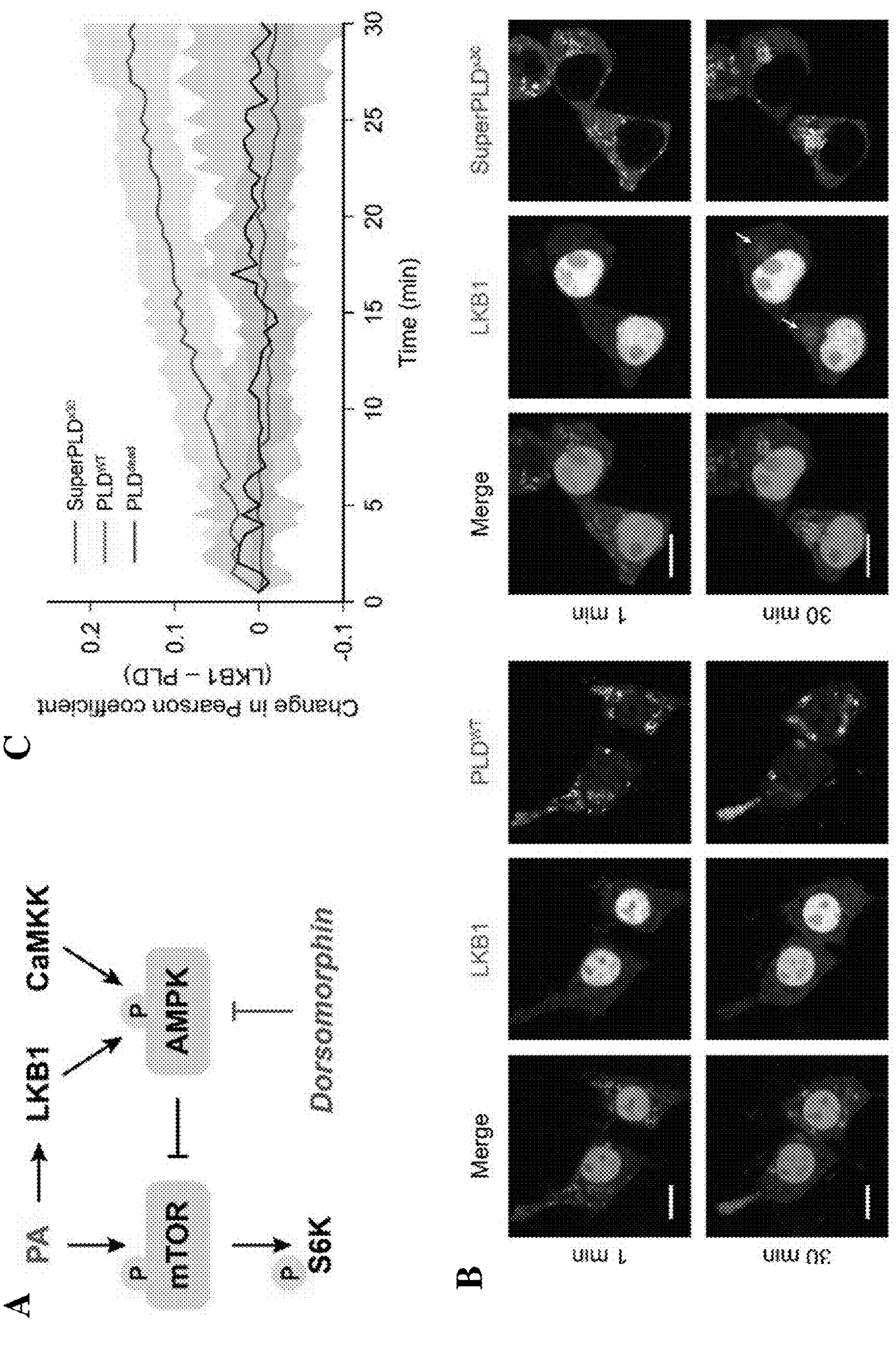

In addition to Hippo signaling, PA can also regulate two additional pathways related to nutrient sensing and cell growth: mammalian target of rapamycin (mTOR) signaling and AMP-activated protein kinase (AMPK) signaling. PA binds to liver kinase B1 (LKB1), which phosphorylates AMPK to activate it; however, such effects counteract the direct stimulatory effect of PA on mTOR signaling due to crosstalk between AMPK and mTOR signaling (FIG. 6A). To verify this finding and assess the ability of optoPLDs to induce LKB1 translocation to PA-rich membranes, GFP-tagged LKB1 and optoPLDs were co-expressed in HEK 293T cells. Surprisingly, PA production on lysosomes by superPLD, but not by $PLD^{WT}$, was sufficient to trigger LKB1 recruitment to lysosomes, consistent with the reported LKB1-PA interaction (FIG. 9B-C).

Figures 9D, 9E:
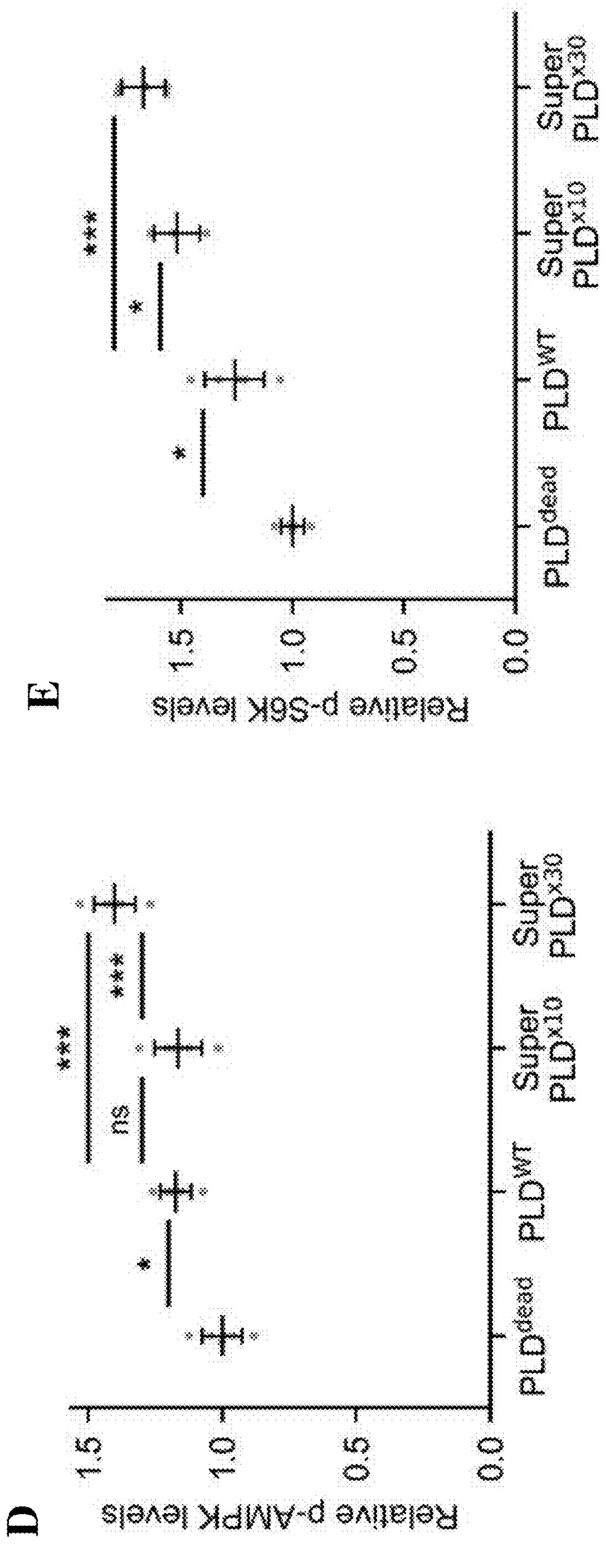

Then, HEK 293T cells were transduced with optoPLD using lentivirus and the effects on PA signaling were analyzed by Western blotting. In these experiments optoPLD were targeted to the plasma membrane as to mimic the localization of endogenous PLDs when stimulated. Although the cells had basal levels of AMPK phosphorylation, PA production by superPLD led to a significant increase in p-AMPK (FIG. 9D and FIG. 8C). Moreover, under conditions when AMPK signaling was inhibited with dorsomorphin to reduce crosstalk with mTOR signaling, PM-targeted superPLD increased phosphorylation of the mTOR effector S6 kinase (FIG. 9E and FIG. 8D). These results demonstrate that PA made by optoPLDs can independently activate mTOR and AMPK signaling, and importantly, superPLDs elicited a much stronger response in both cases. Collectively, these studies establish optogenetic superPLDs as generally useful tools for acute manipulation of mammalian PA-dependent signaling pathways.

Example 4. Several Mutations Cooperate to Enhance superPLD Activity

Next the mutations that led to increased PLD activity in the superPLDs were characterized. Sequencing analysis revealed that each superPLD clone carried 6-10 mutations (FIG. 10A). In addition to the G429D mutation present in one of the two templates, the selection produced a few other mutations present in many superPLDs (A258T, G381V, and T450A). Generation of mutant PLDs containing some or all of these four mutations only produced modest improvements, in a multiplicative manner, over $PLD^{WT}$, suggesting likely founder effects for these common mutations (FIG. 10B).

Figures 11A, 11B, 11C, 11D:
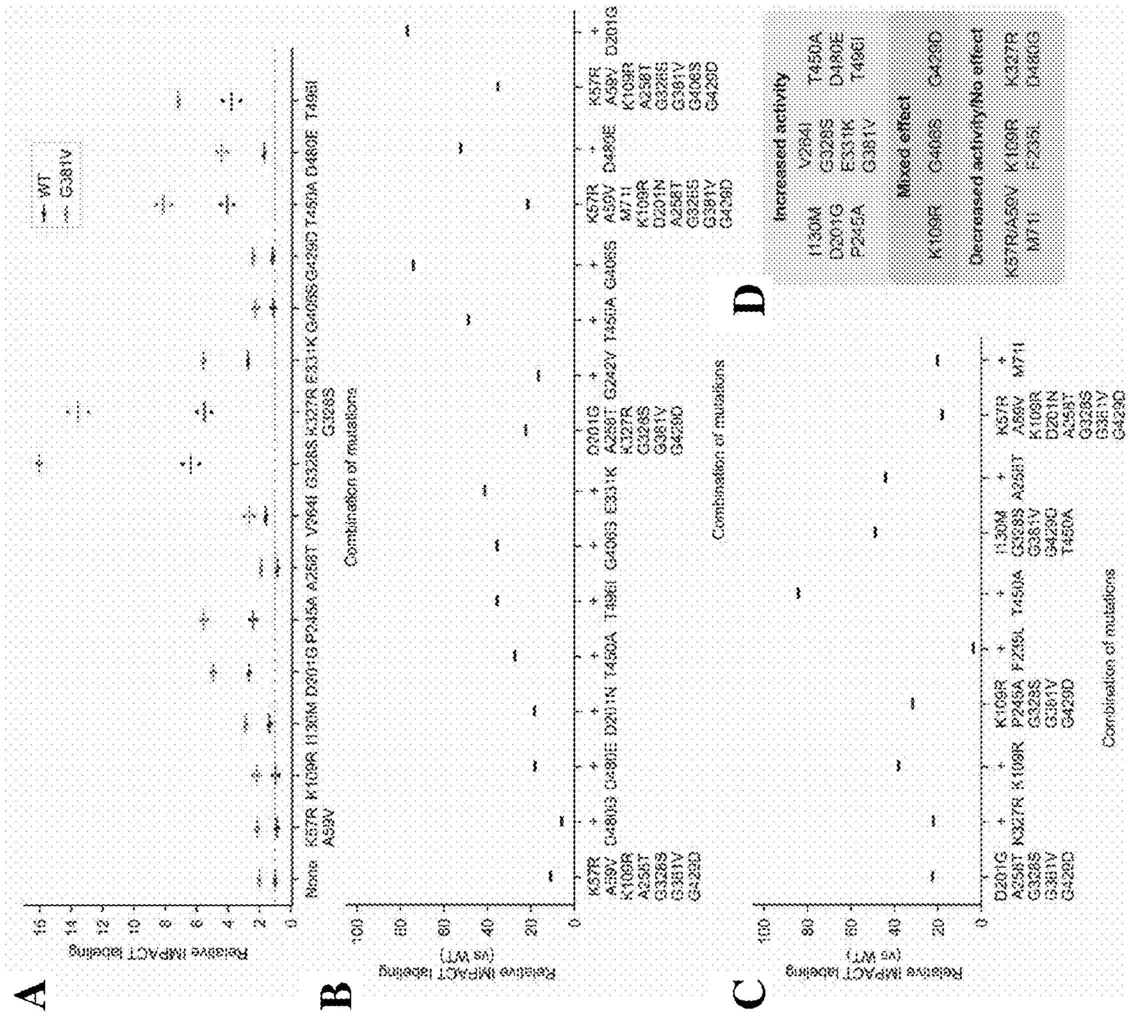

To dissect the effects of a broader set of mutations, individual point mutants were constructed in two backgrounds, WT and G381V, and assayed their activity (FIG. 11A). G381V was present in all superPLD clones. Individual mutations had variable effects on PLD activity, ranging from a slight decrease to an up to ~7-fold increase, with no magic bullet mutation of recapitulating the activity of the best superPLDs. A minority of mutations did not follow a multiplicative pattern, e.g., G406S, which did not increase PLD activity alone but caused a 3-fold increase in mutant backgrounds (FIG. 11A-C). Mutations were classified into three groups: (1) mutations that consistently increased PLD activity in various backgrounds, (2) mutations that consistently decreased PLD activity or had negligible effects, and (3) mutations that exhibited divergent effects on activity alone vs. in mutant backgrounds (FIG. 11D). Collectively, this mutational analysis established that the strong effects on superPLD activity are due to the cooperative effect of multiple mutations, most of which are far from the enzyme active site, based on the crystal structure of $PLD^{WT}$.

Example 5. X-Ray Analysis of superPLD Reveals an Expanded Active Site

Figures 12A, 12B, 12C, 12D, 12E, 12F:
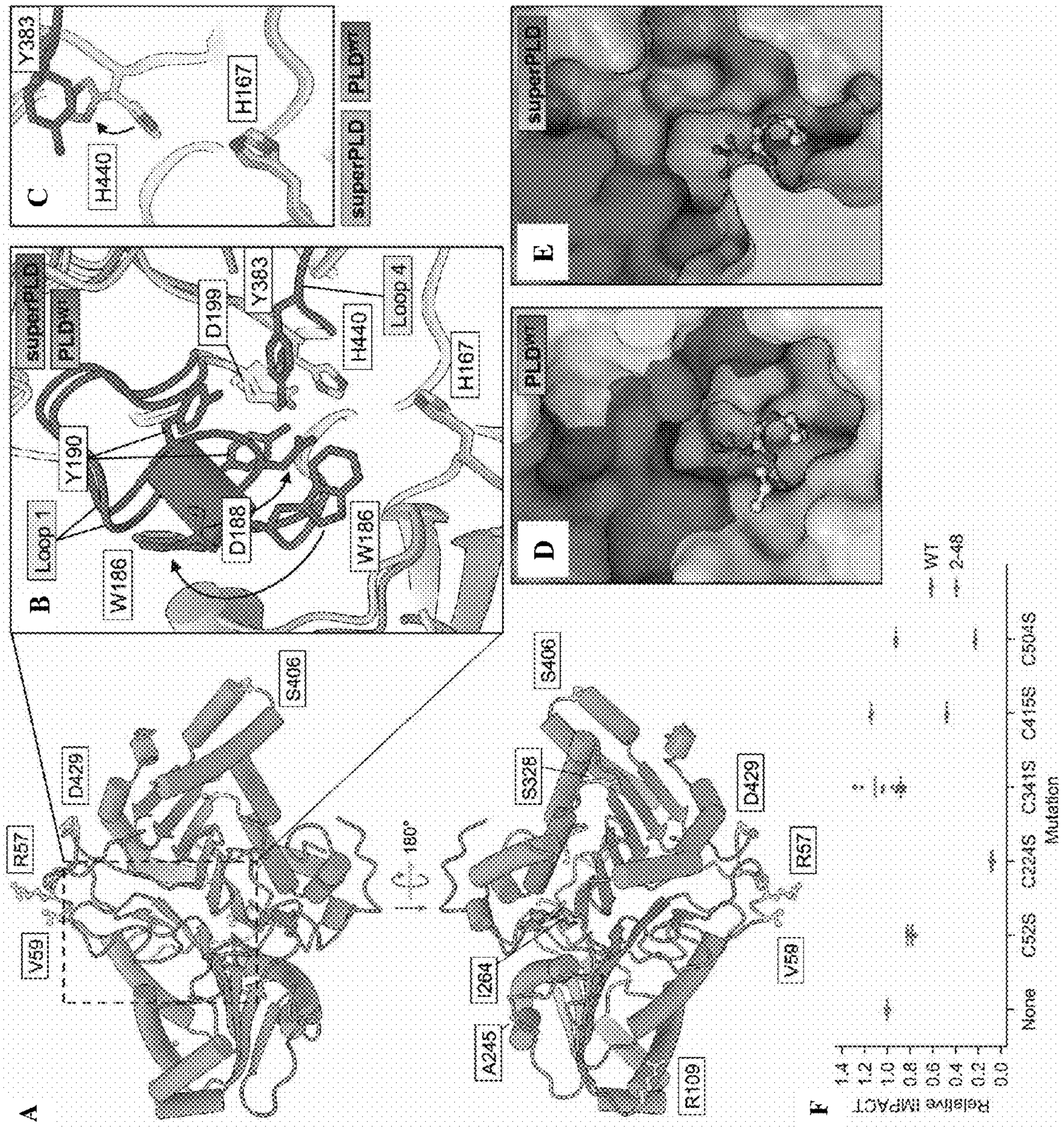
Figures 13A, 13B, 13C, 13D:
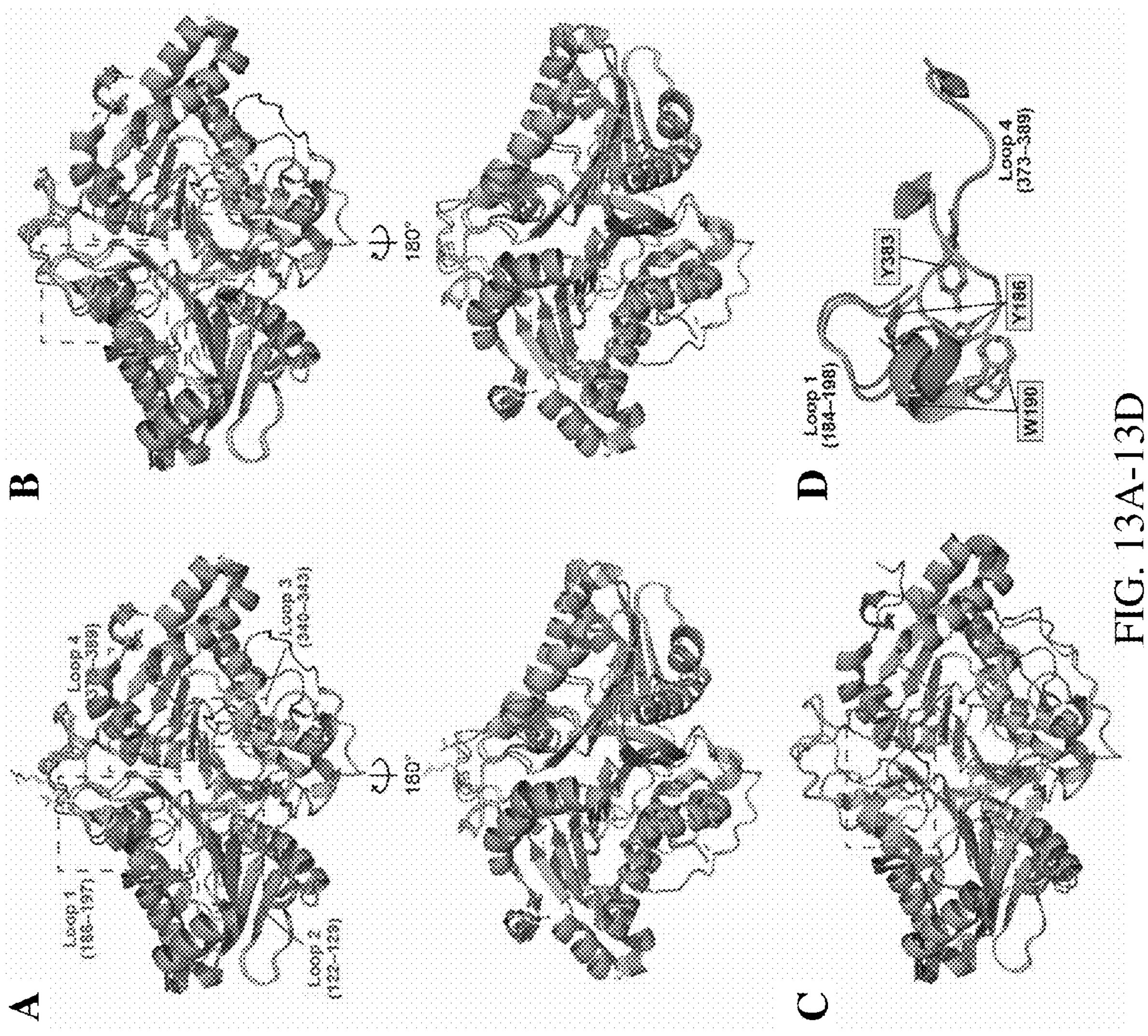

Next, the 3D structure of superPLDs and possible effects on mechanism were investigated. X-ray crystallography was performed on the two most active mutants, 2-48 (SEQ ID NO: 2) and 2-23 (SEQ ID NO: 3), with structures determined at resolutions of 1.85 and 1.91 Å, respectively (FIG. 12 and FIG. 13A-B). Despite sharing only five out of nine mutations, the two superPLDs had nearly identical structures. When compared to the $PLD^{WT}$, the three structures were largely similar. However, there were major differences in four flexible loops that form the entry of the active site (FIG. 13). In the superPLD structures, two flexible loops near the lipid head group binding site (loops 1 and 4) were farther away from the active site, causing a wider opening than that of $PLD^{WT}$. Additionally, the two loops closer to the lipid acyl tail binding site (loops 2 and 3) were slightly closer to the active site compared to their positions in $PLD^{WT}$. Importantly, the positions of three bulky aromatic residues within loops 1 and 4 (W186, Y190 and Y383) were substantially shifted in the superPLD structures, creating extra space in the catalytic pocket (FIG. 12A-E; note that Y383 is not resolved but its movement is inferred by examining the position of H440, which occupies the position occupied by Y383 in the $PLD^{WT}$ structure). Overall, the changes to loops 1-4 are important factors that lead to an expanded catalytic pocket where the lipid head group binds. This expanded catalytic pocket enables greater access of water and alcohols to the active site, contributing to the increased activity of superPLDs.

Figures 14A, 14B, 14C, 14D, 14E:
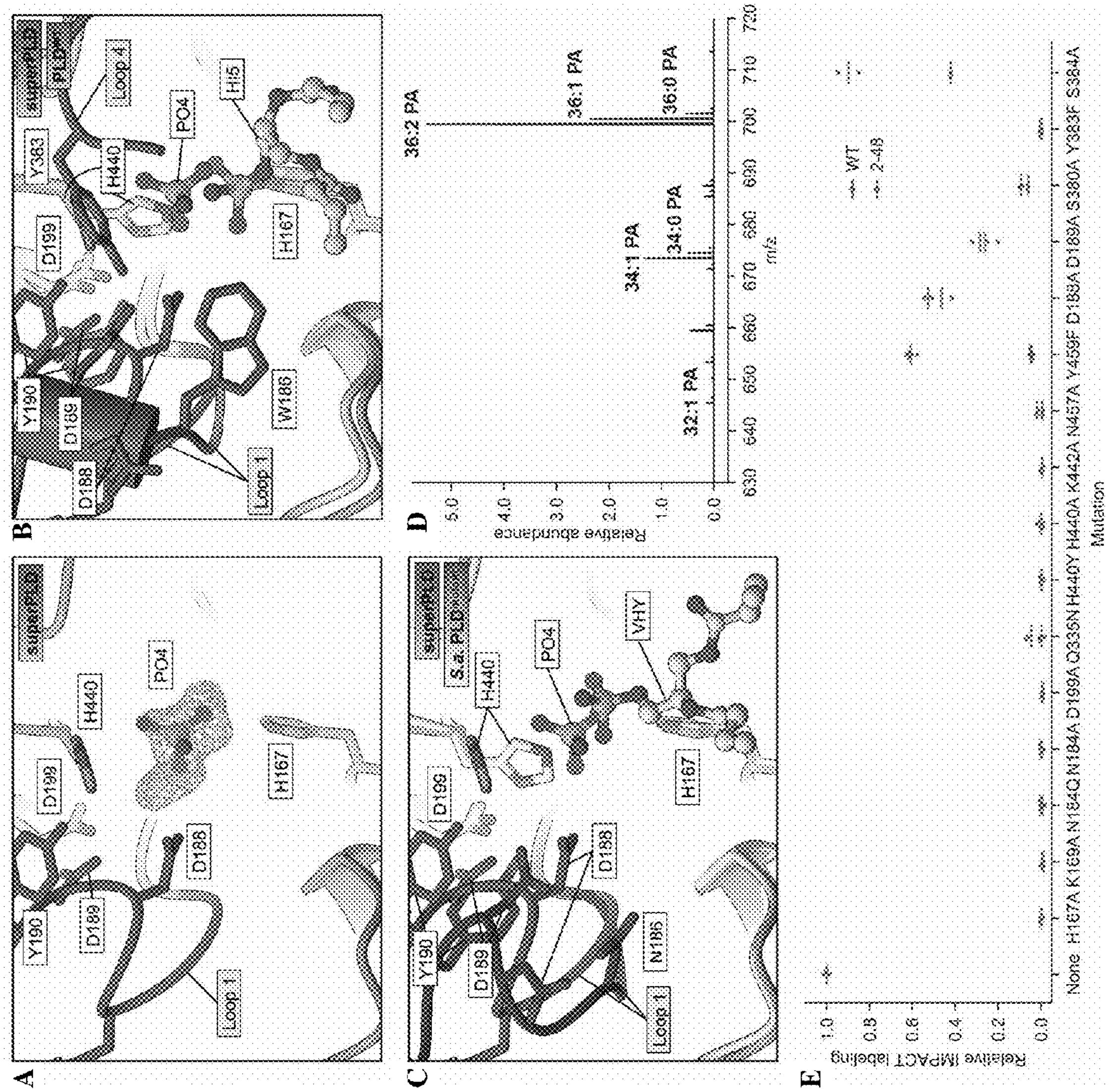

Another difference between superPLD and $PLD^{WT}$ inside the catalytic pocket was the orientation of H440. The H440 was flipped away from the active site in the superPLD structures relative to its position in the $PLD^{WT}$ structure (FIG. 12C). H440 directly participates in the reaction mechanism as a general acid/base catalyst along with the catalytic nucleophile H167. As such, the flipped position of H440 most likely represents the post-catalytic form of superPLD. Consistent with this, superPLD was found to co-purify with its product PA with the electron density of the glycerophosphate head group located between H167 and H440 yet at distances too far from either histidine residue for any productive catalysis (FIG. 14A-D). Mutational analysis of superPLD confirmed that residues known to be important for catalysis in $PLD^{WT}$ were equally important in superPLD, indicating that superPLD most likely shares the similar ligand-binding site as $PLD^{WT}$ in its active form (FIG. 14E).

Figures 15A, 15B, 15C, 15D, 15E, 15F, 15G:
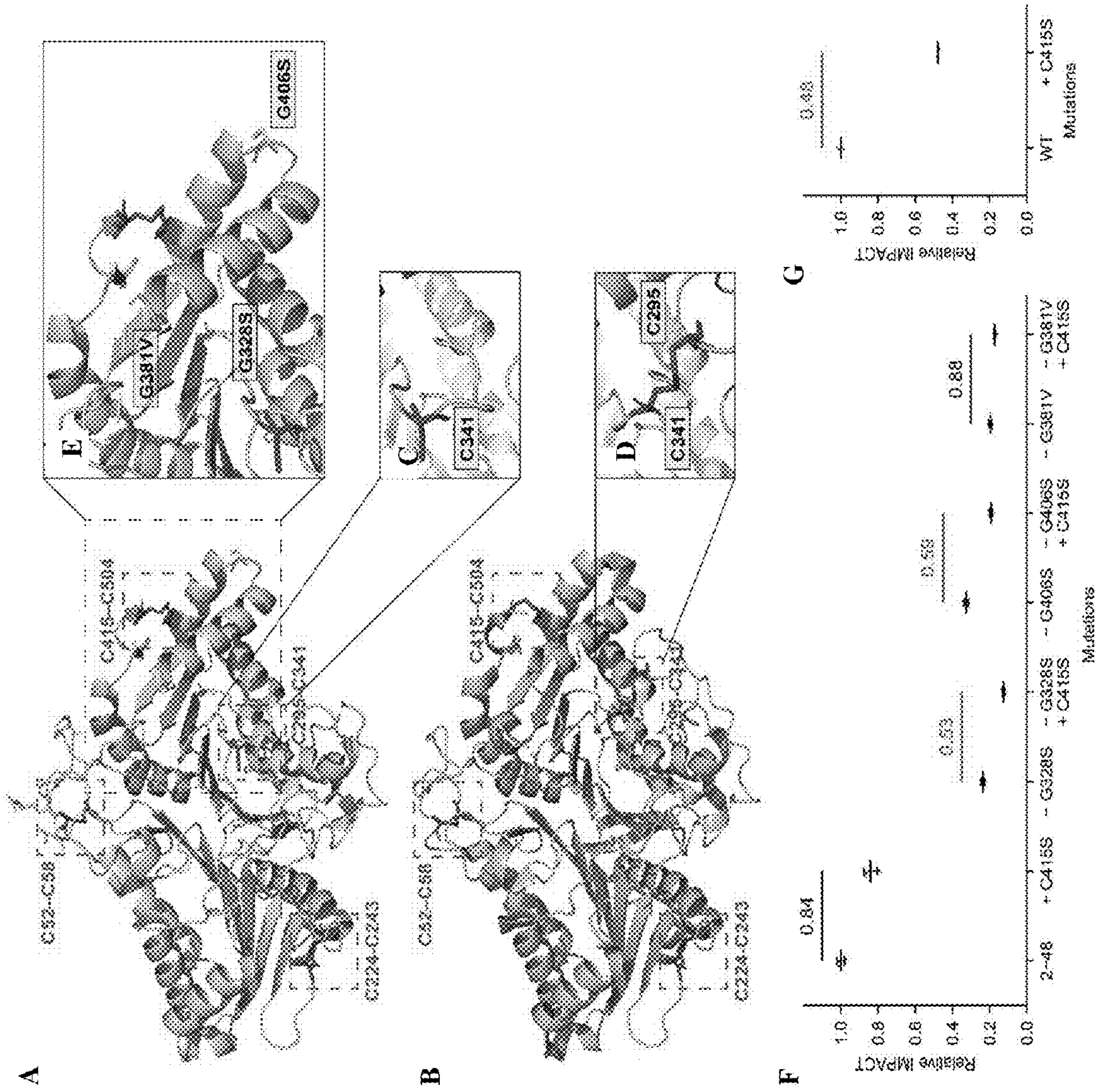

Lastly, the structural and mutational analysis revealed that superPLD was less reliant upon its four intramolecular disulfide bonds than $PLD^{WT}$. First, the C295-C341 disulfide bond present in $PLD^{WT}$ was absent in superPLD (FIG. 15A-D). Second, mutagenesis revealed that superPLD retained its activity much better than $PLD^{WT}$ when the C415-C504 disulfide bond was removed (FIG. 12F). Interestingly, the most active superPLDs (2-23 and 2-48) contained two nearby Gly-to-Ser mutations in short unstructured turns or loops adjacent to helices or sheets (G328S and G406S). These mutations might favor folding via interstrand contacts, even in the absence of covalent crosslinking provided by the disulfide, due to reduced entropy from a more restricted conformational space (FIG. 15E). Indeed, reversion of those residues to Gly within the superPLD background rendered the enzyme equally sensitive to C415S mutation as $PLD^{WT}$ (FIG. 15F-G). Collectively, these analyses point to possible sources of the increased cellular activity of superPLDs and highlight the utility of the mammalian cell-based activity-dependent directed evolution platform for generating superPLDs optimized for use for membrane editing in the reductive environment of cytosol-facing membranes in mammalian cells.

General Methodologies

Mammalian Cell Culture, Transfection, and Lentiviral Transduction

Cells were grown in DMEM (Corning) supplemented with 10% FBS (Corning), 1% penicillin/streptomycin (Corning), and 1 mM sodium pyruvate (Thermo Fisher) at 37° C. in a 5% $CO_2$ atmosphere. For poly-L-lysine pretreatment, cell plates were treated with 0.1 mg/mL poly-L-lysine (Sigma Aldrich; P2636) in PBS for 1-12 h at 37° C., followed by triple rinses with autoclaved deionized water.

For transient transfection, HEK 293T cells were transfected using Lipofectamine 2000 (Invitrogen; 11668019) following the manufacturer's protocol. Briefly, cells were incubated in regular DMEM media containing plasmids pre-mixed with Lipofectamine 2000 (0.3 μg optoPLD plasmid and 0.75 μL Lipofectamine 2000 per well for a 24-well plate), and the cells were incubated for 20-24 h before being labeled and analyzed.

For lentivirus production, HEK 293TN cells seeded on a 6-well plate were incubated in Transfectagro (Corning) supplemented with 10% FBS containing plasmids premixed with Lipofectamine 2000 (0.5 μg envelope plasmid, 1 μg packaging plasmid, 1.5 μg optoPLD plasmid, and 6 μL Lipofectamine 2000 per well for a 6-well plate). 8 h after transfection, the transfection media was replaced with regular DMEM media, and media were collected 24 h and 48 h after transfection to obtain virus-containing media. For lentiviral transduction, HEK 293T cells seeded on a 6-well plate (pre-treated with poly-L-lysine) were incubated in 1.5 mL virus-containing media supplemented with 0.5 mL fresh media and 0.8 μg/mL polybrene (Millipore Sigma). The 6-well plate was covered with aluminum foil to keep cells in the dark. After 24 h, virus-containing media was replaced with fresh DMEM media, and cells were incubated in the dark for another 24 h before being labeled and sorted (details in "IMPACT labeling and cell sorting" section).

Generation of optoPLD Libraries and Mutants

Libraries of optoPLD mutants were generated by error-prone PCR as described previously in Angelini, A. et al. Protein Engineering and Selection Using Yeast Surface Display. in Yeast Surface Display: Methods, Protocols, and Applications (ed. Liu, B.) 3-36 (Springer, 2015). Briefly, 100 ng of the template DNA was amplified with 0.5 μM forward and reverse primers (BamHI-PLD-S and EcoRI-PLD-AS), 200 μM dNTPs mix, 2 μM 8-oxo-dGTP (TriLink BioTechnologies, N-2034), 2 μM dPTP (TriLink BioTechnologies; N-2037), and 2.5 U Taq polymerase in Thermopol Reaction Buffer (New England Biolabs; B9004S). The PCR products were then gel purified and re-amplified for another 25 cycles under normal PCR conditions using the same primers. The second PCR products were digested using BamHI/EcoRI and cloned into optoPLD lentiviral vector (pCDH-CRY2-mCh-PLD-P2A-CIBN-CAAX) digested using the same restriction enzymes. The ligated product was transformed into DH5a *E. coli*, and the grown colonies were scraped and subjected to plasmid extraction. The resulting optoPLD plasmids were used to transfect HEK 293TN cells for lentivirus production (details in "Mammalian cell culture, transfection, and lentiviral transduction" section).

For introducing site-specific mutations to PLD, N-terminal and C-terminal fragments of PLD were amplified using a BamHI-PLD-S primer and a reverse mutagenizing primer containing a desired mutation (Table 1) for the N-terminal fragment, and EcoRI-PLD-AS primer and a forward mutagenizing primer (Table 1) for the C-terminal fragment. The two fragments were then stitched together using overlap-extension PCR to obtain the mutagenized PLD, which was subsequently cloned into an optoPLD transient expression vector (pCDNA3-CRY2-mCh-PLD-P2A-CIBN-CAAX) using BamHI and EcoRI cut sites.

Setup for Optogenetics Experiments

A homemade light box was built by attaching four strips of dimmable, 12 V blue-LED tape light (1000Bulbs.com; 2835-60-IP65-B1203) on the inside of a Styrofoam box. For optogenetics experiments, the light box was placed inside the $CO_2$ incubator using an AC Outlet Power Bank (Omars; 24,000 mAh, 80 W) as a power supply. An outlet timer (BN-LINK) was used to switch the light on and off automatically to enable 3-s intervals of blue light in every 1 min.

IMPACT Labeling and Cell Sorting

PLD1/2 double knockout HEK 293T cells expressing optoPLD libraries were treated with 1-5 mM azidopropanol for 30 min at 37° C. in the presence of intermittent blue light illumination (3-s pulses every 1 min). After three rinses with PBS, cells were treated with 1 μM bicyclononyne-BODIPY fluorophore (BCN-BODIPY[56]) for 10 min at 37° C. Cells were again rinsed three times with PBS and incubated in DMEM media for 10 min at 37° C. to remove excess fluorophore. Cells were then trypsinized, resuspended in PBS, and sorted using a Sony MA900 Cell Sorter or a FACSAria Fusion Cell Sorter. Cells expressing optoPLD-$^{dead}$, a catalytically dead mutant (H167 Å), were similarly labeled and sorted as a negative control, and the population in cells expressing optoPLD libraries that showed higher signal than the negative control was collected. The collected cells were expanded, at which point cells were reseeded for another round of selection or subjected to genomic extraction. Flow cytometry plots and histograms showing sorting strategy and collected cell populations for each round of selection are shown in FIG. 3.

Genomic Extraction and Amplification of PLD Fragments

Genomic DNA was extracted from HEK 293T cells using a NucleoSpin Blood kit (Takara Bio; 740951) following the manufacturer's protocol. Briefly, cells were rinsed once with PBS and lysed, then the lysis was applied to the DNA-binding column. After rinsing and drying the column, 60 μL of water was applied to elute DNA. The eluate was used as a template for PCR reactions to amplify PLD fragments. For PCR reactions, 0.5-10 μL of template was amplified for 25 cycles under normal PCR conditions with BamHI-PLD-S and EcoRI-PLD-S primers for use with Taq polymerase or with BamHI-PLD-S and EcoRI-PLD-S primers for use with Phusion polymerase. The PCR products were digested and cloned into the optoPLD vector as described in "Generation of optoPLD libraries" section.

Directed Evolution of optoPLDs

For the first round of evolution, two optoPLD libraries were generated using $PLD^{WT}$ or $PLD^{G429D}$ (the G429D mutation exhibits modestly higher (~1.3-fold) activity than $PLD^{WT}$)[20] as the starting template. The optoPLD libraries were introduced into HEK 293T cells using lentiviral transduction, and cells expressing optoPLD libraries were labeled and sorted as described above in "IMPACT labeling and cell sorting" section. The sorted cells were expanded prior to another cycle of IMPACT labeling and cell sorting. After the second cycle of selection, cells were subjected to genomic extraction. PLD fragments were amplified from the extracted DNA using Taq polymerase to introduce more mutations and then cloned into optoPLD vector.

For the second and third rounds of evolution, the optoPLD libraries were generated using the product of the previous round of evolution as the template. For these rounds, Taq polymerase, which has lower fidelity and thus expected to introduce ~1 mutation per PLD, was used for amplification. Further mutations were added by error-prone PCR, and the libraries with and without error-prone PCR were combined. The generated optoPLD libraries were expressed in cells, and cells were labeled and sorted as described above. The sorted cells were subjected to two more cycles of selection, followed by genomic extraction and PLD amplification.

For the fourth and subsequent rounds of evolution, genomic DNA extracted from cells was amplified by Phusion polymerase to minimize the introduction of further mutations. The rest of the evolution was performed likewise.

After evolution, PLD mutants were cloned into an optoPLD transient expression vector (pCDNA-CRY2-mCherry-B-PLD-E-P2A-CIBN-CAAX) using BamHI and EcoRI cut sites. Each plasmid isolated from a single *E. coli* colony was analyzed by Sanger sequencing using seq-mChterm(112)-S and seq-CIBN(103)-AS primers to determine the mutations in each clone of PLD mutants.

Quantitative comparison of PLD activity using IMPACT

HEK 293T cells were transiently transfected with CRY2-mCh-PLD-P2A-CIBN-CAAX, where the PLD sequence contained indicated set of mutations, and cells were kept in dark for 18-24 h. For IMPACT labeling, cells were treated with 0.1-1 mM azidopropanol for 30 min at 37° C. in the presence of intermittent blue light illumination (3-s pulses every 1 min). After three rinses with PBS, cells were treated with 1 μM BCN-BODIPY for 10 min at 37° C., again rinsed three times with PBS, and incubated in DMEM media for 10 min at 37° C. Cells were then trypsinized and subjected to flow cytometry analysis using an Attune NxT flow cytometer to measure mCherry and BODIPY fluorescence, which correspond to optoPLD expression level and IMPACT labeling intensity, respectively. Cells expressing similar amounts of optoPLD were gated, and the average IMPACT signal in the gated population was used to compare PLD activity of different mutants (FIG. 3T).

Evaluation of Phosphatidic Acid Localization by Confocal Microscopy

Due to the large DNA size of CRY2-mCherry-PLD-P2A-CIBN-CAAX, which affected lentivirus production efficiency, CRY2-mCherry-PLD and CIBN-CAAX were packaged separately into lentivirus. pCDH-CRY2-mCherry-superPLD was prepared by cloning superPLD into an optoPLD lentiviral expression vector (pCDH-CRY2-mCherry-PLD) using BamHI and EcoRI cut sites. Lentivirus containing GFP-PASS, CRY2-mCherry-PLD, and CIBN-CAAX (for plasma membrane-targeted optoPLD) or p18-CIBN (lysosome-targeted optoPLD) were prepared as described in "Mammalian cell culture, transfection, and lentiviral transduction" section. Spinfection was used for efficient co-transduction of HEK 293T cells with the three lentivirus preparations. Briefly, cells were seeded on 35-mm glass-bottom imaging dishes (Matsunami Glass), and after the addition of lentivirus-containing media to cells, cells were centrifuged at 931 g for 2 h at 37° C. After spinfection, lentivirus-containing media was replaced with regular growth media, and cells were kept in the dark for 48 h before imaging.

For colocalization analysis with LysoView 633, HEK 293T cells transduced with GFP-PASS, CRY2-mCherry-PLD and p18-CIBN were prepared as described above, and IX LysoView 633 was added before the imaging. For evaluation of LKB1 localization, HEK 293T cells seeded on imaging dishes were transfected with GFP-LKB1 and p18-CIBN-P2A-CRY2-mCherry-PLD using Lipofectamine 2000, and cells were kept in the dark for 20 h before imaging.

Images were acquired every 1 min for 1 h at 37° C. using Zeiss Zen Blue 2.3 on a Zeiss LSM 800 confocal laser scanning microscope equipped with Plan Apochromat objectives (40×1.4 NA) and two GaAsP PMT detectors. Solid-state lasers (488, 561, and 640 nm) were used to excite GFP, mCherry, and LysoView 633, respectively, and the 488 nm laser irradiation also served as a stimulus for activating optoPLD recruitment to the plasma membrane or lysosomes. The colocalization between GFP-PASS/LKB1 and CRY2-mCherry-PLD was calculated for each transfected cell using Coloc 2 plugin on ImageJ.

PLD Purification Using Affinity and Size-Exclusion Chromatography

PLD construct was cloned into the pCAV4.1 vector (NusA-10×N-HRV3C (pCAV4.1)), which is a modified T7 expression vector containing an N-terminal 6×His-NusA tag followed by peptide sequence that is cleavable by the HRV 3C protease. Constructs were transformed into Rosetta 2 (DE3) or Rosetta-gami 2 (DE3) *E. coli*, grown at 37° C. in 2×1 L terrific broth media supplemented with chloramphenicol (25 μg/mL) and ampicillin (100 μg/mL) to an $OD_{600}$ of 0.8, and then induced with IPTG (0.1 mM) for 20 h at 18° C. Cells were harvested by centrifugation, resuspended in 50 mL bacterial lysis buffer (50 mM sodium phosphate, 500 mM NaCl, 10% glycerol, pH 7.5) supplemented with 5 mM β-mercaptoethanol (for Rosetta) and 0.5 mM phenylmethylsulfonyl fluoride (PMSF), and homogenized by using a Sonic Dismembrator (Fisherbrand Model 505). The cell lysate was centrifuged at 30,000 g for 30 min, and the supernatant was incubated with 2 mL TALON Metal Affinity Resin (Takara Bio) for 1 h at 4° C. with rotation. The resin was then loaded onto a disposable column (Bio-Rad) and rinsed for 5 times with 25 mL bacterial lysis buffer. After resuspending the washed resin in 5 mL bacterial lysis buffer, His-tagged HRV3C protease was added and the mixture was incubated overnight at 4° C. with rotation to elute PLD from the resin. The supernatant containing cleaved PLD was concentrated using an Amicon 0.5 mL 10 kDa molecular weight cutoff centrifugal filter. For crystallization and thermal stability analysis, further purification of PLD using size-exclusion chromatography was performed using an AKTA pure system equipped with a Superdex 200 Increase 10/300 GL column in 20 mM Tris-HCl (pH 8.0) and 150 mM NaCl.

In Vitro Kinetics Assays of PLD Activity

PLD activity was determined using the Amplex Red Phospholipase D Assay Kit following the manufacturer's protocol. Briefly, 100 μM Amplex Red, 2 U/mL horseradish peroxidase (HRP), 0.2 U/mL choline oxidase, and 0.02-0.4 mg/mL 1,2-dioleoyl-sn-glycero-3-phosphatidylcholine (DOPC; prepared 40 mg/mL in ethanol) were added to PBS (pH 7.4) to prepare a master mix solution. The solution was added to 10 ng/mL PLD to start the reaction, and fluorescence signal was measured during the incubation at 37° C. using a BioTek Synergy H1 Microplate Reader. The luminescence signal at the reaction endpoint, when all the DOPC was consumed, was used to convert luminescence signal (AU) to [product] (μM) for calculating $V_{max}$. $K_m$ and $k_{max}$ of the reaction were calculated based on the Michaelis-Menten equation.

Phospholipid Synthesis and Liquid Chromatography (LC)-Mass Spectrometry (MS) Analysis In 1.5-mL Safe-Lock Eppendorf tubes, 50 μM-2 M of alcohol and 0.1 μg of PLD were added to 100 μL PBS (pH 7.4). For ethanolamine, the pH was adjusted to pH 7.4 by addition of HCl. After addition of 0.8 mg of DOPC in 80 μL ethyl acetate, the tubes were placed in a plastic box and shaken vigorously in a 37° C. shaker for 1-24 h at 350 rpm. The reaction was quenched by adding 250 μL methanol, 125 μL acetic acid (20 mM in water), and 500 μL chloroform. The solution was mixed thoroughly by shaking vigorously for 5 min, and the tubes were centrifuged at high speed for 1 min. 10 μL aliquots of the bottom organic layer were collected and transferred into new tubes. Solutions were diluted, filtered, and subjected to high-resolution LC-MS analysis to quantify the concentrations of DOPC, dioleoyl phosphatidic acid (DOPA), and dioleoyl phosphatidyl alcohol (DOPAlc) in the sample. The obtained concentration was used to calculate the total amount of each compound in the reaction mixture, which was used to determine the percent yield for DOPA and DOPAlc.

LC-MS analysis was performed on an Agilent 6230 electrospray ionization-time-of-flight MS coupled to an Agilent 1260 HPLC equipped with a Luna 3 μm Silica LC Column (Phenomenex; 50×2 mm) using a binary gradient elution system where solvent A was chloroform/methanol/ammonium hydroxide (85:15:0.5) and solvent B was chloroform/methanol/water/ammonium hydroxide (60:34:5:0.5). Separation was achieved using a linear gradient from 100% A to 100% B over 10 min. Phospholipid species were detected using an Agilent Jet Stream source operating in positive or negative mode, acquiring in extended dynamic range from m/z 100-1700 at one spectrum per second; gas temperature: 325° C.; drying gas 12 L/min; nebulizer: 35 psig; fragmentor 300 V (for positive mode) and 250 V (for negative mode); sheath gas flow 12 L/min; Vcap 3000 V; nozzle voltage 500 V.

Thermal Stability Analysis

The thermal stability of $PLD^{WT}$ and superPLDs was determined as previously reported in Joiner, A. M. N. & Fromme, J. C., Structure 29, 859-872.e6 (2021). Briefly, $PLD^{WT}$ and superPLDs were diluted to 0.1 mg/mL final concentration in Tris-HCl buffer (10 mM, pH 8.0, 150 mM NaCl) containing SYPRO Orange (1:1000 dilution of 5000× concentrate). The fluorescence signal was measured while the temperature was slowly raised using a Roche LightCycler 480. Melting temperature (Tm) was determined by the temperature at which the fluorescence signal reached 50% of its maximum.

Chemical Stability Analysis

The chemical stabilities of $PLD^{WT}$ and superPLD (2-48) were determined by measuring the residual activity of PLD treated with urea. 1 μg/mL PLD was incubated in solutions of 0-4 M urea in PBS for 12 h at 37° C., after which the PLD activity was measured as described in "In vitro kinetics assays of PLD activity" section. The relative rate of reaction compared to 0 M urea (untreated) PLD was used for estimating the chemical stability.

Evaluation of YAP Localization by Immunofluorescence

HEK 293T cells seeded on cover glasses coated with poly-L-lysine were transfected with CRY2-mCherry-PLD-P2A-CIBN-CAAX, and cells were kept in dark for 16 h before being placed in a serum-starvation medium (DMEM supplemented with 1% penicillin/streptomycin without FBS). After 6 h of starvation, cells were stimulated for 1 h with intermittent blue light illumination (5-s pulses every 1 min), followed by cell fixation and immunostaining as described previously in Tei, R. & Baskin, J. M., J. Cell Biol. 219, (2020). Briefly, cells were fixed in 4% paraformaldehyde for 10 min at room temperature, followed by extraction in a solution of 0.5% Triton X-100 in PBS for 5 min. Cells were then blocked in a solution of 1% BSA and 0.1% Tween-20 in PBS (blocking buffer) for 30 min. Immunostaining was then performed by treating cells with a 1:100 dilution of anti-YAP antibody (Santa Cruz Biotechnology; sc-101199) in blocking buffer for 1 h, rinsing three times with 0.1% Tween-20 in PBS solution (PBS-T), treatment with a 1:1,000 dilution of anti-mouse-Alexa Fluor 488 antibody conjugate (Invitrogen; A-21202) in blocking buffer for 1 h, and rinsing three times with PBS-T. Cells were mounted on microscope slides using ProLong Diamond Antifade Mountant with DAPI (Thermo Fisher) and incubated overnight at room temperature in the dark. Image acquisition by laser-scanning confocal microscopy was performed as described above by using solid-state lasers (405, 488, and 561 nm) to excite DAPI, Alexa Fluor 488, and mCherry, respectively.

Quantification of p-AMPK and p-S6K by Western Blotting

HEK 293T cells were transduced with CRY2-mCherry-PLD and CIBN-CAAX using lentivirus and spinfection as described in "Evaluation of phosphatidic acid localization by confocal microscopy" section. Cells were incubated with either 10 μM STO-609 (CaMKK inhibitor; for AMPK signaling assay) for 6 h or 10 μM dorsomorphin (AMPK inhibitor; for mTOR signaling assay) for 1 h at 37° C., followed by 30 min stimulation with intermittent blue light illumination (5-s pulses every 1 min). Cells were then lysed with RIPA lysis buffer supplemented with protease and phosphatase inhibitors (50 mM Tris-HCl, pH 7.4, 150 mM NaCl, 1% Triton-X, 0.5% sodium deoxycholate, 0.1% SDS, 1 mM EDTA, 1× cOmplete™ Protease Inhibitor, 17.5 mM beta-glycerophosphate, 20 mM sodium fluoride, 1 mM activated sodium orthovanadate, 5 mM sodium pyrophosphate). After sonication and centrifugation, the lysate supernatants were mixed with 6× Laemmli sample buffer to prepare the sample for Western blotting. The membrane was blotted with antibodies for phospho-AMPKα (Thr172) (Cell Signaling Technology; #2535), phospho-p70 S6 kinase (Thr389) (Cell Signaling Technology; #9205), p70 S6 kinase (Santa Cruz Biotechnology; sc-8418), mCherry (Novus Biologicals; NBP1-96752), or actin (MP Biomedicals; 08691001), with detection by chemiluminescence using the Clarity Western ECL Substrate (Bio-Rad) and acquisition on a Bio-Rad ChemiDoc MP System.

Quantification of Substrate Conversion by superPLD in Cells

HEK 293T cells seeded on 12-well plates were transduced with CRY2-mCherry-PLD and CIBN-CAAX using lentivirus and spinfection as described above. Cells were incubated with 0.5-2% ethanol, which should be sufficient to inhibit most of PLD hydrolysis activity, for 30 min with intermittent blue light illumination. Cells were then rinsed with PBS three times and subjected to lipid extraction. For lipid extraction, cells were scraped in 250 μL methanol, 125 μL acetic acid (20 mM in water), and 100 μL PBS. The cell suspension was transferred into a 1.5-mL centrifuge tube, and the lipids were extracted and subjected to LC-MS analysis as described in "Phospholipid synthesis and LC-MS analysis" section.

Crystallization of superPLD

Crystals for superPLD (2-48 mutant) were obtained by mixing 1 μL of purified protein at 2.5 mg/mL with 1 μL of well solution containing 21% PEG, 0.15 M $Li_2SO_4$, and citrate-NaOH (pH 4.4) and equilibrated against 200 μL of well solution at 18° C. Crystals grew within 5-7 d. Single crystals were harvested and soaked in the well solution supplemented with 10% ethylene glycerol for 10 s before plunge freezing in liquid $N_2$. Crystals for the 2-23 mutant were obtained by mixing 1 μL of purified protein at 2.5 mg/mL with 1 μL of well solution containing 19% PEG, 0.15 M $Li_2SO_4$, citrate-NaOH (pH 4.15) and equilibrated against 200 μL of well solution at 18° C. Crystals grew within 5-7 d. Single crystals were harvested and soaked in the well solution supplemented with 10% ethylene glycol for 10 s before plunge freezing in liquid $N_2$.

X-Ray Diffraction Data Collection, Processing and Model Building

Diffraction experiments were conducted at beamline 24-ID-E of the Advanced Photon Source (APS) and beamline ID7B2 of the Cornell High Energy Synchrotron Source (CHESS). Diffraction data sets were collected at 100 K and processed using XDS. Crystals of superPLDs, 2-48 mutant and 2-23 mutant diffracted to 1.85 Aand 1.9 Å, respectively. The crystal structure of $PLD^{WT}$ (PDB ID 1V0Y) was used to obtain phasing information using molecular replacement using Phaser in PHENIX. The models were subjected to iterative rounds of manual re-building using COOT followed by refinement in PHENIX. Electron density was observed in the active site that likely corresponds to a bound reaction intermediate. Based on previously reported structures of PLD in complex with reaction intermediates (PDB 7JRU and 7JRV), a phosphate moiety was modelled in part of this density. Note that the density was not clear enough to model the glycerol back bone and the acyl-chains, so these groups were omitted from the model. Final refinement and validation statistics for the models are reported in Table 2.

Statistical Analysis

Statistical significance was calculated using one-way ANOVA, followed by Tukey's HSD test using the "statsmodel" Python package. *, $p<0.05$; , $p<0.01$; *, $p<0.001$.

TABLE 2

| | SuperPLD (2-23) | SuperPLD (2-48) |
|---|---|---|
| Data collection | | |
| Space group | P21 21 21 | P21 21 21 |
| Cell dimensions | | |
| a, b, c (Å) | 72.725, 73, 87.482 | 72.828, 73.254, 87.19 |
| α, β, γ (°) | 90, 90, 90 | 90, 90, 90 |
| Wavelength (Å) | | |
| Resolution (Å) | 56.05-1.905 (1.973-1.905) | 56.09-1.852 (1.918-1.852) |
| $R_{meas}$ (%) | 11.9 (69.6) | 12.25 (95.86) |
| I/σ (I) | 12.1 (2.0) | 13.55 (2.35) |
| Completeness (%) | 98.8 (94.9) | 99.15 (91.44) |
| Redundancy | 5.5 (5.4) | 13.1 (12.4) |
| $CC_{1/2}$ | 0.992 (0.820) | 0.998 (0.879) |
| Refinement | | |
| Resolution (Å) | 56.05-1.905 | 56.09-1.852 |
| No. of reflections | 36421 (3442) | 40025 (3612) |
| Completeness (%) | 98.8 | 99.15 |
| $R_{work}/R_{free}$ (%) | 17.72/23.18 | 17.29/21.68 |
| No. of non-hydrogen atoms | 3842 | 3920 |
| Protein | 3624 | 3631 |
| Ligand | 5 | 5 |
| Water | 213 | 284 |
| Wilson B-value ($Å^2$) | 34.1 | 28.98 |
| Mean B-value ($Å^2$) | 44.28 | 36.59 |
| Protein | 44.21 | 36.29 |
| Ligand | 88.94 | 84.09 |
| Water | 44.4 | 39.58 |
| Molprobity clash score | 4.46 | 5.42 |

TABLE 2-continued

| | | SuperPLD (2-23) | SuperPLD (2-48) |
|---|---|---|---|
| Ramachandran | Favored (%) | 96.2 | 95.78 |
| | Allowed (%) | 2.95 | 3.38 |
| | Outliers (%) | 0.84 | 0.84 |
| RMS deviations | Bonds (Å) | 0.011 | 0.01 |
| | Angles (°) | 1.12 | 1.08 |

TABLE 1

| SEQ ID NO | Name of Primer | Primer Sequence |
|---|---|---|
| 72 | K109R-AS | CTTATTGCCTCTAGCTGCGGACTCCTTC |
| 73 | K109R-S | CCGCAGCTAGAGGCAATAAGTTGAAAGTTAGG |
| 74 | I130M-AS | CATGAATGTAATGCCTTCCAAGTATAGGGACG |
| 75 | I130M-S | ACTTGGAAGGCATTACATTCATGTGGTAGACGG |
| 76 | H167A-AS | GATTTTGCTGGCGTTCCAGGAG |
| 77 | H167A-S | CTGGAACGCCAGCAAAATCTTGG |
| 78 | K169A-AS | CCAAGATGGCGCTATGGTTCCAG |
| 79 | K169A-S | CCATAGCGCCATCTTGGTTGTAGAC |
| 80 | N184A-AS | CTTCCAGCTGGCTATTCCACCAGTAAG |
| 81 | N184A-S | GTGGAATAGCCAGCTGGAAGGATG |
| 82 | N184Q-AS | CTTCCAGCTCTGTATTCCACCAGTAAG |
| 83 | N184Q-S | GTGGAATACAGAGCTGGAAGGATG |
| 84 | D188A-AS | AAGTAATCGGCCTTCCAGCTATTTATTCC |
| 85 | D188A-S | GCTGGAAGGCCGATTACTTGGATAC |
| 86 | D189A-AS | ATCCAAGTAGGCATCCTTCCAGC |
| 87 | D189A-S | GGAAGGATGCCTACTTGGATACTACTC |
| 88 | D199A-AS | GATCAACGGCAGACACTGGATGAG |
| 89 | D199A-S | CAGTGTCTGCCGTTGATCTTGCAC |
| 90 | D201G-AS | TCTGATGTTGGTCTTGCACTGACCGGACC |
| 91 | D201G-S | CAGTGCAAGACCAACATCAGACACTGGATGAG |
| 92 | C224S-AS | CTTGTTTTGGGAGGTCCATGTCCAC |
| 93 | C224S-S | CATGGACCTCCCAAAACAAGAGTAAC |
| 94 | P245A-AS | GCATAGTGGCCATGCACCCTGCGTTG |
| 95 | P245A-S | GGTGCATGGCCACTATGCATAAAGATACAAACC |
| 96 | A258T-AS | CCCGGTGGTAGGTGATGCCTTGGGG |
| 97 | A258T-S | CATCACCTACCACCGGGAATGTCCC |
| 98 | V264I-AS | GAATGTCCCAATAATAGCCGTTGGAGGGT |
| 99 | V264I-S | ACGGCTATTATTGGGACATTCCCGGTG |
| 100 | K327R/G328S-AS | CAATGTGACTCCTTGCTGAAGCAACAAGAGC |
| 101 | K327R/G328S-S | CTTCAGCAAGGAGTCACATTGAAATATCTCAGCAG |
| 102 | G328S/E331K-AS | CCTGCTGAGATATTTTAATGTGACTTTTTGCTGAAGC |
| 103 | G328S-AS | CAATGTGACTTTTTGCTGAAGCAACAAGAG |

TABLE 1-continued

| SEQ ID NO | Name of Primer | Primer Sequence |
|---|---|---|
| 104 | G328S-S | CTTCAGCAAAAAGTCACATTGAAATATCTCAGCAG |
| 105 | E331K-AS | CCTGCTGAGATATTTTAATGTGACCTTTTGCTGAAGC |
| 106 | E331K-S | GTCACATTAAAATATCTCAGCAGGATTTGAAC |
| 107 | Q335N-AS | CGTTCAAATCGTTCTGAGATATTTCAATG |
| 108 | Q335N-S | GAAATATCTCAGAACGATTTGAACGCTAC |
| 109 | C341S-AS | AGGGTGGAGATGTAGCGTTC |
| 110 | C341S-S | CGCTACATCTCCACCCTTGCC |
| 111 | S380A-AS | CCCCCAGCGCCCACTGC |
| 112 | S380A-G381V-AS | ACCCACAGCGCCCACTGC |
| 113 | S380A-G381V-S | GTGGGCGCTGTGGGTTACAG |
| 114 | S380A-S | GTGGGCGCTGGGGGTTACA |
| 115 | V381G-AS | GTAACCCCCACTGCCCACTGCGC |
| 116 | V381G-S | GGGCAGTGGGGGTTACAGCCAAATAAAATC |
| 117 | G381V-S384A-AS | TATTTGGGCGTAACCCACACTGC |
| 118 | G381V-S384A-S | GTGGGTTACGCCCAAATAAAATCACTTA |
| 119 | G381V-Y383F-AS | TTGGCTGGCACCCACACTGC |
| 120 | G381V-Y383F-S | GTGGGTGCCAGCCAAATAAAATCAC |
| 121 | Y383F-AS | TGGCTGGCACCCCCACTGC |
| 122 | Y383F-S | GGGGGTGCCAGCCAAATAAAATC |
| 123 | S384A-AS | TTTGGGCGTAACCCCCACTGC |
| 124 | S384A-S | GGGGGTTACGCCCAAATAAAATCAC |
| 125 | G406S-AS | CCCATTTGTCGTTGGGGGAGGATCTAAAG |
| 126 | G406S-S | CCCCAACGACAAATGGGCAGACGGGC |
| 127 | C415S-AS | GCAAATTGCTAGACATTGCAGTTTTG |
| 128 | C415S-S | CTGCAATGTCTAGCAATTTGCAGC |
| 129 | G429D-AS | CCCATTTGTCGTTGGGGGAGGATCTAAAG |
| 130 | G429D-S | CCCCAACGACAAATGGGCAGACGGGC |
| 131 | H440A-AS | CAACTTATGGGCTTGGGCATAAGGATG |
| 132 | H440A-S | CTTATGCCCAAGCCCATAAGTTGGTTTC |
| 133 | H440W-AS | CAACTTATGCCATTGGGCATAAGGATG |
| 134 | H440W-S | CTTATGCCCAATGGCATAAGTTGGTTTC |
| 135 | H440Y-AS | CAACTTATGGTATTGGGCATAAGGATG |
| 136 | H440Y-S | CTTATGCCCAATACCATAAGTTGGTTTC |
| 137 | K442A-AS | GAAACCAAGGCATGGTGTTGGG |
| 138 | K442A-S | AACACCATGCCTTGGTTTCCGTC |
| 139 | T450A-AS | CGATATAAAATGCGGATGAGTCGACGGAAAC |
| 140 | T450A-S | GACTCATCCGCATTTTATATCGGTTCAAAAAATTTGTAC |
| 141 | N457A-AS | GATGGGTACAAGGCTTTTGAACCG |
| 142 | N457A-S | GTTCAAAAGCCTTGTACCCATCCTG |

TABLE 1-continued

| SEQ ID NO | Name of Primer | Primer Sequence |
|---|---|---|
| 143 | Y459F-AS | CCAGGATGGGAACAAATTTTTTGAAC |
| 144 | Y459F-S | CAAAAAATTTGTTCCCATCCTGGCTG |
| 145 | D480E-AS | CAATTTGGCCTCCAGTTGCTTGGCAGC |
| 146 | D480E-S | GCAACTGGAGGCCAAATTGCTTGACCCTC |
| 147 | D480G-AS | AGCAACTGGGTGCCAAATTGCTTGACCCTC |
| 148 | D480G-S | CAATTTGGCACCCAGTTGCTTGGCAGC |
| 149 | T496I-AS | GTAATCCACTATTGCAGTCTCCTGTGAGTAC |
| 150 | T496I-S | GAGACTGCAATAGTGGATTACGCAAGAGGAAT |
| 151 | C52S-AS | CGCCCCAAGATCCTGGGG |
| 152 | C52S-S | CCAGGATCTTGGGGCGATG |
| 153 | K57R/A59V-AS | GATGATAGATGCGTTGACAGAGTTGGGACAAAAAG |
| 154 | K57R/A59V-S | TCTGTCAACGCATCTATCATCGCCCCAACATCCTG |
| 155 | C504S-AS | gtcaGAATTCAGCGTTGGAGATTCCTCTTGCG |

TABLE 3

| SEQ ID NO: | PLD Mutant Identification (Clone) |
|---|---|
| 2 | Mutant 2-48 |
| 3 | Mutant 2-23 |
| 4 | Mutant 2-54 |
| 5 | Mutant 2-55 |
| 6 | Mutant 2-115 |
| 7 | Mutant 2-15 |
| 8 | Mutant 1-35 |
| 9 | Mutant 2-87 |
| 10 | Mutant 1-27 |
| 11 | Mutant 2-26 |
| 12 | Mutant 2-67 |
| 13 | Mutant 2-74 |
| 14 | Mutant 2-51 |
| 15 | Mutant 1-17 |
| 16 | Mutant 2-33 |
| 17 | Mutant 2-25 |
| 18 | Mutant 2-7141 |
| 19 | Mutant 2-152 |
| 20 | Mutant 2-114 |
| 21 | Mutant 2-140 |
| 22 | Mutant 2-135 |
| 23 | Mutant 2-19 |
| 24 | Mutant 2-4 |
| 25 | Mutant 2-1 |
| 26 | Mutant 2-99 |
| 27 | Mutant 2-130 |
| 28 | Mutant 2-70 |
| 29 | Mutant 1-28 |
| 30 | Mutant 1-37 |
| 31 | Mutant 1-9 |
| 32 | Mutant 1-2 |
| 33 | Mutant 1-32 |
| 34 | Mutant 1-12 |
| 35 | Mutant 1-40 |
| 36 | Mutant 1-16 |
| 37 | Mutant 1-25 |
| 38 | Mutant 1-14 |
| 39 | Mutant 1-42 |
| 40 | Mutant 1-20 |
| 41 | Mutant 1-8 |
| 42 | Mutant 1-18 |
| 43 | Mutant 1-10 |

TABLE 3-continued

| SEQ ID NO: | PLD Mutant Identification (Clone) |
|---|---|
| 44 | Mutant 1-38 |
| 45 | Mutant 1-45 |
| 46 | Mutant 1-19 |
| 47 | Mutant 1-15 |
| 48 | Mutant 1-26 |
| 49 | Mutant 1-4 |
| 50 | Mutant 1-21 |
| 51 | Mutant 1-36 |
| 52 | Mutant 1-47 |
| 53 | Mutant 1-33 |
| 54 | Mutant 1-13 |
| 55 | Mutant 1-41 |
| 56 | Mutant 1-48 |
| 57 | Mutant 1-1 |
| 58 | Mutant 1-22 |
| 59 | Mutant 1-3 |
| 60 | Mutant 1-30 |
| 61 | Mutant 2-137 |
| 62 | Mutant 2-28 |
| 63 | Mutant 2-69 |
| 64 | Mutant 2-70 |
| 65 | Mutant 1-28 |
| 66 | Mutant 1-46 |
| 67 | Mutant 2-126 |
| 68 | Mutant 1-24 |
| 69 | Mutant 1-43 |
| 70 | Mutant 1-7 |
| 71 | Mutant 1-31 |

What is claimed:

1. A mutant Phospholipase D (PLD) enzyme comprising an amino acid sequence that varies from the amino acid sequence of a wild type PLD enzyme as set forth in SEQ ID NO: 1 in 6 to 10 substitutions;

wherein one of the substitutions is G381V;

wherein the additional substitutions are selected from the group consisting of S3T, Q13H, K34R, P42L, P42S, P42T, K57R, A59V, M71I, I130M, K133R, F163L, S185G, S198F, D201G, D201N, F235L, G242V, P245A, H248Y, K249R, A258T, P263S, V264I, K275R, K327R, G328S, E331K, N338Y, P345S, T395I, G406S, T412N, G429D, Q439K, T450A, D480G, D480E, Q492R, A495V, T496I, and C504Y; and wherein the mutant PLD enzyme exhibits a transphosphatidylation activity at least 2-fold higher as compared to the wild type PLD enzyme.

2. The mutant PLD enzyme of claim 1, wherein the mutant PLD enzyme exhibits a transphosphatidylation activity at least 10-fold higher as compared to the wild type PLD enzyme.

3. The mutant PLD enzyme of claim 1, wherein one of the additional substitutions is A258T.

4. The mutant PLD enzyme of claim 1, wherein one of the additional substitutions is G429D.

5. The mutant PLD enzyme of claim 1, wherein one of the additional substitutions is T450A.

6. The mutant PLD enzyme of claim 1, wherein the additional substitutions comprise K57R, A59V, K109R, P245A, V264I, G328S, G406S, and G429D.

7. The mutant PLD enzyme of claim 1, wherein the additional substitutions comprise I130M, P245A, G328S, G406S, and G429D.

8. The mutant PLD enzyme of claim 1, wherein the mutant PLD enzyme exhibits a transphosphatidylation activity at least 10-fold higher as compared to the wild type PLD enzyme; and wherein the transphosphatidylation activity is measured in cells.

9. The mutant PLD enzyme of claim 1, wherein the mutant PLD enzyme exhibits a transphosphatidylation activity of about 30-fold to 125-fold higher as compared to the wild type PLD enzyme.

10. The mutant PLD enzyme of claim 1, wherein the mutant PLD enzyme exhibits a transphosphatidylation activity of about 50-fold to 110-fold higher as compared to the wild type PLD enzyme.

11. The mutant PLD enzyme of claim 1, wherein the mutant PLD enzyme exhibits a transphosphatidylation activity of about 100-fold higher as compared to the wild type PLD enzyme.

12. The mutant PLD enzyme of claim 1, wherein the mutant enzyme exhibits an activity of hydrolysis of phosphatidylcholine to phosphatidic acid that is at least 10-fold higher as compared to the wild type PLD enzyme.

13. The mutant PLD enzyme of claim 1, wherein the mutant PLD enzyme exhibits an activity of hydrolysis of phosphatidylcholine to phosphatidic acid that is about 10-fold to 50-fold higher as compared to the wild type PLD enzyme.

14. The mutant PLD enzyme of claim 1, wherein the mutant PLD enzyme exhibits an activity of hydrolysis of phosphatidylcholine to phosphatidic acid that is about 30-fold higher as compared to the wild type PLD enzyme.

15. The mutant PLD enzyme of claim 12, wherein the activity of hydrolysis of phosphatidylcholine to phosphatidic acid is measured in cells.

16. An isolated nucleic acid encoding the mutant PLD enzyme according to claim 1.

17. An expression vector comprising the isolated nucleic acid of claim 16.

18. A host cell comprising the expression vector of claim 17, optionally the cell is an HEK293T cell.

19. A method of using a mutant PLD enzyme as a catalyst for in vitro synthesis of phospholipids, the method comprising synthesizing phospholipids from phosphatidylcholine and an alcohol substrate using a mutant PLD enzyme according to claim 1, wherein the phospholipid head of the phosphatidylcholine is replaced to form a natural or unnatural phosphatidyl alcohol.

20. The method of claim 19, wherein the unnatural phosphatidyl alcohol comprises a reactive polar head and is synthesized with high selectivity and high yield.

21. The method of claim 20, wherein the reactive head comprises an azide, an alkyne, or trans-cyclooctene alcohols.

22. The method of claim 21, wherein the phosphatidyl alcohol synthesized comprises dioleoyl phosphatidyl alcohol (DOPAlc), dioleoyl phosphatidic acid (DOPA), dipalmitoyl phosphatidyl alcohol or DPPA.

23. A method of using a mutant PLD enzyme as a catalyst for synthesis of phospholipids in a mammalian cell, the method comprising synthesizing phospholipids from phosphatidylcholine and an alcohol substrate using a mutant PLD enzyme according to claim 1, wherein the phospholipid head of the phosphatidylcholine is replaced to form a natural or unnatural phosphatidyl alcohol, thereby making phospholipids.

24. A method of using a mutant PLD enzyme to modulate phosphatidic acid (PA)-dependent Hippo growth restriction pathway, the method comprising increasing the PA made at the plasma membrane using a mutant PLD enzyme according to claim 1, wherein the PA attenuates Hippo growth restriction pathway by triggering translocation of Yes-associated protein (YAP) from the cytosol to the nucleus in serum-starved cells.

25. A method of using a mutant PLD enzyme to modulate PA-dependent AMP-activated protein kinase (AMPK) signaling, the method comprising synthesizing PA made at cellular membranes using a mutant PLD enzyme according to claim 1, wherein the PA induces liver kinase B1 (LKB1) translocation to PA-rich membranes, leading to an increase of AMPK phosphorylation.

26. A method of using a mutant PLD enzyme to modulate PA-dependent mammalian target of rapamycin (mTOR) signaling, the method comprising treating cells expressing plasma membrane-targeted optoPLD with an AMPK inhibitor followed by using a mutant PLD enzyme according to claim 1; wherein the mutant PLD enzyme increases phosphorylation of the mTOR effector S6 kinase.

* * * * *